(12) United States Patent
Damager et al.

(10) Patent No.: US 11,549,104 B2
(45) Date of Patent: *Jan. 10, 2023

(54) POLYPEPTIDES HAVING BETA-GLUCANASE ACTIVITY, POLYNUCLEOTIDES ENCODING SAME AND USES THEREOF IN CLEANING AND DETERGENT COMPOSITIONS

(71) Applicant: NOVOZYMES A/S, Bagsvaerd (DK)

(72) Inventors: Iben Damager, Vaerloese (DK); Morten Gjermansen, Greve (DK); Carsten Andersen, Vaerloese (DK); Thomas Weber, Dormagen (DE); Inga Kerstin Vockenroth, Dusseldorf (DE); Clarissa Maisey, Dusseldorf (DE); Astrid Spitz, Moers (DE); Lisa-Marie Schütz, Hilden (DE); Claudia Ottow, Ratingen (DE); Daniela Herbst, Dusseldorf (DE); Claudia Lindner, Solingen (DE)

(73) Assignee: NOVOZYMES A/S, Bagsvaerd (DK)

( * ) Notice: Subject to any disclaimer, the term of this patent is extended or adjusted under 35 U.S.C. 154(b) by 198 days.

This patent is subject to a terminal disclaimer.

(21) Appl. No.: 15/781,765

(22) PCT Filed: Dec. 7, 2016

(86) PCT No.: PCT/EP2016/080157
§ 371 (c)(1),
(2) Date: Jun. 6, 2018

(87) PCT Pub. No.: WO2017/097866
PCT Pub. Date: Jun. 15, 2017

(65) Prior Publication Data
US 2020/0165590 A1    May 28, 2020

(30) Foreign Application Priority Data

Dec. 7, 2015 (EP) .................................... 15198277
Dec. 7, 2015 (EP) .................................... 15198282

(51) Int. Cl.
C12N 9/00 (2006.01)
C12N 15/52 (2006.01)
C12N 9/42 (2006.01)
C11D 3/386 (2006.01)

(52) U.S. Cl.
CPC ............ *C12N 9/2448* (2013.01); *C11D 3/386* (2013.01); *C12N 15/52* (2013.01); *C11D 3/38681* (2013.01); *C12Y 302/01073* (2013.01)

(58) Field of Classification Search
None
See application file for complete search history.

(56) References Cited

U.S. PATENT DOCUMENTS

| 6,541,233 B1 | 4/2003 | Hillen et al. |
| 2006/0035800 A1 | 2/2006 | Gibson et al. |
| 2011/0117067 A1 | 5/2011 | Esteghlalian et al. |
| 2013/0025073 A1 | 1/2013 | Souter et al. |
| 2014/0073009 A1 | 3/2014 | Joergensen et al. |
| 2015/0376554 A1 | 12/2015 | Christensen |

FOREIGN PATENT DOCUMENTS

WO    2014/083096 A2    6/2014

OTHER PUBLICATIONS

Chen et al. 1997; Sequencing of a 1,3-1,4-beta-D glucanse (Lichenase) from the anaerobic fungus *Opinomyces* strain PC-2: Properties of the enzyme expressed in *Escherichia coli* and evidence that the gene has a bacterial origin. J. Bacteriol. 179(19); 6028-6034.*
Bishop-Lilly et al, 2014, Uniprot accession No. A0A080UVP7.
Lucas et al, 2011, Uniprot accession No. E6TRB0.
Maktouf et al, 2013, Industrial crops and products 43, 349-354.
Takami et al, 2000, Uniprot accession No. Q9K7X6.
Yang et al, 2014, J Ind Microbiol Biotechnol 41(10), 1487-1495.
Yuki et al, 2014, Uniprot accession No. W4QVK7.
Chaari et al, 2012, Process Biochemistry 47, 509-516.
Anonymous, 2013, NCIB Reference Sequence No. WP_010334360.1.
Lucas et al, 2014, GenBank No. ADU30622.1.
Yuki et al, 2015, Genbank No. GAE36131.1.

* cited by examiner

*Primary Examiner* — Karen Cochrane Carlson
(74) *Attorney, Agent, or Firm* — Kelly Reynolds

(57) ABSTRACT

The present invention relates to polypeptides having beta-glucanase activity, catalytic domains, beta-glucan binding domains and polynucleotides encoding the polypeptides, catalytic domains or beta-glucan binding domains. The invention also relates to nucleic acid constructs, vectors, and host cells comprising the polynucleotides as well as methods of producing and using the polypeptides, catalytic domains or beta-glucan binding domains. The invention further relates to cleaning or detergent compositions comprising polypeptides exhibiting beta-glucanase activity and one or more amylases and/or one or more proteases and uses thereof in cleaning or detergent applications and processes such as cleaning hard-surfaces, dish wash and laundering.

20 Claims, No Drawings
Specification includes a Sequence Listing.

SEQUENCE LISTING

<160> NUMBER OF SEQ ID NOS: 40

<210> SEQ ID NO 1
<211> LENGTH: 1140
<212> TYPE: DNA
<213> ORGANISM: Bacillus sp-62449
<220> FEATURE:
<221> NAME/KEY: CDS
<222> LOCATION: (1)..(1137)
<220> FEATURE:
<221> NAME/KEY: misc_feature
<222> LOCATION: (1)..(3)
<223> OTHER INFORMATION: The first amino acid (position -28) in the
      polypeptide shown in SEQ ID NO: 2 and encoded by the
      polynucleotide shown in SEQ ID NO:1 should be Met, not Val. When
      the first codon is gtg a Met is inserted though gtg normally codes
      for V
<220> FEATURE:
<221> NAME/KEY: sig_peptide
<222> LOCATION: (1)..(84)
<220> FEATURE:
<221> NAME/KEY: mat_peptide
<222> LOCATION: (85)..(1137)

<400> SEQUENCE: 1

```
gtg gtt aaa att aaa att aac aat agt att aga att gta atg ctg acg        48
Val Val Lys Ile Lys Ile Asn Asn Ser Ile Arg Ile Val Met Leu Thr
            -25                 -20                 -15 cta ata atg atg tcc gtt tca gtg gtg gct tat gcg tac aac cca gta        96
Leu Ile Met Met Ser Val Ser Val Val Ala Tyr Ala Tyr Asn Pro Val
        -10                  -5                  -1   1 aca gag gac gaa cta tat cat tcg ttc gat agt cat gat gct cgg aac       144
Thr Glu Asp Glu Leu Tyr His Ser Phe Asp Ser His Asp Ala Arg Asn
  5                  10                  15                  20 tgg cag att tct gat ggt tgg aga aat ggc gat gat ttt ttc ggt tgc       192
Trp Gln Ile Ser Asp Gly Trp Arg Asn Gly Asp Asp Phe Phe Gly Cys
                 25                  30                  35 cat tgg agt caa aac agg gtt aat ttt aat cgt ggt gaa atg gaa cta       240
His Trp Ser Gln Asn Arg Val Asn Phe Asn Arg Gly Glu Met Glu Leu
             40                  45                  50 tct ctt cgt aca aat tat tca tac tca gct ccg tat aat tat gag tgt       288
Ser Leu Arg Thr Asn Tyr Ser Tyr Ser Ala Pro Tyr Asn Tyr Glu Cys
         55                  60                  65 gca gag tat gcg acg agt aat ttc tat gga tat ggt ttg tac gaa gta       336
Ala Glu Tyr Ala Thr Ser Asn Phe Tyr Gly Tyr Gly Leu Tyr Glu Val
     70                  75                  80 tct atg aaa cca gcc aat gta tca gga gtg att tct tct ttc ttc acg       384
Ser Met Lys Pro Ala Asn Val Ser Gly Val Ile Ser Ser Phe Phe Thr
 85                  90                  95                 100 tat aca ggt cct tca tat aat gga gca cct tgg gat gag att gat att       432
Tyr Thr Gly Pro Ser Tyr Asn Gly Ala Pro Trp Asp Glu Ile Asp Ile
                105                 110                 115 gaa ttt cta gga aac gac acg aca aaa gtt caa ttc aat tat tac acg       480
Glu Phe Leu Gly Asn Asp Thr Thr Lys Val Gln Phe Asn Tyr Tyr Thr
            120                 125                 130 aac ggt gta gga gga aat gaa ata att tac gat tta gga ttt gat gct       528
Asn Gly Val Gly Gly Asn Glu Ile Ile Tyr Asp Leu Gly Phe Asp Ala
        135                 140                 145 gca aat agt ttt aat acg tat gcg ttt gat tgg caa gag aat tat att       576
Ala Asn Ser Phe Asn Thr Tyr Ala Phe Asp Trp Gln Glu Asn Tyr Ile
    150                 155                 160 agc tgg tat gtt aat ggg aac ttg gta gct aca gca aca gaa aat att       624
Ser Trp Tyr Val Asn Gly Asn Leu Val Ala Thr Ala Thr Glu Asn Ile
165                 170                 175                 180
```

| | | |
|---|---|---|
| cca agt aac ccg agt aaa atc atg atg aat gtg tgg aat acg tac gga<br>Pro Ser Asn Pro Ser Lys Ile Met Met Asn Val Trp Asn Thr Tyr Gly<br>                185                   190                 195 | | 672 |
| att gat gaa tgg gca ggg gca tat gga gga gaa gcc gct aat gcc acc<br>Ile Asp Glu Trp Ala Gly Ala Tyr Gly Gly Glu Ala Ala Asn Ala Thr<br>                200                   205                 210 | | 720 |
| tat gaa tgg gta cgg tat aca ccg aat aat gga aac aca act cct tcc<br>Tyr Glu Trp Val Arg Tyr Thr Pro Asn Asn Gly Asn Thr Thr Pro Ser<br>                215                   220                 225 | | 768 |
| act gct cct gac ttt caa ttg caa gcg tgt gat tac tca gat tca agt<br>Thr Ala Pro Asp Phe Gln Leu Gln Ala Cys Asp Tyr Ser Asp Ser Ser<br>     230                   235                 240 | | 816 |
| ggg atc aca tct tgg tct tgt ggg gta ggg acc ttt cat tct agt aat<br>Gly Ile Thr Ser Trp Ser Cys Gly Val Gly Thr Phe His Ser Ser Asn<br>245                   250                 255                 260 | | 864 |
| tgg att aaa ttt gat agc gtt gat tta tct aca ggg tat aat gca ttt<br>Trp Ile Lys Phe Asp Ser Val Asp Leu Ser Thr Gly Tyr Asn Ala Phe<br>                   265                   270                 275 | | 912 |
| gct gtc agc tat act tct ccg gga agt ggt agt ttt gat att aga cta<br>Ala Val Ser Tyr Thr Ser Pro Gly Ser Gly Ser Phe Asp Ile Arg Leu<br>             280                   285                 290 | | 960 |
| ggt agt cct cat ggt caa aga att ggt act gta aac tat ggt gca act<br>Gly Ser Pro His Gly Gln Arg Ile Gly Thr Val Asn Tyr Gly Ala Thr<br>         295                   300                 305 | | 1008 |
| ggt ggt tgg tct aac tac gag tgg agt ggt acc ccg tca tta gat gtg<br>Gly Gly Trp Ser Asn Tyr Glu Trp Ser Gly Thr Pro Ser Leu Asp Val<br>310                   315                 320 | | 1056 |
| acc gta aga gga gca cat gat ata tac att gta gct acg agc gga gcg<br>Thr Val Arg Gly Ala His Asp Ile Tyr Ile Val Ala Thr Ser Gly Ala<br>325                   330                 335                 340 | | 1104 |
| gct aat cta agg gaa ttt tgg ttt aaa aat gaa taa<br>Ala Asn Leu Arg Glu Phe Trp Phe Lys Asn Glu<br>             345                   350 | | 1140 |

<210> SEQ ID NO 2
<211> LENGTH: 379
<212> TYPE: PRT
<213> ORGANISM: Bacillus sp-62449

<400> SEQUENCE: 2

Val Val Lys Ile Lys Ile Asn Asn Ser Ile Arg Ile Val Met Leu Thr
        -25                 -20                   -15

Leu Ile Met Met Ser Val Ser Val Val Ala Tyr Ala Tyr Asn Pro Val
        -10                  -5                  -1  1

Thr Glu Asp Glu Leu Tyr His Ser Phe Asp His Asp Ala Arg Asn
5                    10                    15                    20

Trp Gln Ile Ser Asp Gly Trp Arg Asn Gly Asp Phe Phe Gly Cys
                  25                    30                    35

His Trp Ser Gln Asn Arg Val Asn Phe Asn Arg Gly Glu Met Glu Leu
         40                    45                    50

Ser Leu Arg Thr Asn Tyr Ser Tyr Ser Ala Pro Tyr Asn Tyr Glu Cys
        55                   60                   65

Ala Glu Tyr Ala Thr Ser Asn Phe Tyr Gly Tyr Gly Leu Tyr Glu Val
70                    75                    80

Ser Met Lys Pro Ala Asn Val Ser Gly Val Ile Ser Ser Phe Phe Thr
85                    90                    95                100

Tyr Thr Gly Pro Ser Tyr Asn Gly Ala Pro Trp Asp Glu Ile Asp Ile
                105                   110                 115

-continued

```
Glu Phe Leu Gly Asn Asp Thr Thr Lys Val Gln Phe Asn Tyr Tyr Thr
                120                 125                 130

Asn Gly Val Gly Gly Asn Glu Ile Ile Tyr Asp Leu Gly Phe Asp Ala
            135                 140                 145

Ala Asn Ser Phe Asn Thr Tyr Ala Phe Asp Trp Gln Glu Asn Tyr Ile
        150                 155                 160

Ser Trp Tyr Val Asn Gly Asn Leu Val Ala Thr Ala Thr Glu Asn Ile
165                 170                 175                 180

Pro Ser Asn Pro Ser Lys Ile Met Met Asn Val Trp Asn Thr Tyr Gly
                185                 190                 195

Ile Asp Glu Trp Ala Gly Ala Tyr Gly Gly Glu Ala Ala Asn Ala Thr
            200                 205                 210

Tyr Glu Trp Val Arg Tyr Thr Pro Asn Asn Gly Asn Thr Thr Pro Ser
        215                 220                 225

Thr Ala Pro Asp Phe Gln Leu Gln Ala Cys Asp Tyr Ser Asp Ser Ser
230                 235                 240

Gly Ile Thr Ser Trp Ser Cys Gly Val Gly Thr Phe His Ser Ser Asn
245                 250                 255                 260

Trp Ile Lys Phe Asp Ser Val Asp Leu Ser Thr Gly Tyr Asn Ala Phe
                265                 270                 275

Ala Val Ser Tyr Thr Ser Pro Gly Ser Gly Ser Phe Asp Ile Arg Leu
            280                 285                 290

Gly Ser Pro His Gly Gln Arg Ile Gly Thr Val Asn Tyr Gly Ala Thr
        295                 300                 305

Gly Gly Trp Ser Asn Tyr Glu Trp Ser Gly Thr Pro Ser Leu Asp Val
310                 315                 320

Thr Val Arg Gly Ala His Asp Ile Tyr Ile Val Ala Thr Ser Gly Ala
325                 330                 335                 340

Ala Asn Leu Arg Glu Phe Trp Phe Lys Asn Glu
                345                 350

<210> SEQ ID NO 3
<211> LENGTH: 379
<212> TYPE: PRT
<213> ORGANISM: Bacillus sp-62449
<220> FEATURE:
<221> NAME/KEY: SIGNAL
<222> LOCATION: (1)..(28)
<220> FEATURE:
<221> NAME/KEY: mat_peptide
<222> LOCATION: (29)..(379)

<400> SEQUENCE: 3

Met Val Lys Ile Lys Ile Asn Asn Ser Ile Arg Ile Val Met Leu Thr
                -25                 -20                 -15

Leu Ile Met Met Ser Val Ser Val Ala Tyr Ala Tyr Asn Pro Val
            -10                  -5                  -1   1

Thr Glu Asp Glu Leu Tyr His Ser Phe Asp Ser His Asp Ala Arg Asn
 5                   10                  15                  20

Trp Gln Ile Ser Asp Gly Trp Arg Asn Gly Asp Asp Phe Phe Gly Cys
                 25                  30                  35

His Trp Ser Gln Asn Arg Val Asn Phe Asn Arg Gly Glu Met Glu Leu
             40                  45                  50

Ser Leu Arg Thr Asn Tyr Ser Tyr Ser Ala Pro Tyr Asn Tyr Glu Cys
                 55                  60                  65

Ala Glu Tyr Ala Thr Ser Asn Phe Tyr Gly Tyr Gly Leu Tyr Glu Val
 70                  75                  80
```

```
Ser Met Lys Pro Ala Asn Val Gly Val Ile Ser Ser Phe Phe Thr
 85                  90                  95                 100

Tyr Thr Gly Pro Ser Tyr Asn Gly Ala Pro Trp Asp Glu Ile Asp Ile
                105                 110                 115

Glu Phe Leu Gly Asn Asp Thr Thr Lys Val Gln Phe Asn Tyr Tyr Thr
            120                 125                 130

Asn Gly Val Gly Gly Asn Glu Ile Ile Tyr Asp Leu Gly Phe Asp Ala
        135                 140                 145

Ala Asn Ser Phe Asn Thr Tyr Ala Phe Asp Trp Gln Glu Asn Tyr Ile
    150                 155                 160

Ser Trp Tyr Val Asn Gly Asn Leu Val Ala Thr Ala Thr Glu Asn Ile
165                 170                 175                 180

Pro Ser Asn Pro Ser Lys Ile Met Met Asn Val Trp Asn Thr Tyr Gly
                185                 190                 195

Ile Asp Glu Trp Ala Gly Ala Tyr Gly Gly Glu Ala Ala Asn Ala Thr
            200                 205                 210

Tyr Glu Trp Val Arg Tyr Thr Pro Asn Asn Gly Asn Thr Thr Pro Ser
        215                 220                 225

Thr Ala Pro Asp Phe Gln Leu Gln Ala Cys Asp Tyr Ser Asp Ser Ser
    230                 235                 240

Gly Ile Thr Ser Trp Ser Cys Gly Val Gly Thr Phe His Ser Ser Asn
245                 250                 255                 260

Trp Ile Lys Phe Asp Ser Val Asp Leu Ser Thr Gly Tyr Asn Ala Phe
                265                 270                 275

Ala Val Ser Tyr Thr Ser Pro Gly Ser Gly Ser Phe Asp Ile Arg Leu
            280                 285                 290

Gly Ser Pro His Gly Gln Arg Ile Gly Thr Val Asn Tyr Gly Ala Thr
        295                 300                 305

Gly Gly Trp Ser Asn Tyr Glu Trp Ser Gly Thr Pro Ser Leu Asp Val
    310                 315                 320

Thr Val Arg Gly Ala His Asp Ile Tyr Ile Val Ala Thr Ser Gly Ala
325                 330                 335                 340

Ala Asn Leu Arg Glu Phe Trp Phe Lys Asn Glu
                345                 350

<210> SEQ ID NO 4
<211> LENGTH: 831
<212> TYPE: DNA
<213> ORGANISM: Bacillus akibai
<220> FEATURE:
<221> NAME/KEY: CDS
<222> LOCATION: (1)..(828)
<220> FEATURE:
<221> NAME/KEY: sig_peptide
<222> LOCATION: (1)..(93)
<220> FEATURE:
<221> NAME/KEY: mat_peptide
<222> LOCATION: (94)..(828)

<400> SEQUENCE: 4 atg aaa aag aaa ttt gtt tta ttt tct atg tgt tta tta ttg ttt agc     48
Met Lys Lys Lys Phe Val Leu Phe Ser Met Cys Leu Leu Leu Phe Ser
    -30                 -25                 -20 ggc ctc ata act gga tta gtt caa agt cca caa gtt gct gaa gca gca     96
Gly Leu Ile Thr Gly Leu Val Gln Ser Pro Gln Val Ala Glu Ala Ala
-15                 -10                  -5                 -1  1 gaa aga cca att ggg act aca ttt gtt gaa aca ttt gaa tca tat gac    144
Glu Arg Pro Ile Gly Thr Thr Phe Val Glu Thr Phe Glu Ser Tyr Asp
```

```
                5                   10                  15
tca gaa cgt tgg tcg aaa gcg gga gtt tgg aca aat gga caa atg ttt    192
Ser Glu Arg Trp Ser Lys Ala Gly Val Trp Thr Asn Gly Gln Met Phe
        20                  25                  30 aat gca aca tgg tat cca gaa caa gtt act ttt tct gat ggt aag atg    240
Asn Ala Thr Trp Tyr Pro Glu Gln Val Thr Phe Ser Asp Gly Lys Met
 35                  40                  45 aag ttg caa att gat aaa gaa gac aat gaa act gcg agc ccg cca tac    288
Lys Leu Gln Ile Asp Lys Glu Asp Asn Glu Thr Ala Ser Pro Pro Tyr
 50                  55                  60                  65 aaa gct gga gaa ctt cgt aca aac gat ttt tat cac tac ggg ttg ttt    336
Lys Ala Gly Glu Leu Arg Thr Asn Asp Phe Tyr His Tyr Gly Leu Phe
                 70                  75                  80 gaa gtg agt atg aaa cct gca aaa tca acg gga aca gtc tct tca ttt    384
Glu Val Ser Met Lys Pro Ala Lys Ser Thr Gly Thr Val Ser Ser Phe
             85                  90                  95 ttc acc tat act gga cct tgg gat tgg gat aat gat cca tgg gat gaa    432
Phe Thr Tyr Thr Gly Pro Trp Asp Trp Asp Asn Asp Pro Trp Asp Glu
            100                 105                 110 att gat atc gaa ttt tta ggt aag gat act act aaa ata caa ttt aat    480
Ile Asp Ile Glu Phe Leu Gly Lys Asp Thr Thr Lys Ile Gln Phe Asn
        115                 120                 125 tat ttt aca aac gga gta ggc gga aat gag cat tac cat gaa tta gga    528
Tyr Phe Thr Asn Gly Val Gly Gly Asn Glu His Tyr His Glu Leu Gly
130                 135                 140                 145 ttt gat gca gca gat gat ttt aat acg tat gct ttt gag tgg aga cca    576
Phe Asp Ala Ala Asp Asp Phe Asn Thr Tyr Ala Phe Glu Trp Arg Pro
                150                 155                 160 gaa tct att cgt tgg ttt gta aat ggt gaa ctg gtt cat aca gca aca    624
Glu Ser Ile Arg Trp Phe Val Asn Gly Glu Leu Val His Thr Ala Thr
            165                 170                 175 gaa aat ata cca caa aca cca caa aaa ata atg atg aac tta tgg cct    672
Glu Asn Ile Pro Gln Thr Pro Gln Lys Ile Met Met Asn Leu Trp Pro
            180                 185                 190 ggt att gga gta gac ggg tgg act ggt aga ttt aat gga gaa gat act    720
Gly Ile Gly Val Asp Gly Trp Thr Gly Arg Phe Asn Gly Glu Asp Thr
        195                 200                 205 cct gta gtt aca cag tac gat tgg gtg aag tat aca cca ctt gag gaa    768
Pro Val Val Thr Gln Tyr Asp Trp Val Lys Tyr Thr Pro Leu Glu Glu
210                 215                 220                 225 ctg ggc tgt tac aat gag aaa aat aat aaa tac aag aaa tgt aag aaa    816
Leu Gly Cys Tyr Asn Glu Lys Asn Asn Lys Tyr Lys Lys Cys Lys Lys
                230                 235                 240 acg aag gta aaa tag                                                831
Thr Lys Val Lys
            245

<210> SEQ ID NO 5
<211> LENGTH: 276
<212> TYPE: PRT
<213> ORGANISM: Bacillus akibai

<400> SEQUENCE: 5

Met Lys Lys Lys Phe Val Leu Phe Ser Met Cys Leu Leu Phe Ser
        -30                 -25                 -20

Gly Leu Ile Thr Gly Leu Val Gln Ser Pro Gln Val Ala Glu Ala Ala
        -15                 -10                  -5              -1   1

Glu Arg Pro Ile Gly Thr Thr Phe Val Glu Thr Phe Glu Ser Tyr Asp
                 5                  10                  15
```

-continued

```
Ser Glu Arg Trp Ser Lys Ala Gly Val Trp Thr Asn Gly Gln Met Phe
         20                  25                  30

Asn Ala Thr Trp Tyr Pro Glu Gln Val Thr Phe Ser Asp Gly Lys Met
 35                  40                  45

Lys Leu Gln Ile Asp Lys Glu Asp Asn Glu Thr Ala Ser Pro Pro Tyr
 50                  55                  60                  65

Lys Ala Gly Glu Leu Arg Thr Asn Asp Phe Tyr His Tyr Gly Leu Phe
                 70                  75                  80

Glu Val Ser Met Lys Pro Ala Lys Ser Thr Gly Thr Val Ser Ser Phe
                 85                  90                  95

Phe Thr Tyr Thr Gly Pro Trp Asp Trp Asp Asn Asp Pro Trp Asp Glu
                100                 105                 110

Ile Asp Ile Glu Phe Leu Gly Lys Asp Thr Thr Lys Ile Gln Phe Asn
         115                 120                 125

Tyr Phe Thr Asn Gly Val Gly Gly Asn Glu His Tyr His Glu Leu Gly
130                 135                 140                 145

Phe Asp Ala Ala Asp Phe Asn Thr Tyr Ala Phe Glu Trp Arg Pro
                150                 155                 160

Glu Ser Ile Arg Trp Phe Val Asn Gly Glu Leu Val His Thr Ala Thr
         165                 170                 175

Glu Asn Ile Pro Gln Thr Pro Gln Lys Ile Met Met Asn Leu Trp Pro
         180                 185                 190

Gly Ile Gly Val Asp Gly Trp Thr Gly Arg Phe Asn Gly Glu Asp Thr
         195                 200                 205

Pro Val Val Thr Gln Tyr Asp Trp Val Lys Tyr Thr Pro Leu Glu Glu
210                 215                 220                 225

Leu Gly Cys Tyr Asn Glu Lys Asn Asn Lys Tyr Lys Lys Cys Lys Lys
                230                 235                 240

Thr Lys Val Lys
        245

<210> SEQ ID NO 6
<211> LENGTH: 714
<212> TYPE: DNA
<213> ORGANISM: Bacillus agaradhaerens
<220> FEATURE:
<221> NAME/KEY: CDS
<222> LOCATION: (1)..(711)
<220> FEATURE:
<221> NAME/KEY: sig_peptide
<222> LOCATION: (1)..(45)
<220> FEATURE:
<221> NAME/KEY: mat_peptide
<222> LOCATION: (46)..(711)

<400> SEQUENCE: 6 atg ttg acg tta cta atg atg tct ttc gcg ggt gcg gca tat gca cat      48
Met Leu Thr Leu Leu Met Met Ser Phe Ala Gly Ala Ala Tyr Ala His
-15                 -10                  -5                  -1  1 aat cca gta aca gat gaa gaa gtc tat cat tcg ttt aac agt cat gat      96
Asn Pro Val Thr Asp Glu Glu Val Tyr His Ser Phe Asn Ser His Asp
                  5                  10                  15 tgg caa aac tgg aat atg tct gac ggt tgg aaa aat gat gat tac ttt     144
Trp Gln Asn Trp Asn Met Ser Asp Gly Trp Lys Asn Asp Asp Tyr Phe
         20                  25                  30 ttc ggg tgt cat tgg agt cag aac aga gtt aac ttt tat ggt ggg caa     192
Phe Gly Cys His Trp Ser Gln Asn Arg Val Asn Phe Tyr Gly Gly Gln
 35                  40                  45 atg gag ttg tca ctg cgt aca aac tat tca tac gca cct cct tac aac     240
```

| | | | | | | | | | | | | | | | |
|---|---|---|---|---|---|---|---|---|---|---|---|---|---|---|---|
| Met | Glu | Leu | Ser | Leu | Arg | Thr | Asn | Tyr | Ser | Tyr | Ala | Pro | Pro | Tyr | Asn |
| 50 | | | | | 55 | | | | 60 | | | | | 65 | |

| tat | gag | tgt | gcg | gag | tat | acg | acc | aat | aat | ttt | tat | gga | tat | gga | tta | 288 |
|---|---|---|---|---|---|---|---|---|---|---|---|---|---|---|---|---|
| Tyr | Glu | Cys | Ala | Glu | Tyr | Thr | Thr | Asn | Asn | Phe | Tyr | Gly | Tyr | Gly | Leu | |
| | | | | 70 | | | | | 75 | | | | | 80 | | |

| tac | gag | gta | tct | atg | aaa | cca | gca | aag | gta | tca | ggg | gtc | att | tct | tct | 336 |
|---|---|---|---|---|---|---|---|---|---|---|---|---|---|---|---|---|
| Tyr | Glu | Val | Ser | Met | Lys | Pro | Ala | Lys | Val | Ser | Gly | Val | Ile | Ser | Ser | |
| | | | | 85 | | | | | 90 | | | | | 95 | | |

| ttc | ttc | acg | tat | aca | ggg | cct | tcc | tat | aat | gga | gcc | cct | tgg | gat | gaa | 384 |
|---|---|---|---|---|---|---|---|---|---|---|---|---|---|---|---|---|
| Phe | Phe | Thr | Tyr | Thr | Gly | Pro | Ser | Tyr | Asn | Gly | Ala | Pro | Trp | Asp | Glu | |
| | | | | 100 | | | | | 105 | | | | | 110 | | |

| att | gac | att | gaa | ttt | tta | gga | aac | gac | acg | act | aag | gtt | caa | ttc | aat | 432 |
|---|---|---|---|---|---|---|---|---|---|---|---|---|---|---|---|---|
| Ile | Asp | Ile | Glu | Phe | Leu | Gly | Asn | Asp | Thr | Thr | Lys | Val | Gln | Phe | Asn | |
| | | | | 115 | | | | | 120 | | | | | 125 | | |

| tat | tac | aca | gat | ggc | gta | gga | ggg | aat | gaa | ata | ctt | tat | gac | tta | gga | 480 |
|---|---|---|---|---|---|---|---|---|---|---|---|---|---|---|---|---|
| Tyr | Tyr | Thr | Asp | Gly | Val | Gly | Gly | Asn | Glu | Ile | Leu | Tyr | Asp | Leu | Gly | |
| 130 | | | | | 135 | | | | 140 | | | | | 145 | | |

| ttc | gat | gca | gcg | gat | agt | tat | aat | acg | tat | gca | ttc | gat | tgg | caa | gaa | 528 |
|---|---|---|---|---|---|---|---|---|---|---|---|---|---|---|---|---|
| Phe | Asp | Ala | Ala | Asp | Ser | Tyr | Asn | Thr | Tyr | Ala | Phe | Asp | Trp | Gln | Glu | |
| | | | | 150 | | | | | 155 | | | | | 160 | | |

| aat | tat | att | aat | tgg | tat | gtt | aat | ggc | caa | ctt | gtt | gca | aca | gca | acg | 576 |
|---|---|---|---|---|---|---|---|---|---|---|---|---|---|---|---|---|
| Asn | Tyr | Ile | Asn | Trp | Tyr | Val | Asn | Gly | Gln | Leu | Val | Ala | Thr | Ala | Thr | |
| | | | | 165 | | | | | 170 | | | | | 175 | | |

| gaa | aac | ata | cct | agt | aat | cct | agt | aaa | att | atg | atg | aac | att | tgg | aat | 624 |
|---|---|---|---|---|---|---|---|---|---|---|---|---|---|---|---|---|
| Glu | Asn | Ile | Pro | Ser | Asn | Pro | Ser | Lys | Ile | Met | Met | Asn | Ile | Trp | Asn | |
| | | | | 180 | | | | | 185 | | | | | 190 | | |

| acg | tat | ggt | att | gac | gag | tgg | gca | gga | agg | tat | tat | gga | gag | gat | gcc | 672 |
|---|---|---|---|---|---|---|---|---|---|---|---|---|---|---|---|---|
| Thr | Tyr | Gly | Ile | Asp | Glu | Trp | Ala | Gly | Arg | Tyr | Tyr | Gly | Glu | Asp | Ala | |
| | | | 195 | | | | | 200 | | | | | 205 | | | |

| aat | gct | tca | tat | aat | tgg | gtt | cgc | tat | aca | cct | aac | cgt | taa | | | 714 |
|---|---|---|---|---|---|---|---|---|---|---|---|---|---|---|---|---|
| Asn | Ala | Ser | Tyr | Asn | Trp | Val | Arg | Tyr | Thr | Pro | Asn | Arg | | | | |
| 210 | | | | | 215 | | | | 220 | | | | | | | |

<210> SEQ ID NO 7
<211> LENGTH: 237
<212> TYPE: PRT
<213> ORGANISM: Bacillus agaradhaerens

<400> SEQUENCE: 7

| | | | | | | | | | | | | | | | |
|---|---|---|---|---|---|---|---|---|---|---|---|---|---|---|---|
| Met | Leu | Thr | Leu | Leu | Met | Met | Ser | Phe | Ala | Gly | Ala | Ala | Tyr | Ala | His |
| -15 | | | | | -10 | | | | -5 | | | | | -1 | 1 |

| | | | | | | | | | | | | | | | |
|---|---|---|---|---|---|---|---|---|---|---|---|---|---|---|---|
| Asn | Pro | Val | Thr | Asp | Glu | Glu | Val | Tyr | His | Ser | Phe | Asn | Ser | His | Asp |
| | | | 5 | | | | | 10 | | | | | 15 | | |

| | | | | | | | | | | | | | | | |
|---|---|---|---|---|---|---|---|---|---|---|---|---|---|---|---|
| Trp | Gln | Asn | Trp | Asn | Met | Ser | Asp | Gly | Trp | Lys | Asn | Asp | Asp | Tyr | Phe |
| | | 20 | | | | | 25 | | | | | 30 | | | |

| | | | | | | | | | | | | | | | |
|---|---|---|---|---|---|---|---|---|---|---|---|---|---|---|---|
| Phe | Gly | Cys | His | Trp | Ser | Gln | Asn | Arg | Val | Asn | Phe | Tyr | Gly | Gly | Gln |
| | | 35 | | | | | 40 | | | | | 45 | | | |

| | | | | | | | | | | | | | | | |
|---|---|---|---|---|---|---|---|---|---|---|---|---|---|---|---|
| Met | Glu | Leu | Ser | Leu | Arg | Thr | Asn | Tyr | Ser | Tyr | Ala | Pro | Pro | Tyr | Asn |
| 50 | | | | | 55 | | | | 60 | | | | | 65 | |

| | | | | | | | | | | | | | | | |
|---|---|---|---|---|---|---|---|---|---|---|---|---|---|---|---|
| Tyr | Glu | Cys | Ala | Glu | Tyr | Thr | Thr | Asn | Asn | Phe | Tyr | Gly | Tyr | Gly | Leu |
| | | | | 70 | | | | | 75 | | | | | 80 | |

| | | | | | | | | | | | | | | | |
|---|---|---|---|---|---|---|---|---|---|---|---|---|---|---|---|
| Tyr | Glu | Val | Ser | Met | Lys | Pro | Ala | Lys | Val | Ser | Gly | Val | Ile | Ser | Ser |
| | | | | 85 | | | | | 90 | | | | | 95 | |

| | | | | | | | | | | | | | | | |
|---|---|---|---|---|---|---|---|---|---|---|---|---|---|---|---|
| Phe | Phe | Thr | Tyr | Thr | Gly | Pro | Ser | Tyr | Asn | Gly | Ala | Pro | Trp | Asp | Glu |
| | | | | 100 | | | | | 105 | | | | | 110 | |

| | | | | | | | | | | | | | | | |
|---|---|---|---|---|---|---|---|---|---|---|---|---|---|---|---|
| Ile | Asp | Ile | Glu | Phe | Leu | Gly | Asn | Asp | Thr | Thr | Lys | Val | Gln | Phe | Asn |
| | | | | 115 | | | | | 120 | | | | | 125 | |

| | | | | | | | | | | | | | | | |
|---|---|---|---|---|---|---|---|---|---|---|---|---|---|---|---|
| Tyr | Tyr | Thr | Asp | Gly | Val | Gly | Gly | Asn | Glu | Ile | Leu | Tyr | Asp | Leu | Gly |

```
                     130                 135                 140                 145
Phe Asp Ala Ala Asp Ser Tyr Asn Thr Tyr Ala Phe Asp Trp Gln Glu
                150                 155                 160

Asn Tyr Ile Asn Trp Tyr Val Asn Gly Gln Leu Val Ala Thr Ala Thr
            165                 170                 175

Glu Asn Ile Pro Ser Asn Pro Ser Lys Ile Met Met Asn Ile Trp Asn
        180                 185                 190

Thr Tyr Gly Ile Asp Glu Trp Ala Gly Arg Tyr Tyr Gly Glu Asp Ala
    195                 200                 205

Asn Ala Ser Tyr Asn Trp Val Arg Tyr Thr Pro Asn Arg
210                 215                 220

<210> SEQ ID NO 8
<211> LENGTH: 732
<212> TYPE: DNA
<213> ORGANISM: Bacillus mojavensis
<220> FEATURE:
<221> NAME/KEY: CDS
<222> LOCATION: (1)..(729)
<220> FEATURE:
<221> NAME/KEY: sig_peptide
<222> LOCATION: (1)..(87)
<220> FEATURE:
<221> NAME/KEY: mat_peptide
<222> LOCATION: (88)..(729)

<400> SEQUENCE: 8
```

| | | | | | | | | | | | | | | | | |
|---|---|---|---|---|---|---|---|---|---|---|---|---|---|---|---|---|
| atg | tct | tat | cgt | atg | aaa | cga | gta | ttg | ttg | ctt | ctt | gtt | act | ggg | ttg | 48 |
| Met | Ser | Tyr | Arg | Met | Lys | Arg | Val | Leu | Leu | Leu | Leu | Val | Thr | Gly | Leu | |
| | | | -25 | | | | | -20 | | | | | -15 | | | |
| ttt | atg | agt | ttg | tct | gca | ttc | act | tct | act | gcc | tcg | gct | caa | aca | ggt | 96 |
| Phe | Met | Ser | Leu | Ser | Ala | Phe | Thr | Ser | Thr | Ala | Ser | Ala | Gln | Thr | Gly | |
| | | | -10 | | | | | -5 | | | | | -1  1 | | | |
| gga | tcg | ttt | ttt | gac | ccc | ttt | aat | ggc | tac | aac | tcc | ggt | ttt | tgg | caa | 144 |
| Gly | Ser | Phe | Phe | Asp | Pro | Phe | Asn | Gly | Tyr | Asn | Ser | Gly | Phe | Trp | Gln | |
| | 5 | | | | 10 | | | | | 15 | | | | | | |
| aag | gca | aat | ggc | tat | tcg | aat | gga | aat | atg | ttt | aac | tgt | acc | tgg | cgt | 192 |
| Lys | Ala | Asn | Gly | Tyr | Ser | Asn | Gly | Asn | Met | Phe | Asn | Cys | Thr | Trp | Arg | |
| 20 | | | | 25 | | | | | 30 | | | | | 35 | | |
| gca | aat | aac | gta | tca | atg | acg | tca | tta | ggg | gaa | atg | cgt | ttg | gcg | cta | 240 |
| Ala | Asn | Asn | Val | Ser | Met | Thr | Ser | Leu | Gly | Glu | Met | Arg | Leu | Ala | Leu | |
| | | | 40 | | | | | 45 | | | | | 50 | | | |
| aca | agt | cca | tct | tat | aac | aag | ttt | gac | tgc | ggg | gaa | aac | cgc | tct | gtt | 288 |
| Thr | Ser | Pro | Ser | Tyr | Asn | Lys | Phe | Asp | Cys | Gly | Glu | Asn | Arg | Ser | Val | |
| | | | 55 | | | | | 60 | | | | | 65 | | | |
| caa | aca | tat | ggc | tat | gga | ctt | tat | gaa | gtc | agg | atg | aaa | cca | gct | aaa | 336 |
| Gln | Thr | Tyr | Gly | Tyr | Gly | Leu | Tyr | Glu | Val | Arg | Met | Lys | Pro | Ala | Lys | |
| | | 70 | | | | | 75 | | | | | 80 | | | | |
| aac | gta | gga | att | gtt | tca | tcg | ttc | ttc | act | tac | aca | ggt | cca | aca | gat | 384 |
| Asn | Val | Gly | Ile | Val | Ser | Ser | Phe | Phe | Thr | Tyr | Thr | Gly | Pro | Thr | Asp | |
| | 85 | | | | | 90 | | | | | 95 | | | | | |
| gga | act | cct | tgg | gat | gag | att | gat | atc | gaa | ttt | tta | gga | aaa | gac | aca | 432 |
| Gly | Thr | Pro | Trp | Asp | Glu | Ile | Asp | Ile | Glu | Phe | Leu | Gly | Lys | Asp | Thr | |
| 100 | | | | | 105 | | | | | 110 | | | | | 115 | |
| aca | aag | gtt | caa | ttt | aac | tat | tat | aca | aat | ggt | gta | gga | aac | cat | gag | 480 |
| Thr | Lys | Val | Gln | Phe | Asn | Tyr | Tyr | Thr | Asn | Gly | Val | Gly | Asn | His | Glu | |
| | | | 120 | | | | | 125 | | | | | 130 | | | |
| aag | ctc | gtg | gat | ctc | gga | ttt | gat | gct | gcc | aac | gcc | tat | cat | acg | tat | 528 |
| Lys | Leu | Val | Asp | Leu | Gly | Phe | Asp | Ala | Ala | Asn | Ala | Tyr | His | Thr | Tyr | |
| | | | 135 | | | | | 140 | | | | | 145 | | | |
| gcg | ttc | gat | tgg | cag | cca | aac | tct | att | aaa | tgg | tat | gtc | gat | ggg | caa | 576 |

```
Ala Phe Asp Trp Gln Pro Asn Ser Ile Lys Trp Tyr Val Asp Gly Gln
            150                 155                 160 tta aaa cat act gcg aca agc caa att ccg aca aca cca ggt aag atc         624
Leu Lys His Thr Ala Thr Ser Gln Ile Pro Thr Thr Pro Gly Lys Ile
165                 170                 175 atg atg aac ttg tgg aat ggt acg ggt gta gat gaa tgg ctc ggt tcc         672
Met Met Asn Leu Trp Asn Gly Thr Gly Val Asp Glu Trp Leu Gly Ser
180                 185                 190                 195 tac aat ggt gtg aca ccg cta tac gct cat tac gac tgg gtg cgc tat         720
Tyr Asn Gly Val Thr Pro Leu Tyr Ala His Tyr Asp Trp Val Arg Tyr
                200                 205                 210 aca aaa aaa taa                                                         732
Thr Lys Lys
```

<210> SEQ ID NO 9
<211> LENGTH: 243
<212> TYPE: PRT
<213> ORGANISM: Bacillus mojavensis

<400> SEQUENCE: 9

```
Met Ser Tyr Arg Met Lys Arg Val Leu Leu Leu Val Thr Gly Leu
            -25                 -20                 -15

Phe Met Ser Leu Ser Ala Phe Thr Ser Thr Ala Ser Ala Gln Thr Gly
            -10                  -5                  -1   1

Gly Ser Phe Phe Asp P

```
<221> NAME/KEY: SIGNAL
<222> LOCATION: (1)..(27)
<223> OTHER INFORMATION: Secretion signal

<400> SEQUENCE: 10

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 11
<211> LENGTH: 8
<212> TYPE: PRT
<213> ORGANISM: Artificial Sequence
<220> FEATURE:
<223> OTHER INFORMATION: N-terminal poly histidine affinity purification
      tag

<400> SEQUENCE: 11

His His His His His His Pro Arg
1               5

<210> SEQ ID NO 12
<211> LENGTH: 483
<212> TYPE: PRT
<213> ORGANISM: Bacillus sp.

<400> SEQUENCE: 12

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Lys Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Lys Gly Trp Asp Trp Glu Val Asp Thr Glu
            180                 185                 190

Phe Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240
```

```
Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Gln Ile Phe Asn Gly Thr Val Gln Lys His Pro
305                 310                 315                 320

Met His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365

Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Arg Gln Asn
385                 390                 395                 400

Asp Tyr Leu Asp His His Asn Ile Ile Gly Trp Thr Arg Glu Gly Asn
                405                 410                 415

Thr Ala His Pro Asn Ser Gly Leu Ala Thr Ile Met Ser Asp Gly Ala
            420                 425                 430

Gly Gly Asn Lys Trp Met Phe Val Gly Arg Asn Lys Ala Gly Gln Val
        435                 440                 445

Trp Thr Asp Ile Thr Gly Asn Lys Ala Gly Thr Val Thr Ile Asn Ala
    450                 455                 460

Asp Gly Trp Gly Asn Phe Ser Val Asn Gly Gly Ser Val Ser Ile Trp
465                 470                 475                 480

Val Asn Lys

<210> SEQ ID NO 13
<211> LENGTH: 483
<212> TYPE: PRT
<213> ORGANISM: Bacillus licheniformis
<220> FEATURE:
<221> NAME/KEY: MISC_FEATURE
<223> OTHER INFORMATION: corresponding to SEQ ID NO: 2 in WO 95/10603

<400> SEQUENCE: 13

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Ala Asp Ala Thr
            100                 105                 110
```

```
Glu Asp Val Thr Ala Val Glu Val Asp Pro Ala Asp Arg Asn Arg Val
            115                 120                 125
Ile Ser Gly Glu His Leu Ile Lys Ala Trp Thr His Phe His Phe Pro
        130                 135                 140
Gly Arg Gly Ser Thr Tyr Ser Asp Phe Lys Trp His Trp Tyr His Phe
145                 150                 155                 160
Asp Gly Thr Asp Trp Asp Glu Ser Arg Lys Leu Asn Arg Ile Tyr Lys
                165                 170                 175
Phe Gln Gly Lys Ala Trp Asp Trp Glu Val Ser Asn Glu Asn Gly Asn
            180                 185                 190
Tyr Asp Tyr Leu Met Tyr Ala Asp Ile Asp Tyr Asp His Pro Asp Val
        195                 200                 205
Ala Ala Glu Ile Lys Arg Trp Gly Thr Trp Tyr Ala Asn Glu Leu Gln
    210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Ala Glu Tyr Trp Gln Asn Asp Leu Gly Ala Leu Glu Asn
            260                 265                 270
Tyr Leu Asn Lys Thr Asn Phe Asn His Ser Val Phe Asp Val Pro Leu
        275                 280                 285
His Tyr Gln Phe His Ala Ala Ser Thr Gln Gly Gly Gly Tyr Asp Met
    290                 295                 300
Arg Lys Leu Leu Asn Gly Thr Val Val Ser Lys His Pro Leu Lys Ser
305                 310                 315                 320
Val Thr Phe Val Asp Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
        355                 360                 365
Thr Lys Gly Asp Ser Gln Arg Glu Ile Pro Ala Leu Lys His Lys Ile
    370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                405                 410                 415
Ser Ser Val Ala Asn Ser Gly Leu Ala Ala Leu Ile Thr Asp Gly Pro
            420                 425                 430
Gly Gly Ala Lys Arg Met Tyr Val Gly Arg Gln Asn Ala Gly Glu Thr
        435                 440                 445
Trp His Asp Ile Thr Gly Asn Arg Ser Glu Pro Val Val Ile Asn Ser
    450                 455                 460
Glu Gly Trp Gly Glu Phe His Val Asn Gly Gly Ser Val Ser Ile Tyr
465                 470                 475                 480
Val Gln Arg

<210> SEQ ID NO 14
<211> LENGTH: 515
<212> TYPE: PRT
<213> ORGANISM: Bacillus stearothermophilus
<220> FEATURE:
<221> NAME/KEY: MISC_FEATURE
<223> OTHER INFORMATION: corresponding to SEQ ID NO: 6 in WO 2002/010355
```

<400> SEQUENCE: 14

```
Ala Ala Pro Phe Asn Gly Thr Met Met Gln Tyr Phe Glu Trp Tyr Leu
1               5                   10                  15
Pro Asp Asp Gly Thr Leu Trp Thr Lys Val Ala Asn Glu Ala Asn Asn
                20                  25                  30
Leu Ser Ser Leu Gly Ile Thr Ala Leu Trp Leu Pro Pro Ala Tyr Lys
            35                  40                  45
Gly Thr Ser Arg Ser Asp Val Gly Tyr Gly Val Tyr Asp Leu Tyr Asp
        50                  55                  60
Leu Gly Glu Phe Asn Gln Lys Gly Thr Val Arg Thr Lys Tyr Gly Thr
65                  70                  75                  80
Lys Ala Gln Tyr Leu Gln Ala Ile Gln Ala Ala His Ala Ala Gly Met
                85                  90                  95
Gln Val Tyr Ala Asp Val Val Phe Asp His Lys Gly Gly Ala Asp Gly
                100                 105                 110
Thr Glu Trp Val Asp Ala Val Glu Val Asn Pro Ser Asp Arg Asn Gln
            115                 120                 125
Glu Ile Ser Gly Thr Tyr Gln Ile Gln Ala Trp Thr Lys Phe Asp Phe
130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                165                 170                 175
Lys Phe Arg Gly Ile Gly Lys Ala Trp Asp Trp Glu Val Asp Thr Glu
                180                 185                 190
Asn Gly Asn Tyr Asp Tyr Leu Met Tyr Ala Asp Leu Asp Met Asp His
            195                 200                 205
Pro Glu Val Val Thr Glu Leu Lys Asn Trp Gly Lys Trp Tyr Val Asn
210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Tyr Val Arg Ser Gln Thr Gly
                245                 250                 255
Lys Pro Leu Phe Thr Val Gly Glu Tyr Trp Ser Tyr Asp Ile Asn Lys
                260                 265                 270
Leu His Asn Tyr Ile Thr Lys Thr Asp Gly Thr Met Ser Leu Phe Asp
            275                 280                 285
Ala Pro Leu His Asn Lys Phe Tyr Thr Ala Ser Lys Ser Gly Gly Ala
        290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                325                 330                 335
Ala Leu Gln Ser Trp Val Asp Pro Trp Phe Lys Pro Leu Ala Tyr Ala
            340                 345                 350
Phe Ile Leu Thr Arg Gln Glu Gly Tyr Pro Cys Val Phe Tyr Gly Asp
        355                 360                 365
Tyr Tyr Gly Ile Pro Gln Tyr Asn Ile Pro Ser Leu Lys Ser Lys Ile
        370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Gly
```

```
            405                 410                 415
Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
            450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
            485                 490                 495

Arg Pro Trp Thr Gly Glu Phe Val Arg Trp Thr Pro Arg Leu Val
            500                 505                 510

Ala Trp Pro
            515

<210> SEQ ID NO 15
<211> LENGTH: 481
<212> TYPE: PRT
<213> ORGANISM: Artificial Sequence
<220> FEATURE:
<223> OTHER INFORMATION: Residues 1-33 of SEQ ID NO: 6 of WO 2006/066594
      and residues 36-483 of SEQ ID NO: 4 of WO 2006/066594
<220> FEATURE:
<221> NAME/KEY: MISC_FEATURE
<223> OTHER INFORMATION: corresponding to the hybrid polypeptide
      comprising residues 1-33 of SEQ ID NO: 6 of WO 2006/066594 and
      residues 36-483 of SEQ ID NO: 4 of WO 2006/066594

<400> SEQUENCE: 15

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Thr Ser
            35                  40                  45

Gln Ala Asp Val Gly Tyr Gly Ala Tyr Asp Leu Tyr Asp Leu Gly Glu
    50                  55                  60

Phe His Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Gly Gly Ala Asp Ala Thr Glu Asp
            100                 105                 110

Val Thr Ala Val Glu Val Asp Pro Ala Asp Arg Asn Arg Val Ile Ser
            115                 120                 125

Gly Glu His Leu Ile Lys Ala Trp Thr His Phe His Phe Pro Gly Arg
    130                 135                 140

Gly Ser Thr Tyr Ser Asp Phe Lys Trp His Trp Tyr His Phe Asp Gly
145                 150                 155                 160

Thr Asp Trp Asp Glu Ser Arg Lys Leu Asn Arg Ile Tyr Lys Phe Gln
                165                 170                 175

Gly Lys Ala Trp Asp Trp Glu Val Ser Asn Glu Asn Gly Asn Tyr Asp
            180                 185                 190

Tyr Leu Met Tyr Ala Asp Ile Asp Tyr Asp His Pro Asp Val Ala Ala
            195                 200                 205

Glu Ile Lys Arg Trp Gly Thr Trp Tyr Ala Asn Glu Leu Gln Leu Asp
```

```
                210                 215                 220
Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255

Val Ala Glu Tyr Trp Gln Asn Asp Leu Gly Ala Leu Glu Asn Tyr Leu
            260                 265                 270

Asn Lys Thr Asn Phe Asn His Ser Val Phe Asp Val Pro Leu His Tyr
                275                 280                 285

Gln Phe His Ala Ala Ser Thr Gln Gly Gly Tyr Asp Met Arg Lys
290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335

Val Gln Thr Trp Phe Lys Pro Leu Ala Tyr Ala Phe Ile Leu Thr Arg
            340                 345                 350

Glu Ser Gly Tyr Pro Gln Val Phe Tyr Gly Asp Met Tyr Gly Thr Lys
                355                 360                 365

Gly Asp Ser Gln Arg Glu Ile Pro Ala Leu Lys His Lys Ile Glu Pro
370                 375                 380

Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Asp Ser Ser
                405                 410                 415

Val Ala Asn Ser Gly Leu Ala Ala Leu Ile Thr Asp Gly Pro Gly Gly
            420                 425                 430

Ala Lys Arg Met Tyr Val Gly Arg Gln Asn Ala Gly Glu Thr Trp His
                435                 440                 445

Asp Ile Thr Gly Asn Arg Ser Glu Pro Val Val Ile Asn Ser Glu Gly
450                 455                 460

Trp Gly Glu Phe His Val Asn Gly Gly Ser Val Ser Ile Tyr Val Gln
465                 470                 475                 480

Arg

<210> SEQ ID NO 16
<211> LENGTH: 485
<212> TYPE: PRT
<213> ORGANISM: Bacillus sp.
<220> FEATURE:
<221> NAME/KEY: MISC_FEATURE
<223> OTHER INFORMATION: corresponding to SEQ ID NO: 6 of WO 2002/019467

<400> SEQUENCE: 16

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
```

```
                     85                  90                  95
Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
                115                 120                 125

Gln Glu Val Thr Gly Glu Tyr Thr Ile Glu Ala Trp Thr Arg Phe Asp
        130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
                180                 185                 190

Thr Glu Asn Gly Asn Tyr Asp Tyr Leu Met Tyr Ala Asp Ile Asp Met
                195                 200                 205

Asp His Pro Glu Val Val Asn Glu Leu Arg Asn Trp Gly Val Trp Tyr
        210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
                260                 265                 270

Gly Ala Ile Glu Asn Tyr Leu Gln Lys Thr Asn Trp Asn His Ser Val
                275                 280                 285

Phe Asp Val Pro Leu His Tyr Asn Leu Tyr Asn Ala Ser Lys Ser Gly
        290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
        450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 17
```

```
<211> LENGTH: 485
<212> TYPE: PRT
<213> ORGANISM: Bacillus sp. NCIB 12512
<220> FEATURE:
<221> NAME/KEY: MISC_FEATURE
<223> OTHER INFORMATION: corresponding to SEQ ID NO: 1 of WO 1996/023873

<400> SEQUENCE: 17
```

| His | His | Asn | Gly | Thr | Asn | Gly | Thr | Met | Met | Gln | Tyr | Phe | Glu | Trp | Tyr |
|---|---|---|---|---|---|---|---|---|---|---|---|---|---|---|---|
| 1 | | | | 5 | | | | | 10 | | | | | 15 | |
| Leu | Pro | Asn | Asp | Gly | Asn | His | Trp | Asn | Arg | Leu | Arg | Asp | Asp | Ala | Ala |
| | | | 20 | | | | | 25 | | | | | 30 | | |
| Asn | Leu | Lys | Ser | Lys | Gly | Ile | Thr | Ala | Val | Trp | Ile | Pro | Pro | Ala | Trp |
| | | 35 | | | | | 40 | | | | | 45 | | | |
| Lys | Gly | Thr | Ser | Gln | Asn | Asp | Val | Gly | Tyr | Gly | Ala | Tyr | Asp | Leu | Tyr |
| | 50 | | | | | 55 | | | | | 60 | | | | |
| Asp | Leu | Gly | Glu | Phe | Asn | Gln | Lys | Gly | Thr | Val | Arg | Thr | Lys | Tyr | Gly |
| 65 | | | | | 70 | | | | | 75 | | | | | 80 |
| Thr | Arg | Asn | Gln | Leu | Gln | Ala | Ala | Val | Thr | Ser | Leu | Lys | Asn | Asn | Gly |
| | | | | 85 | | | | | 90 | | | | | 95 | |
| Ile | Gln | Val | Tyr | Gly | Asp | Val | Val | Met | Asn | His | Lys | Gly | Gly | Ala | Asp |
| | | | 100 | | | | | 105 | | | | | 110 | | |
| Gly | Thr | Glu | Ile | Val | Asn | Ala | Val | Glu | Val | Asn | Arg | Ser | Asn | Arg | Asn |
| | | 115 | | | | | 120 | | | | | 125 | | | |
| Gln | Glu | Thr | Ser | Gly | Glu | Tyr | Ala | Ile | Glu | Ala | Trp | Thr | Lys | Phe | Asp |
| | 130 | | | | | 135 | | | | | 140 | | | | |
| Phe | Pro | Gly | Arg | Gly | Asn | Asn | His | Ser | Ser | Phe | Lys | Trp | Arg | Trp | Tyr |
| 145 | | | | | 150 | | | | | 155 | | | | | 160 |
| His | Phe | Asp | Gly | Thr | Asp | Trp | Asp | Gln | Ser | Arg | Gln | Leu | Gln | Asn | Lys |
| | | | | 165 | | | | | 170 | | | | | 175 | |
| Ile | Tyr | Lys | Phe | Arg | Gly | Thr | Gly | Lys | Ala | Trp | Asp | Trp | Glu | Val | Asp |
| | | | 180 | | | | | 185 | | | | | 190 | | |
| Thr | Glu | Asn | Gly | Asn | Tyr | Asp | Tyr | Leu | Met | Tyr | Ala | Asp | Val | Asp | Met |
| | | 195 | | | | | 200 | | | | | 205 | | | |
| Asp | His | Pro | Glu | Val | Ile | His | Glu | Leu | Arg | Asn | Trp | Gly | Val | Trp | Tyr |
| | 210 | | | | | 215 | | | | | 220 | | | | |
| Thr | Asn | Thr | Leu | Asn | Leu | Asp | Gly | Phe | Arg | Ile | Asp | Ala | Val | Lys | His |
| 225 | | | | | 230 | | | | | 235 | | | | | 240 |
| Ile | Lys | Tyr | Ser | Phe | Thr | Arg | Asp | Trp | Leu | Thr | His | Val | Arg | Asn | Thr |
| | | | | 245 | | | | | 250 | | | | | 255 | |
| Thr | Gly | Lys | Pro | Met | Phe | Ala | Val | Ala | Glu | Phe | Trp | Lys | Asn | Asp | Leu |
| | | | 260 | | | | | 265 | | | | | 270 | | |
| Gly | Ala | Ile | Glu | Asn | Tyr | Leu | Asn | Lys | Thr | Ser | Trp | Asn | His | Ser | Val |
| | | 275 | | | | | 280 | | | | | 285 | | | |
| Phe | Asp | Val | Pro | Leu | His | Tyr | Asn | Leu | Tyr | Asn | Ala | Ser | Asn | Ser | Gly |
| | 290 | | | | | 295 | | | | | 300 | | | | |
| Gly | Tyr | Tyr | Asp | Met | Arg | Asn | Ile | Leu | Asn | Gly | Ser | Val | Val | Gln | Lys |
| 305 | | | | | 310 | | | | | 315 | | | | | 320 |
| His | Pro | Thr | His | Ala | Val | Thr | Phe | Val | Asp | Asn | His | Asp | Ser | Gln | Pro |
| | | | | 325 | | | | | 330 | | | | | 335 | |
| Gly | Glu | Ala | Leu | Glu | Ser | Phe | Val | Gln | Gln | Trp | Phe | Lys | Pro | Leu | Ala |
| | | | 340 | | | | | 345 | | | | | 350 | | |
| Tyr | Ala | Leu | Val | Leu | Thr | Arg | Glu | Gln | Gly | Tyr | Pro | Ser | Val | Phe | Tyr |
| | | 355 | | | | | 360 | | | | | 365 | | | |
| Gly | Asp | Tyr | Tyr | Gly | Ile | Pro | Thr | His | Gly | Val | Pro | Ala | Met | Lys | Ser |

```
                    370                 375                 380
Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
                420                 425                 430

Gly Pro Gly Gly Asn Lys Trp Met Tyr Val Gly Lys Asn Lys Ala Gly
                435                 440                 445

Gln Val Trp Arg Asp Ile Thr Gly Asn Arg Thr Gly Thr Val Thr Ile
                450                 455                 460

Asn Ala Asp Gly Trp Gly Asn Phe Ser Val Asn Gly Ser Val Ser
465                 470                 475                 480

Val Trp Val Lys Gln
                485

<210> SEQ ID NO 18
<211> LENGTH: 485
<212> TYPE: PRT
<213> ORGANISM: Bacillus sp. NCIB 12513
<220> FEATURE:
<221> NAME/KEY: MISC_FEATURE
<223> OTHER INFORMATION: corresponding to SEQ ID NO: 2 of WO 1996/023873

<400> SEQUENCE: 18

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
                35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
                115                 120                 125

Gln Glu Ile Ser Gly Asp Tyr Thr Ile Glu Ala Trp Thr Lys Phe Asp
                130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
                180                 185                 190

Ser Glu Asn Gly Asn Tyr Asp Tyr Leu Met Tyr Ala Asp Val Asp Met
                195                 200                 205

Asp His Pro Glu Val Val Asn Glu Leu Arg Arg Trp Gly Glu Trp Tyr
                210                 215                 220

Thr Asn Thr Leu Asn Leu Asp Gly Phe Arg Ile Asp Ala Val Lys His
225                 230                 235                 240
```

```
Ile Lys Tyr Ser Phe Thr Arg Asp Trp Leu Thr His Val Arg Asn Ala
            245                 250                 255

Thr Gly Lys Glu Met Phe Ala Val Ala Glu Phe Trp Lys Asn Asp Leu
        260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
                340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
                420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
        450                 455                 460

Asn Ala Asp Gly Trp Ala Asn Phe Ser Val Asn Gly Gly Ser Val Ser
465                 470                 475                 480

Ile Trp Val Lys Arg
            485

<210> SEQ ID NO 19
<211> LENGTH: 485
<212> TYPE: PRT
<213> ORGANISM: Bacillus sp. #707
<220> FEATURE:
<221> NAME/KEY: MISC_FEATURE
<223> OTHER INFORMATION: corresponding to SEQ ID NO: 7 of WO 1996/023873

<400> SEQUENCE: 19

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
                100                 105                 110
```

Ala Thr Glu Met Val Arg Ala Val Glu Val Asn Pro Asn Asn Arg Asn
            115                 120                 125

Gln Glu Val Thr Gly Glu Tyr Thr Ile Glu Ala Trp Thr Arg Phe Asp
        130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 20
<211> LENGTH: 485
<212> TYPE: PRT
<213> ORGANISM: Bacillus sp. A 7-7 (DSM 12368)
<220> FEATURE:

<221> NAME/KEY: MISC_FEATURE
<223> OTHER INFORMATION: corresponding to SEQ ID NO: 2 of WO 2008/153815

<400> SEQUENCE: 20

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Asp Gln Gly Tyr Pro Ser Val Phe Tyr
        355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Lys
385                 390                 395                 400
```

```
Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
        435                 440                 445

Gln Val Trp Arg Asp Ile Thr Gly Asn Arg Ser Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Asn
                485

<210> SEQ ID NO 21
<211> LENGTH: 483
<212> TYPE: PRT
<213> ORGANISM: Bacillus amyloliquefaciens
<220> FEATURE:
<221> NAME/KEY: MISC_FEATURE
<223> OTHER INFORMATION: corresponding to SEQ ID NO: 10 of WO
      2001/066712

<400> SEQUENCE: 21

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255
```

```
Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
            275                 280                 285

His Phe Asn Leu Gln Ala Ala Ser Ser Gln Gly Gly Tyr Asp Met
            290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Thr Ser Pro Lys Glu Ile Pro Ser Leu Lys Asp Asn Ile
            370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
            405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
            450                 455                 460

Asp Gly Trp Gly Glu Phe His Val Asn Asp Gly Ser Val Ser Ile Tyr
465                 470                 475                 480

Val Gln Lys

<210> SEQ ID NO 22
<211> LENGTH: 484
<212> TYPE: PRT
<213> ORGANISM: Bacillus sp. TS-23
<220> FEATURE:
<221> NAME/KEY: MISC_FEATURE
<223> OTHER INFORMATION: corresponding to SEQ ID NO: 2 of WO 2009/061380

<400> SEQUENCE: 22

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
            50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
            85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125
```

```
Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
                180                 185                 190

Glu Asn Gly Asn Tyr Asp Tyr Leu Met Phe Ala Asp Leu Asp Met Asp
            195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
                260                 265                 270

Lys Leu His Asn Tyr Ile Thr Lys Thr Asn Gly Ser Met Ser Leu Phe
            275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
                340                 345                 350

Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
                420                 425                 430

Pro Gly Gly Ser Lys Trp Met Tyr Val Gly Lys Lys His Ala Gly Lys
            435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Ala Lys

<210> SEQ ID NO 23
<211> LENGTH: 485
<212> TYPE: PRT
<213> ORGANISM: Bacillus sp.

<400> SEQUENCE: 23

His His Asp Gly Thr Asn Gly Thr Ile Met Gln Tyr Phe Glu Trp Asn
1               5                   10                  15
```

-continued

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Gln Ile Glu Ala Trp Thr Gly Phe Asn
130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile Asn Glu Leu Asn Arg Trp Gly Val Trp Tyr
210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu His Val Arg Gly Gln
            245                 250                 255

Thr Gly Lys Asn Leu Phe Ala Val Ala Glu Tyr Trp Lys Asn Asp Leu
        260                 265                 270

Gly Ala Leu Glu Asn Tyr Leu Ser Lys Thr Asn Trp Thr Met Ser Ala
        275                 280                 285

Phe Asp Val Pro Leu His Tyr Asn Leu Tyr Gln Ala Ser Asn Ser Ser
290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
        370                 375                 380

Gln Ile Asp Pro Leu Leu Lys Ala Arg Gln Gln Tyr Ala Tyr Gly Arg
385                 390                 395                 400

Gln His Asp Tyr Phe Asp His Trp Asp Val Ile Gly Trp Thr Arg Glu
                405                 410                 415

Gly Asn Ala Ser His Pro Asn Ser Gly Leu Ala Thr Ile Met Ser Asp
            420                 425                 430

Gly Pro Gly Gly Ser Lys Trp Met Tyr Val Gly Arg Gln Lys Ala Gly

```
                435                 440                 445
Glu Val Trp His Asp Met Thr Gly Asn Arg Ser Gly Thr Val Thr Ile
            450                 455                 460

Asn Gln Asp Gly Trp Gly His Phe Phe Val Asn Gly Gly Ser Val Ser
465                 470                 475                 480

Val Trp Val Lys Arg
            485

<210> SEQ ID NO 24
<211> LENGTH: 483
<212> TYPE: PRT
<213> ORGANISM: Bacillus sp.

<400> SEQUENCE: 24

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
            85                  90                  95

Ile Gln Val Tyr Gly Asp Val Val Met Asn His Lys Gly Gly Ala Asp
        100                 105                 110

Ala Thr Glu Met Val Arg Ala Val Glu Val Asn Pro Asn Asn Arg Asn
    115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Gln Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Asn Ile Phe Asn Gly Thr Val Val Gln Arg His Pro
305                 310                 315                 320
```

```
Ser His Ala Val Thr Phe Val Asp Asn His Asp Ser Gln Pro Glu Glu
            325                 330                 335

Ala Leu Glu Ser Phe Val Glu Glu Trp Phe Lys Pro Leu Ala Tyr Ala
        340                 345                 350

Leu Thr Leu Thr Arg Glu Gln Gly Tyr Pro Ser Val Phe Tyr Gly Asp
            355                 360                 365

Tyr Tyr Gly Ile Pro Thr His Gly Val Pro Ala Met Arg Ser Lys Ile
370                 375                 380

Asp Pro Ile Leu Glu Ala Arg Gln Lys Tyr Ala Tyr Gly Pro Gln His
385                 390                 395                 400

Asp Tyr Leu Asp His Pro Asp Val Ile Gly Trp Thr Arg Glu Gly Asp
                405                 410                 415

Ser Ser His Pro Lys Ser Gly Leu Ala Thr Leu Ile Thr Asp Gly Pro
                420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
        450                 455                 460

Asp Gly Trp Gly Glu Phe His Val Asn Asp Gly Ser Val Ser Ile Tyr
465                 470                 475                 480

Val Gln Lys

<210> SEQ ID NO 25
<211> LENGTH: 485
<212> TYPE: PRT
<213> ORGANISM: Bacillus sp.

<400> SEQUENCE: 25

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205
```

```
Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 26
<211> LENGTH: 485
<212> TYPE: PRT
<213> ORGANISM: Cytophaga sp.

<400> SEQUENCE: 26

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
                20                  25                  30

Ser Ser Val Gly Ile Thr Ala Val Trp Thr Pro Pro Ala Tyr Lys Gly
            35                  40                  45

Thr Ser Gln Ala Asp Val Gly Tyr Gly Pro Tyr Asp Leu Tyr Asp Leu
        50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95
```

Val Tyr Gly Asp Val Val Met Asn His Lys Ala Gly Ala Asp Tyr Thr
                100                 105                 110

Glu Asn Val Thr Ala Val Glu Val Asn Pro Ser Asn Arg Asn Gln Glu
            115                 120                 125

Thr Ser Gly Glu Tyr Asn Ile Gln Ala Trp Thr Gly Phe Asn Phe Pro
        130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
    210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
        435                 440                 445

Glu Ile Trp Tyr Asp Leu Thr Gly Asn Arg Thr Asp Lys Ile Thr Ile
    450                 455                 460

Gly Ser Asp Gly Tyr Ala Thr Phe Pro Val Asn Gly Gly Ser Val Ser
465                 470                 475                 480

Val Trp Val Gln Gln
                485

<210> SEQ ID NO 27
<211> LENGTH: 485

```
<212> TYPE: PRT
<213> ORGANISM: Bacillus sp.

<400> SEQUENCE: 27
```

| | | | | | | | | | | | | | | |
|---|---|---|---|---|---|---|---|---|---|---|---|---|---|---|
| His | His | Asn | Gly | Thr | Asn | Gly | Thr | Met | Met | Gln | Tyr | Phe | Glu | Trp | Tyr |
| 1 | | | | 5 | | | | | 10 | | | | | 15 | |

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

```
Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 28
<211> LENGTH: 484
<212> TYPE: PRT
<213> ORGANISM: Bacillus sp.

<400> SEQUENCE: 28

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Thr Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
```

| | | | 275 | | | | 280 | | | | 285 | | |
|---|---|---|---|---|---|---|---|---|---|---|---|---|---|

Asp Ala Pro Leu His Asn Asn Phe Tyr Thr Ala Ser Lys Ser Ser Gly
290 295 300

Tyr Phe Asp Met Arg Tyr Leu Leu Asn Asn Thr Leu Met Lys Asp Gln
305 310 315 320

Pro Ser Leu Ala Val Thr Leu Val Asp Asn His Asp Thr Gln Pro Gly
325 330 335

Gln Ser Leu Gln Ser Trp Val Glu Pro Trp Phe Lys Pro Leu Ala Tyr
340 345 350

Ala Phe Ile Leu Thr Arg Gln Glu Gly Tyr Pro Cys Val Phe Tyr Gly
355 360 365

Asp Tyr Tyr Gly Ile Pro Lys Tyr Asn Ile Pro Gly Leu Lys Ser Lys
370 375 380

Ile Asp Pro Leu Leu Ile Ala Arg Arg Asp Tyr Ala Tyr Gly Thr Gln
385 390 395 400

Arg Asp Tyr Ile Asp His Gln Asp Ile Ile Gly Trp Thr Arg Glu Gly
405 410 415

Ile Asp Thr Lys Pro Asn Ser Gly Leu Ala Ala Leu Ile Thr Asp Gly
420 425 430

Pro Gly Gly Ser Lys Trp Met Tyr Val Gly Lys Lys His Ala Gly Lys
435 440 445

Val Phe Tyr Asp Leu Thr Gly Asn Arg Ser Asp Thr Val Thr Ile Asn
450 455 460

Ala Asp Gly Trp Gly Glu Phe Lys Val Asn Gly Gly Ser Val Ser Ile
465 470 475 480

Trp Val Ala Lys

<210> SEQ ID NO 29
<211> LENGTH: 485
<212> TYPE: PRT
<213> ORGANISM: Bacillus halmapalus

<400> SEQUENCE: 29

His His Asn Gly Thr Asn Gly Thr Met Met Gln Tyr Phe Glu Trp His
1 5 10 15

Leu Pro Asn Asp Gly Asn His Trp Asn Arg Leu Arg Asp Asp Ala Ser
20 25 30

Asn Leu Arg Asn Arg Gly Ile Thr Ala Ile Trp Ile Pro Pro Ala Trp
35 40 45

Lys Gly Thr Ser Gln Asn Asp Val Gly Tyr Gly Ala Tyr Asp Leu Tyr
50 55 60

Asp Leu Gly Glu Phe Asn Gln Lys Gly Thr Val Arg Thr Lys Tyr Gly
65 70 75 80

Thr Arg Ser Gln Leu Glu Ser Ala Ile His Ala Leu Lys Asn Asn Gly
85 90 95

Val Gln Val Tyr Gly Asp Val Val Met Asn His Lys Gly Gly Ala Asp
100 105 110

Ala Thr Glu Asn Val Leu Ala Val Glu Val Asn Pro Asn Asn Arg Asn
115 120 125

Gln Glu Ile Ser Gly Asp Tyr Thr Ile Glu Ala Trp Thr Lys Phe Asp
130 135 140

Phe Pro Gly Arg Gly Asn Thr Tyr Ser Asp Phe Lys Trp Arg Trp Tyr
145 150 155 160

His Phe Asp Gly Val Asp Trp Asp Gln Ser Arg Gln Phe Gln Asn Arg

```
                165                 170                 175
Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
            195                 200                 205

Asp His Pro Glu Val Val Asn Glu Leu Arg Arg Trp Gly Glu Trp Tyr
            210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
            290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
            370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
            450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 30
<211> LENGTH: 485
<212> TYPE: PRT
<213> ORGANISM: Artificial Sequence
<220> FEATURE:
<223> OTHER INFORMATION: Variant of unknown amylase

<400> SEQUENCE: 30

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
                20                  25                  30

Asn Leu Lys Asn Ala Gly Ile Thr Ala Ile Trp Ile Pro Pro Ala Trp
```

```
            35                  40                  45
Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
                100                 105                 110

Phe Thr Glu Arg Val Gln Ala Val Glu Val Asn Pro Gln Asn Arg Asn
                115                 120                 125

Gln Glu Val Ser Gly Thr Tyr Gln Ile Glu Ala Trp Thr Gly Phe Asn
                130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Asp Gly Lys Ala Trp Asp Trp Glu Val Asp
                180                 185                 190

Thr Glu Asn Gly Asn Tyr Asp Tyr Leu Met Tyr Ala Asp Val Asp Met
                195                 200                 205

Asp His Pro Glu Val Ile Asn Glu Leu Asn Arg Trp Gly Val Trp Tyr
210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255

Thr Gly Lys Asn Leu Phe Ala Val Ala Glu Tyr Trp Lys Asn Asp Leu
                260                 265                 270

Gly Ala Leu Glu Asn Tyr Leu Ser Lys Thr Asn Trp Thr Met Ser Ala
                275                 280                 285

Phe Asp Val Pro Leu His Tyr Asn Leu Tyr Gln Ala Ser Asn Ser Ser
290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
                340                 345                 350

Tyr Ala Thr Ile Leu Thr Arg Glu Gln Gly Tyr Pro Gln Val Phe Tyr
                355                 360                 365

Gly Asp Tyr Tyr Gly Ile Pro Ser Asp Gly Val Pro Ser Tyr Arg Gln
                370                 375                 380

Gln Ile Asp Pro Leu Leu Lys Ala Arg Gln Gln Tyr Ala Tyr Gly Thr
385                 390                 395                 400

Gln His Asp Tyr Leu Asp Asn Gln Asp Val Ile Gly Trp Thr Arg Glu
                405                 410                 415

Gly Asp Ser Ala His Ala Gly Ser Gly Leu Ala Thr Val Met Ser Asp
                420                 425                 430

Gly Pro Gly Gly Ser Lys Thr Met Tyr Val Gly Thr Ala His Ala Gly
                435                 440                 445

Gln Val Phe Lys Asp Ile Thr Gly Asn Arg Thr Asp Thr Val Thr Ile
                450                 455                 460
```

```
Asn Ser Ala Gly Asn Gly Thr Phe Pro Cys Asn Gly Gly Ser Val Ser
465                 470                 475                 480

Ile Trp Val Lys Gln
                485

<210> SEQ ID NO 31
<211> LENGTH: 485
<212> TYPE: PRT
<213> ORGANISM: Bacillus sp.

<400> SEQUENCE: 31

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
```

```
                         340                 345                 350
Tyr Ala Leu Thr Leu Thr Arg Glu Gln Gly Tyr Pro Ser Val Phe Tyr
            355                 360                 365
Gly Asp Tyr Tyr Gly Ile Pro Thr His Gly Val Pro Ala Met Lys Ser
        370                 375                 380
Lys Ile Asp Pro Ile Leu Glu Ala Arg Gln Lys Tyr Ala Tyr Gly Arg
385                 390                 395                 400
Gln Asn Asp Tyr Leu Asp His His Asn Ile Ile Gly Trp Thr Arg Glu
                405                 410                 415
Gly Asn Thr Ala His Pro Asn Ser Gly Leu Ala Thr Ile Met Ser Asp
            420                 425                 430
Gly Ala Gly Gly Asn Lys Trp Met Phe Val Gly Arg Asn Lys Ala Gly
        435                 440                 445
Gln Val Trp Thr Asp Ile Thr Gly Asn Arg Ala Gly Thr Val Thr Ile
    450                 455                 460
Asn Ala Asp Gly Trp Gly Asn Phe Ser Val Asn Gly Ser Val Ser
465                 470                 475                 480
Ile Trp Val Asn Lys
            485

<210> SEQ ID NO 32
<211> LENGTH: 214
<212> TYPE: PRT
<213> ORGANISM: Bacillus amyloliquefaciens

<400> SEQUENCE: 32

Gln Thr Gly Gly Ser Phe Phe Glu Pro Phe Asn Ser Tyr Asn Ser Gly
1               5                   10                  15
Leu Trp Gln Lys Ala Asn Gly Tyr Ser Asn Gly Asp Met Phe Asn Cys
            20                  25                  30
Thr Trp Arg Ala Asn Asn Val Ser Met Thr Ser Ser Gly Glu Met Arg
        35                  40                  45
Leu Ala Leu Thr Ser Pro Ser Tyr Asn Lys Phe Asp Cys Gly Glu Asn
    50                  55                  60
Arg Ser Val Gln Thr Tyr Gly Tyr Gly Leu Tyr Glu Val Arg Met Lys
65                  70                  75                  80
Pro Ala Lys Asn Thr Gly Ile Val Ser Ser Phe Phe Thr Tyr Thr Gly
                85                  90                  95
Pro Thr Asp Gly Thr Pro Trp Asp Glu Ile Asp Ile Glu Phe Leu Gly
            100                 105                 110
Lys Asp Thr Thr Lys Val Gln Phe Asn Tyr Tyr Thr Asn Gly Ala Gly
        115                 120                 125
Asn His Glu Lys Val Ala Asp Leu Gly Phe Asp Ala Thr Asn Ala Tyr
    130                 135                 140
His Thr Tyr Ala Phe Asp Trp Gln Pro Asn Ser Ile Lys Trp Tyr Val
145                 150                 155                 160
Asp Gly Gln Leu Lys His Thr Ala Thr Ser Gln Ile Pro Thr Asn Pro
                165                 170                 175
Gly Lys Ile Met Met Asn Leu Trp Asn Gly Ile Gly Val Asp Asp Trp
            180                 185                 190
Leu Gly Ser Tyr Asn Gly Val Asn Pro Leu Tyr Ala His Tyr Asp Trp
        195                 200                 205
Val Arg Tyr Thr Lys Lys
    210
```

<210> SEQ ID NO 33
<211> LENGTH: 214
<212> TYPE: PRT
<213> ORGANISM: Bacillus subtilis

<400> SEQUENCE: 33

Gln Thr Gly Gly Ser Phe Phe Asp Pro Phe Asn Gly Tyr Asn Ser Gly
1               5                   10                  15

Phe Trp Gln Lys Ala Asp Gly Tyr Ser Asn Gly Asn Met Phe Asn Cys
            20                  25                  30

Thr Trp Arg Ala Asn Asn Val Ser Met Thr Ser Leu Gly Glu Met Arg
        35                  40                  45

Leu Ala Leu Thr Ser Pro Ala Tyr Asn Lys Phe Asp Cys Gly Glu Asn
    50                  55                  60

Arg Ser Val Gln Thr Tyr Gly Tyr Gly Leu Tyr Glu Val Arg Met Lys
65                  70                  75                  80

Pro Ala Lys Asn Thr Gly Ile Val Ser Ser Phe Phe Thr Tyr Thr Gly
                85                  90                  95

Pro Thr Asp Gly Thr Pro Trp Asp Glu Ile Asp Ile Glu Phe Leu Gly
            100                 105                 110

Lys Asp Thr Thr Lys Val Gln Phe Asn Tyr Tyr Thr Asn Gly Ala Gly
        115                 120                 125

Asn His Glu Lys Ile Val Asp Leu Gly Phe Asp Ala Ala Asn Ala Tyr
    130                 135                 140

His Thr Tyr Ala Phe Asp Trp Gln Pro Asn Ser Ile Lys Trp Tyr Val
145                 150                 155                 160

Asp Gly Gln Leu Lys His Thr Ala Thr Asn Gln Ile Pro Thr Thr Pro
                165                 170                 175

Gly Lys Ile Met Met Asn Leu Trp Asn Gly Thr Gly Val Asp Glu Trp
            180                 185                 190

Leu Gly Ser Tyr Asn Gly Val Asn Pro Leu Tyr Ala His Tyr Asp Trp
        195                 200                 205

Val Arg Tyr Thr Lys Lys
    210

<210> SEQ ID NO 34
<211> LENGTH: 269
<212> TYPE: PRT
<213> ORGANISM: Bacillus Lentus

<400> SEQUENCE: 34

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 35
<211> LENGTH: 270
<212> TYPE: PRT
<213> ORGANISM: Artificial Sequence
<220> FEATURE:
<223> OTHER INFORMATION: Variant of unknown protease

<400> SEQUENCE: 35

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ala Asp Gly Ser Gly Ser Val Ser Ser Ile Ala Gln Gly Leu Glu Trp
            100                 105                 110

Ala Gly Asn Asn Gly Met His Val Ala Asn Leu Ser Leu Gly Ser Pro
        115                 120                 125

Ser Pro Ser Ala Thr Leu Glu Gln Ala Val Asn Ser Ala Thr Ser Arg
    130                 135                 140

Gly Val Leu Val Val Ala Ala Ser Gly Asn Ser Gly Ala Gly Ser Ile
145                 150                 155                 160

Ser Tyr Pro Ala Arg Tyr Ala Asn Ala Met Ala Val Gly Ala Thr Asp
                165                 170                 175

Gln Asn Asn Asn Arg Ala Ser Phe Ser Gln Tyr Gly Ala Gly Leu Asp
            180                 185                 190

Ile Val Ala Pro Gly Val Asn Val Gln Ser Thr Tyr Pro Gly Ser Thr
        195                 200                 205

Tyr Ala Ser Leu Asn Gly Thr Ser Met Ala Thr Pro His Val Ala Gly
    210                 215                 220
Ala Ala Ala Leu Val Lys Gln Lys Asn Pro Ser Trp Ser Asn Val Gln
225                 230                 235                 240
Ile Arg Asn His Leu Lys Asn Thr Ala Thr Ser Leu Gly Ser Thr Asn
                245                 250                 255
Leu Tyr Gly Ser Gly Leu Val Asn Ala Glu Ala Ala Thr Arg
            260                 265                 270

<210> SEQ ID NO 36
<211> LENGTH: 269
<212> TYPE: PRT
<213> ORGANISM: Artificial Sequence
<220> FEATURE:
<223> OTHER INFORMATION: Variant of unknown protease

<400> SEQUENCE: 36

Ala Gln Ser Val Pro Trp Gly Ile Arg Arg Val Gln Ala Pro Thr Ala
1               5                   10                  15
His Asn Arg Gly Leu Thr Gly Ser Gly Val Lys Val Ala Val Leu Asp
                20                  25                  30
Thr Gly Ile Ser Thr His Pro Asp Leu Asn Ile Arg Gly Gly Ala Ser
            35                  40                  45
Phe Val Pro Gly Glu Pro Ser Thr Gln Asp Gly Asn Gly His Gly Thr
50                  55                  60
His Ala Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Ser Gly Ser Gly Ser Val Ser Ser Ile Ala Gln Gly Leu Glu Trp Ala
            100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Ser Ala Thr Ser Arg Gly
130                 135                 140
Val Leu Val Val Ala Ala Ser Gly Asn Ser Gly Ala Gly Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asp Gly Thr Ser Met Ala Thr Pro His Val Ala Gly Ala
210                 215                 220
Ala Ala Leu Val Lys Gln Lys Asn Pro Ser Trp Ser Asn Val Arg Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265

<210> SEQ ID NO 37
<211> LENGTH: 359
<212> TYPE: PRT
<213> ORGANISM: Artificial Sequence
<220> FEATURE:

<223> OTHER INFORMATION: His-tagged mature protein (Bacillus sp-62449)

<400> SEQUENCE: 37

```
His His His His His Pro Arg Tyr Asn Pro Val Thr Glu Asp Glu
1               5                   10                  15

Leu Tyr His Ser Phe Asp Ser His Asp Ala Arg Asn Trp Gln Ile Ser
            20                  25                  30

Asp Gly Trp Arg Asn Gly Asp Asp Phe Phe Gly Cys His Trp Ser Gln
        35                  40                  45

Asn Arg Val Asn Phe Asn Arg Gly Glu Met Glu Leu Ser Leu Arg Thr
50                  55                  60

Asn Tyr Ser Tyr Ser Ala Pro Tyr Asn Tyr Glu Cys Ala Glu Tyr Ala
65                  70                  75                  80

Thr Ser Asn Phe Tyr Gly Tyr Gly Leu Tyr Glu Val Ser Met Lys Pro
            85                  90                  95

Ala Asn Val Ser Gly Val Ile Ser Ser Phe Phe Thr Tyr Thr Gly Pro
        100                 105                 110

Ser Tyr Asn Gly Ala Pro Trp Asp Glu Ile Asp Ile Glu Phe Leu Gly
    115                 120                 125

Asn Asp Thr Thr Lys Val Gln Phe Asn Tyr Tyr Thr Asn Gly Val Gly
130                 135                 140

Gly Asn Glu Ile Ile Tyr Asp Leu Gly Phe Asp Ala Ala Asn Ser Phe
145                 150                 155                 160

Asn Thr Tyr Ala Phe Asp Trp Gln Glu Asn Tyr Ile Ser Trp Tyr Val
            165                 170                 175

Asn Gly Asn Leu Val Ala Thr Ala Glu Asn Ile Pro Ser Asn Pro
        180                 185                 190

Ser Lys Ile Met Met Asn Val Trp Asn Thr Tyr Gly Ile Asp Glu Trp
    195                 200                 205

Ala Gly Ala Tyr Gly Gly Glu Ala Ala Asn Ala Thr Tyr Glu Trp Val
210                 215                 220

Arg Tyr Thr Pro Asn Asn Gly Asn Thr Thr Pro Ser Thr Ala Pro Asp
225                 230                 235                 240

Phe Gln Leu Gln Ala Cys Asp Tyr Ser Asp Ser Ser Gly Ile Thr Ser
            245                 250                 255

Trp Ser Cys Gly Val Gly Thr Phe His Ser Ser Asn Trp Ile Lys Phe
            260                 265                 270

Asp Ser Val Asp Leu Ser Thr Gly Tyr Asn Ala Phe Ala Val Ser Tyr
        275                 280                 285

Thr Ser Pro Gly Ser Gly Ser Phe Asp Ile Arg Leu Gly Ser Pro His
    290                 295                 300

Gly Gln Arg Ile Gly Thr Val Asn Tyr Gly Ala Thr Gly Gly Trp Ser
305                 310                 315                 320

Asn Tyr Glu Trp Ser Gly Thr Pro Ser Leu Asp Val Thr Val Arg Gly
            325                 330                 335

Ala His Asp Ile Tyr Ile Val Ala Thr Ser Gly Ala Ala Asn Leu Arg
            340                 345                 350

Glu Phe Trp Phe Lys Asn Glu
        355
```

<210> SEQ ID NO 38
<211> LENGTH: 253
<212> TYPE: PRT
<213> ORGANISM: Artificial Sequence
<220> FEATURE:

<223> OTHER INFORMATION: His-tagged mature protein (Bacillus akibai)

<400> SEQUENCE: 38

```
His His His His His Pro Arg Ala Glu Arg Pro Ile Gly Thr Thr
1               5                   10                  15

Phe Val Glu Thr Phe Glu Ser Tyr Asp Ser Glu Arg Trp Ser Lys Ala
            20                  25                  30

Gly Val Trp Thr Asn Gly Gln Met Phe Asn Ala Thr Trp Tyr Pro Glu
        35                  40                  45

Gln Val Thr Phe Ser Asp Gly Lys Met Lys Leu Gln Ile Asp Lys Glu
    50                  55                  60

Asp Asn Glu Thr Ala Ser Pro Pro Tyr Lys Ala Gly Glu Leu Arg Thr
65                  70                  75                  80

Asn Asp Phe Tyr His Tyr Gly Leu Phe Glu Val Ser Met Lys Pro Ala
                85                  90                  95

Lys Ser Thr Gly Thr Val Ser Ser Phe Phe Thr Tyr Thr Gly Pro Trp
            100                 105                 110

Asp Trp Asp Asn Asp Pro Trp Asp Glu Ile Asp Ile Glu Phe Leu Gly
        115                 120                 125

Lys Asp Thr Thr Lys Ile Gln Phe Asn Tyr Phe Thr Asn Gly Val Gly
130                 135                 140

Gly Asn Glu His Tyr His Glu Leu Gly Phe Asp Ala Ala Asp Asp Phe
145                 150                 155                 160

Asn Thr Tyr Ala Phe Glu Trp Arg Pro Glu Ser Ile Arg Trp Phe Val
                165                 170                 175

Asn Gly Glu Leu Val His Thr Ala Thr Glu Asn Ile Pro Gln Thr Pro
            180                 185                 190

Gln Lys Ile Met Met Asn Leu Trp Pro Gly Ile Gly Val Asp Gly Trp
        195                 200                 205

Thr Gly Arg Phe Asn Gly Glu Asp Thr Pro Val Val Thr Gln Tyr Asp
    210                 215                 220

Trp Val Lys Tyr Thr Pro Leu Glu Glu Leu Gly Cys Tyr Asn Glu Lys
225                 230                 235                 240

Asn Asn Lys Tyr Lys Lys Cys Lys Lys Thr Lys Val Lys
                245                 250
```

<210> SEQ ID NO 39
<211> LENGTH: 230
<212> TYPE: PRT
<213> ORGANISM: Artificial Sequence
<220> FEATURE:
<223> OTHER INFORMATION: His-tagged mature protein (Bacillus agaradhaerens)

<400> SEQUENCE: 39

```
His His His His His His Pro Arg His Asn Pro Val Thr Asp Glu Glu
1               5                   10                  15

Val Tyr His Ser Phe Asn Ser His Asp Trp Gln Asn Trp Asn Met Ser
            20                  25                  30

Asp Gly Trp Lys Asn Asp Asp Tyr Phe Phe Gly Cys His Trp Ser Gln
        35                  40                  45

Asn Arg Val Asn Phe Tyr Gly Gly Gln Met Glu Leu Ser Leu Arg Thr
    50                  55                  60

Asn Tyr Ser Tyr Ala Pro Pro Tyr Asn Tyr Glu Cys Ala Glu Tyr Thr
65                  70                  75                  80

Thr Asn Asn Phe Tyr Gly Tyr Gly Leu Tyr Glu Val Ser Met Lys Pro
```

```
                85                  90                  95
Ala Lys Val Ser Gly Val Ile Ser Ser Phe Phe Thr Tyr Thr Gly Pro
                100                 105                 110

Ser Tyr Asn Gly Ala Pro Trp Asp Glu Ile Asp Ile Glu Phe Leu Gly
            115                 120                 125

Asn Asp Thr Thr Lys Val Gln Phe Asn Tyr Tyr Thr Asp Gly Val Gly
        130                 135                 140

Gly Asn Glu Ile Leu Tyr Asp Leu Gly Phe Asp Ala Ala Asp Ser Tyr
145                 150                 155                 160

Asn Thr Tyr Ala Phe Asp Trp Gln Glu Asn Tyr Ile Asn Trp Tyr Val
                165                 170                 175

Asn Gly Gln Leu Val Ala Thr Ala Thr Glu Asn Ile Pro Ser Asn Pro
            180                 185                 190

Ser Lys Ile Met Met Asn Ile Trp Asn Thr Tyr Gly Ile Asp Glu Trp
        195                 200                 205

Ala Gly Arg Tyr Tyr Gly Glu Asp Ala Asn Ala Ser Tyr Asn Trp Val
210                 215                 220

Arg Tyr Thr Pro Asn Arg
225                 230

<210> SEQ ID NO 40
<211> LENGTH: 222
<212> TYPE: PRT
<213> ORGANISM: Artificial Sequence
<220> FEATURE:
<223> OTHER INFORMATION: His-tagged mature protein (Bacillus mojavensis)

<400> SEQUENCE: 40

His His His His His His Pro Arg Gln Thr Gly Gly Ser Phe Phe Asp
1               5                   10                  15

Pro Phe Asn Gly Tyr Asn Ser Gly Phe Trp Gln Lys Ala Asn Gly Tyr
                20                  25                  30

Ser Asn Gly Asn Met Phe Asn Cys Thr Trp Arg Ala Asn Asn Val Ser
            35                  40                  45

Met Thr Ser Leu Gly Glu Met Arg Leu Ala Leu Thr Ser Pro Ser Tyr
        50                  55                  60

Asn Lys Phe Asp Cys Gly Glu Asn Arg Ser Val Gln Thr Tyr Gly Tyr
65                  70                  75                  80

Gly Leu Tyr Glu Val Arg Met Lys Pro Ala Lys Asn Val Gly Ile Val
                85                  90                  95

Ser Ser Phe Phe Thr Tyr Thr Gly Pro Thr Asp Gly Thr Pro Trp Asp
                100                 105                 110

Glu Ile Asp Ile Glu Phe Leu Gly Lys Asp Thr Thr Lys Val Gln Phe
            115                 120                 125

Asn Tyr Tyr Thr Asn Gly Val Gly Asn His Glu Lys Leu Val Asp Leu
        130                 135                 140

Gly Phe Asp Ala Ala Asn Ala Tyr His Thr Tyr Ala Phe Asp Trp Gln
145                 150                 155                 160

Pro Asn Ser Ile Lys Trp Tyr Val Asp Gly Gln Leu Lys His Thr Ala
                165                 170                 175

Thr Ser Gln Ile Pro Thr Thr Pro Gly Lys Ile Met Met Asn Leu Trp
            180                 185                 190
```

```
Asn Gly Thr Gly Val Asp Glu Trp Leu Gly Ser Tyr Asn Gly Val Thr
        195                 200                 205
Pro Leu Tyr Ala His Tyr Asp Trp Val Arg Tyr Thr Lys Lys
    210                 215                 220
```

POLYPEPTIDES HAVING BETA-GLUCANASE ACTIVITY, POLYNUCLEOTIDES ENCODING SAME AND USES THEREOF IN CLEANING AND DETERGENT COMPOSITIONS

CROSS-REFERENCE TO RELATED APPLICATIONS

This application is a 35 U.S.C. 371 national application of PCT/EP2016/080157 filed Dec. 7, 2016, which claims priority or the benefit under 35 U.S.C. 119 of European application no. 15198277.4 filed on Dec. 7, 2015, and of European application no. 15198282.4 filed on Dec. 7, 2015, the contents of which are fully incorporated herein by reference.

REFERENCE TO A SEQUENCE LISTING

This application contains a Sequence Listing in computer readable form, which is incorporated herein by reference.

REFERENCE TO A JOINT RESEARCH AGREEMENT

The embodiments claimed in the present application were made under a joint research agreement between Henkel AG & Co. KGaA and Novozymes A/S.

BACKGROUND OF THE INVENTION

Field of the Invention

The present invention relates to cleaning or detergent compositions comprising polypeptides exhibiting beta-glucanase activity and one or more amylases and/or one or more proteases and uses thereof in cleaning or detergent applications and processes such as cleaning hard-surfaces, dish wash and laundering. The present invention further relates to polypeptides having beta-glucanase activity and polynucleotides encoding the polypeptides. The invention also relates to nucleic acid constructs, vectors, and host cells comprising the polynucleotides as well as methods of producing and using the polypeptides, e.g. in cleaning or detergent applications and processes such as cleaning hard-surfaces, dish wash and laundering.

Description of the Related Art

Beta-glucans are polysaccharides consisting of glucose units linked by beta-glycosidic bonds. Cellulose is one type of beta-glucan, in which all of the glucose units are linked by beta-1,4-glucosidic bonds. This feature results in the formation of insoluble cellulose micro-fibrils. Enzymatic hydrolysis of cellulose to glucose requires the use of endo beta-glucanases (e.g. EC 3.2.1.4), cellobiohydrolases (e.g. EC 3.2.1.91) and beta-glucosidases (e.g. EC 3.2.1.21).

Beta-glucans can also be linked by beta-1,3-glucosidic bonds (e.g., as found in the cell walls of baker's yeast, *Saccharomyces cerevisiae*), beta-1,6-glucosidic bonds as well as combinations of beta-1,3-, beta-1,4- and beta-1,6-glucosidic bonds. The combination of beta-1,3- and beta-1,4-glucosidic bonds can be found, e.g. in the soluble fibre from cereals such as oats and barley. A subgroup of beta-glucanases, also known as a licheninases (or lichenases) (EC 3.2.1.73), can be used to catalyse the hydrolysis of the beta-1,4-glucosidic bonds to give beta-glucans. Licheninases (or lichenases) (e.g. EC 3.2.1.73) hydrolyse (1,4)-beta-D-glucosidic linkages in beta-D-glucans containing (1,3)— and (1,4)-bonds and can act on lichenin and cereal beta-D-glucans, but not on beta-D-glucans containing only 1,3- or 1,4-bonds. Other beta-glucanases (e.g. EC 3.2.1.4) can, for example, perform endohydrolysis of (1,4)-beta-D-glucosidic linkages in cellulose, lichenin and cereal beta-D-glucans and will also hydrolyze 1,4-linkages in beta-D-glucans containing 1,3-linkages.

The removal of cereal stains as oat and barley containing stains in dish wash and laundry is a recognised problem, and there is a considerable interest in finding enzymes that can degrade the beta-glucans found therein. Various *Bacillus* species like e.g. *B. amyloliquefaciens* express a beta-glucanase, but these enzymes are generally not very suitable for alkaline applications, e.g. at pH 7.5 or above.

The present invention provides polypeptides of glycoside hydrolase family 16 (GH16) having beta-glucanase activity (e.g. comprising or consisting of licheninase (EC 3.2.1.73) activity) and polynucleotides encoding said polypeptides, which are highly active in degrading different types of beta-glucans (e.g. beta-D-glucans, beta-1,3-1,4 glucans, mix-linkage beta-glucans, barley beta-glucans and oatmeal beta-glucans), e.g. under alkaline conditions (e.g. at pH 7.5 or above), and therefore could be used in the aforementioned applications, e.g. in cleaning or detergent applications and processes such as cleaning hard-surfaces, dish wash and laundering. The existing products comprising beta-glucanases have very low effect on this type of beta-glucan as their main enzymatic substrate is cellulose. Therefore, the present invention provides novel beta-glucanases with improved properties (e.g. with significant improvement of performance and/or stability under alkaline conditions; beta-glucanases without cellulase activity (e.g. not having endo-cellulase activity on β-1,4 linkages between D-glucose units) (e.g. EC 3.2.1.73). A difference between use of cellulases and lichenases on textile in laundry is that the lichenases do not degrade the fibers of the textile.

Furthermore, some particular solid detergents have pH above 10. The known beta-glucanases are not suitable for these very high pH detergents. Thus, for example, known beta-glucanases from *Bacillus amyloliquefaciens* and *Bacillus subtilis* quickly lose their activity under alkaline conditions as has been demonstrated in Example 8 herein. The present invention provides novel beta-glucanases with improved properties (e.g. with significant improvement of performance and/or stability under alkaline conditions).

An uncharacterized protein from *Bacillus halodurans* (uniprot:Q9K7X6) is 88.4% identical to the beta-glucanase shown in SEQ ID NO: 7.

An uncharacterized protein from *Bacillus cellulosilyticus* (uniprot:E6TRB0) is 80.7% identical to the beta-glucanase shown in SEQ ID NO: 3.

An uncharacterized protein from *Bacillus akibai* (uniprot: W4QVK7) is 98.2% identical to the beta-glucanase shown in SEQ ID NO: 5.

An uncharacterized protein from *Bacillus subtilis* subsp. *niger*. (uniprot:AOA080UVP7) is 97.9% identical to the beta-glucanase shown in SEQ ID NO: 9.

SUMMARY OF THE INVENTION

In one aspect, the present invention relates to a cleaning or detergent composition comprising a polypeptide(s) having beta-glucanase activity, selected from the group consisting of:

(a) a polypeptide having at least 60% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having at least 60% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity; wherein said cleaning or detergent composition further comprising:

(i) one or more amylases; and/or (ii) one or more proteases, preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than 6.5 at about 40° C. for about 30 minutes at pH of about 7.5, further most preferably said REM synergistic effect is of more than 6.1 at about 40° C. for about 30 minutes at pH of about 10, further most preferably said REM synergistic effect is of more than 6.2 at about 40° C. for about 30 minutes at pH of about 10, further most preferably said beta-glucanase activity is not an endo-cellulase activity on β-1,4 linkages between D-glucose units of cellulose.

In another aspect, the present invention relates to a cleaning or detergent composition comprising a polypeptide(s) having beta-glucanase activity, selected from the group consisting of:

(a) a polypeptide having at least 81% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having at least 81% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity; wherein said cleaning or detergent composition further comprising:

(i) one or more amylases; and/or (ii) one or more proteases, preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than 6.5 at about 40° C. for about 30 minutes at pH of about 7.5, further most preferably said REM synergistic effect is of more than 6.1 at about 40° C. for about 30 minutes at pH of about 10, further most preferably said REM synergistic effect is of more than 6.2 at about 40° C. for about 30 minutes at pH of about 10, further most preferably said beta-glucanase activity is not an endo-cellulase activity on β-1,4 linkages between D-glucose units of cellulose.

In another aspect, the present invention relates to a cleaning or detergent composition comprising a polypeptide(s) having beta-glucanase activity, selected from the group consisting of:

(a) a polypeptide having at least 99% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having at least 99% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity; wherein said cleaning or detergent composition further comprising:

(i) one or more amylases; and/or (ii) one or more proteases, preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than 6.5 at about 40° C. for about 30 minutes at pH of about 7.5, further most preferably said REM synergistic effect is of more than 6.1 at about 40° C. for about 30 minutes at pH of about 10, further most preferably said REM synergistic effect is of more than 6.2 at about 40° C. for about 30 minutes at pH of about 10, further most preferably said beta-glucanase activity is not an endo-cellulase activity on β-1,4 linkages between D-glucose units of cellulose.

In another aspect, the present invention relates to a cleaning or detergent composition comprising a polypeptide(s) having beta-glucanase activity, selected from the group consisting of:

(a) a polypeptide having at least 89% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having at least 89% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity; wherein said cleaning or detergent composition further comprising:

(i) one or more amylases; and/or (ii) one or more proteases, preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than 6.5 at about 40° C. for about 30 minutes at pH of about 7.5, further most preferably said REM synergistic effect is of more than 6.1 at about 40° C. for about 30 minutes at pH of about 10, further most preferably said REM synergistic effect is of more than 6.2 at about 40° C. for about 30 minutes at pH of about 10, further most preferably said beta-glucanase activity is not an endo-cellulase activity on β-1,4 linkages between D-glucose units of cellulose.

In another aspect, the present invention relates to a cleaning or detergent composition comprising a polypeptide(s) having beta-glucanase activity, selected from the group consisting of:

(a) a polypeptide having at least 98% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having at least 98% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity; wherein said cleaning or detergent composition further comprising:

(i) one or more amylases; and/or (ii) one or more proteases, preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than 6.5 at about 40° C. for about 30 minutes at pH of about 7.5, further most preferably said REM synergistic effect is of more than 6.1 at about 40° C. for about 30 minutes at pH of about 10, further most preferably said REM synergistic effect is of more than 6.2 at about 40° C. for about 30 minutes at pH of about 10, further most preferably said beta-glucanase activity is not an endo-cellulase activity on β-1,4 linkages between D-glucose units of cellulose.

In another aspect, the present invention relates to a cleaning or detergent composition comprising a polypeptide(s) having beta-glucanase activity, selected from the group consisting of:

(a) a polypeptide having 100% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having 100% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity; wherein said cleaning or detergent composition further comprising:

(i) one or more amylases; and/or (ii) one or more proteases, preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than 6.5 at about 40° C. for about 30 minutes at pH of about 7.5, further most preferably said REM synergistic effect is of more than 6.1 at about 40° C. for about 30 minutes at pH of about 10, further most preferably said REM synergistic effect is of more than 6.2 at about 40° C. for about 30 minutes at pH of about 10, further most preferably said beta-glucanase activity is not an endo-cellulase activity on β-1,4 linkages between D-glucose units of cellulose.

In another aspect, the present invention relates to a cleaning or detergent composition comprising a beta-glucanase of the invention together with one or more alpha-amylases (and/or said one or more proteases). In another aspect, the present invention relates to a cleaning or detergent composition comprising a beta-glucanase together with one or more amylases and one or more further enzymes selected from the group comprising of proteases, lipases, cutinases, cellulases, endoglucanases, xyloglucanases, pectinases, pectin lyases, xanthanases, peroxidaes, haloperoxygenases, catalases, mannanases, or any mixture thereof. In another aspect, the present invention relates to a cleaning or detergent composition of the invention having an enzyme detergency benefit or improved wash performance in cleaning or detergent applications.

In another aspect, the present invention relates to use of a beta-glucanase of the invention together with one or more proteases, and optionally one or more further enzymes such as proteases, lipases, cutinases, cellulases, endoglucanases, xyloglucanases, pectinases, pectin lyases, xanthanases, peroxidaes, haloperoxygenases, catalases, mannanases, or any mixture thereof, for dish wash or laundering.

In another aspect, the present invention relates to a polypeptide(s) having beta-glucanase activity and polynucleotides encoding the polypeptides. In another aspect, the present invention relates to polypeptides having beta-glucanase activity with improved wash performance and/or improved stability at alkaline conditions (e.g. at pH 7.5 or above). In another aspect, the present invention relates to polypeptides having beta-glucanase activity selected from the group consisting of:

(a) a polypeptide having at least 60% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having at least 60% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity.

In another aspect, the present invention relates to polypeptides having beta-glucanase activity selected from the group consisting of:

(a) a polypeptide having at least 81% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having at least 81% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity.

In another aspect, the present invention relates to polypeptides having beta-glucanase activity selected from the group consisting of:

(a) a polypeptide having at least 99% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having at least 99% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity. The present invention further relates to polypeptides having beta-glucanase activity selected from the group consisting of:

(a) a polypeptide having at least 89% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having at least 89% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity. In another aspect, the present invention relates to polypeptides having beta-glucanase activity selected from the group consisting of:

(a) a polypeptide having at least 98% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having at least 98% sequence identity to the mature polypeptide coding sequence of the sequence selected from the group consisting of SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity.

In another aspect, the present invention relates to polypeptides having beta-glucanase activity selected from the group consisting of:

(a) a polypeptide having at least 100% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;

(b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);

(c) a polypeptide encoded by a polynucleotide having at least 100% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity.

In another aspect, the present invention relates to compositions comprising the polypeptide of the present invention and the use of polypeptides of the present invention in degrading a beta-glucan (e.g. beta-D-glucan, beta-1,3-1,4 glucan, a mix-linkage beta-glucan, barley beta-glucan, oatmeal beta-glucan), controlling the viscosity of fluids (e.g. drilling fluids), for washing or cleaning a textile and/or a hard surface; methods for degrading beta-glucan comprising applying a composition comprising the polypeptide of the present invention to the beta-glucan.

In another aspect, the present invention relates to a difference between the use of cellulases and lichenases of the present invention on textile in laundry is that the lichenases of the present invention do not degrade the fibers of the textile.

In another aspect, the present invention relates to methods of laundering fabrics or textiles or hard surface cleaning including automated dish wash (ADW) and hand dish wash (HDW) using a polypeptide(s) or a composition (e.g. cleaning or detergent composition) of the invention. In another aspect, the present invention relates to detergent compositions comprising a polypeptide(s) of the invention. In another aspect, the present invention relates to a cleaning or detergent composition comprising said beta-glucanase polypeptide of the invention and one or more amylases (and/or said one or more proteases).

In another aspect, the present invention relates to polynucleotides encoding the polypeptides of the present invention; nucleic acid constructs; recombinant expression vectors; recombinant host cells comprising the polynucleotides; and methods of producing the polypeptides.

In another aspect, the present invention relates to fermentation broth formulations or cell culture compositions comprising the polypeptides of the present invention.

In another aspect, the present invention relates to use of a polypeptide(s) of the present invention for preventing, reducing or removing a biofilm from an item.

In another aspect, the present invention relates to use of a polypeptide(s) or detergent composition of the invention for reducing or preventing soil redeposition.

Overview of Sequence Listing

SEQ ID NO: 1 is the DNA sequence of the beta-glucanase as isolated from a strain of a *Bacillus* sp.

SEQ ID NO: 2 is the amino acid sequence of the beta-glucanase as automatically deduced from SEQ ID NO: 1.

SEQ ID NO: 3 is the amino acid sequence of the beta-glucanase as deduced from SEQ ID NO: 1 taking into account that the first amino acid (position −28) in the polypeptide shown in SEQ ID NO: 2 and encoded by the polynucleotide shown in SEQ ID NO:1 should be Met, not Val. When the first codon is gtg a Met is inserted though gtg normally codes for V.

SEQ ID NO: 4 is the DNA sequence of the beta-glucanase as isolated from a strain of a *Bacillus akibai*.

SEQ ID NO: 5 is the amino acid sequence of the beta-glucanase as deduced from SEQ ID NO: 4.

SEQ ID NO: 6 is the DNA sequence of the beta-glucanase as isolated from a strain of a *Bacillus agaradhaerens*.

SEQ ID NO: 7 is the amino acid sequence of the beta-glucanase as deduced from SEQ ID NO: 6.

SEQ ID NO: 8 is the DNA sequence of the beta-glucanase as isolated from a strain of a *Bacillus mojavensis*.

SEQ ID NO: 9 is the amino acid sequence of the beta-glucanase as deduced from SEQ ID NO: 8.

SEQ ID NO: 10 is a polypeptide secretion signal *Bacillus clausii*.

SEQ ID NO: 11 is an artificial N-terminal poly-histidine affinity purification tag sequence.

SEQ ID NO: 12 is alpha-amylase protein sequence from *Bacillus* sp. (Stainzyme).

SEQ ID NO: 13 is a polypeptide corresponding to SEQ ID NO: 2 of WO 95/10603.

SEQ ID NO: 14 is a polypeptide corresponding to SEQ ID NO: 6 in WO 02/010355.

SEQ ID NO: 15 is a polypeptide corresponding to a hybrid polypeptide comprising residues 1-33 of SEQ ID NO: 6 of WO 2006/066594 and residues 36-483 of SEQ ID NO: 4 of WO 2006/066594.

SEQ ID NO: 16 is a polypeptide corresponding to SEQ ID NO: 6 of WO 02/019467.

SEQ ID NO: 17, SEQ ID NO: 18 and SEQ ID NO: 19 are polypeptides respectively corresponding to SEQ ID NO: 1, SEQ ID NO: 2 or SEQ ID NO: 7 of WO 96/023873.

SEQ ID NO: 20 is a polypeptide corresponding to SEQ ID NO: 2 of WO 08/153815 SEQ ID NO: 21 is a polypeptide corresponding to SEQ ID NO: 10 of WO 01/66712.

SEQ ID NO: 22 is a polypeptide corresponding to SEQ ID NO: 2 of WO 09/061380.

SEQ ID NO: 23 is an amylase protein sequence from *Bacillus* sp.

SEQ ID NO: 24 is an amylase protein sequence from *Bacillus* sp.

SEQ ID NO: 25 is an amylase protein sequence from *Bacillus* sp.

SEQ ID NO: 26 is an amylase protein sequence from *Cytophaga* sp.

SEQ ID NO: 27 is an amylase protein sequence from *Bacillus* sp.

SEQ ID NO: 28 is an amylase protein sequence from *Bacillus* sp.

SEQ ID NO: 29 is an amylase protein sequence from *Bacillus halmapalus*.

SEQ ID NO: 30 is an artificial amylase protein sequence.

SEQ ID NO: 31 is an amylase protein sequence from *Bacillus* sp.

SEQ ID NO: 32 is a beta-glucanase protein sequence from *Bacillus amyloliquefaciens*.

SEQ ID NO: 33 is a beta-glucanase protein sequence from *Bacillus subtilis*.

SEQ ID NO: 34 is a protease protein sequence from *Bacillus Lentus*.

SEQ ID NO: 35 is an artificial protease protein sequence.

SEQ ID NO: 36 is an artificial protease protein sequence.

SEQ ID NO: 37 is His-tagged recombinant mature beta-glucanase protein from *Bacillus* sp-62449.

SEQ ID NO: 38 is His-tagged recombinant mature beta-glucanase protein from *Bacillus akibai*.

SEQ ID NO: 39 is His-tagged recombinant mature beta-glucanase protein from *Bacillus agaradhaerens*.

SEQ ID NO: 40 is His-tagged recombinant mature beta-glucanase protein from *Bacillus mojavensis*.

Definitions

Anti-redeposition: The term "anti-redeposition" or "anti-redeposition effect" means the reduction or prevention of soil from depositing back onto the textile, fabric or hard surface. The anti-redeposition effect can be determined using the Mini-LOM or Mini-TOM wash assay as described in the examples herein (e.g., as in example 14).

Synergistic effect: The term "synergistic effect" means a cooperative action of polypeptides such that a total combined effect of said polypeptides is greater than the sum of the individual enzymatic effects of said polypeptides. Non-limiting examples of synergistic effect include REM synergistic effect of a beta-glucanase polypeptide of the invention and one or more alpha-amylase (and/or one or more proteases).

REM synergistic effect: REM synergistic effect of polypeptides as used herein can be measured based on the analysis of stain removal carried out by using any suitable wash performance methodology (e.g. Wascator bottle wash method). A preferred method for determining the REM synergistic effect is disclosed in Examples disclosed herein, e.g., Example 7.

Beta-glucanase: The term "beta-glucanase" as used herein means an endo beta-1,4-glucanase activity (e.g. endo-1,4-β-D-glucanase) that catalyzes the hydrolyses of a beta-1,4-bonds connecting two glucosyl residues in a beta-glucan. Non-limiting examples of beta-glucanases as defined herein include cellulases (e.g. EC 3.2.1.4, e.g. having endo-cellulase activity on β-1,4 linkages between D-glucose units and licheninases (or lichenases) (e.g. EC 3.2.1.73) hydrolysing (1,4)-beta-D-glucosidic linkages in beta-D-glucans containing (1,3)—and (1,4)-bonds. Beta-glucanases (e.g. EC 3.2.1.4) can, for example, perform endohydrolysis of (1,4)-beta-D-glucosidic linkages in cellulose, lichenin and cereal beta-D-glucans and will also hydrolyze 1,4-linkages in beta-D-glucans containing 1,3-linkages. For purposes of the present invention, beta-glucanase activity is determined according to the procedure described in the Examples. In one aspect of the invention, the polypeptides of the present invention have at least 20%, e.g., at least 40%, at least 50%, at least 60%, at least 70%, at least 80%, at least 90%, at least 95%, or at least 100% of the beta-glucanase activity of the polypeptide having the sequence selected from the group consisting of: SEQ ID NO: 7, SEQ ID NO: 2, SEQ ID NO: 3, SEQ ID NO: 5, SEQ ID NO: 9. Beta-glucanase activity can suitably be measured using barley beta-glucan as substrate. A preferred assay for determining beta-glucanase activity is disclosed in Example 1 (AZCL-Barley beta-glucan assay). A further subgroup of beta-glucanases as defined herein, also known as a licheninases (or lichenases) (e.g. EC 3.2.1.73), can also be used to catalyse the hydrolysis of the beta-1,4-glucosidic bonds to give beta-glucans. Licheninases (or lichenases) (e.g. EC 3.2.1.73) hydrolyse (1,4)-beta-D-glucosidic linkages in beta-D-glucans containing (1,3)- and (1,4)-bonds and can act on lichenin and cereal beta-D-glucans, but not on beta-D-glucans containing only 1,3- or 1,4-bonds. As used herein the term "beta-glucanase activity" comprises licheninase (or lichenases) (e.g. EC 3.2.1.73) activity.

Beta-glucan: The term "beta-glucan" as used herein means a polysaccharide that only contain glucose as structural components, and in which the glucose units are linked by beta-glycosidic bonds. Non-limiting examples of beta-glucans include beta-D-glucans, beta-1,3-1,4 glucans, mix-linkage beta-glucans, barley beta-glucans, oatmeal beta-glucans.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: The term "biofilm" means any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from free-floating bacteria of the same species, as the dense and protected environment of the film allows them to cooperate and interact in various ways. One effect of this environment is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp.

Carbohydrate binding module: The term "carbohydrate binding module" means the region within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellulolytic enzyme or cellulase: The term "cellulolytic enzyme" or "cellulase" means one or more (e.g., several) enzymes that hydrolyze a cellulosic material. Such enzymes include endoglucanase(s) (e.g. EC 3.2.1.4), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No. filter paper, microcrystalline cellulose, bacterial cellulose, algal cellulose, cotton, pretreated lignocellulose, etc. The most common total cellulolytic activity assay is the filter paper assay using Whatman No. filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.–80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is arundo, bagasse, bamboo, corn cob, corn fiber, corn stover, miscanthus, rice straw, switchgrass, or wheat straw.

In another embodiment, the cellulosic material is aspen, eucalyptus, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Detergent component: the term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

Detergent composition: the term "detergent composition" refers to compositions that find use in the removal of undesired compounds from items to be cleaned, such as textiles, dishes, and hard surfaces. The detergent composition may be used to e.g. clean textiles, dishes and hard surfaces for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; hard surface cleaning formulations, such as for glass, wood, plastic, ceramic and metal counter tops and windows; carpet cleaners; oven cleaners; fabric fresheners; fabric softeners; and textile and laundry pre-spotters, as well as dish wash detergents). In addition to containing a GH16 beta-glucanase of the invention, the detergent formulation may contain one or more additional enzymes (such as amylases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, and combinations thereof, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti corrosion agents, enzyme inhibitors or stabilizers, enzyme activators, transferase(s), hydrolytic enzymes, oxido reductases, bluing agents and fluorescent dyes, antioxidants, and solubilizers.

Dish wash: The term "dish wash" refers to all forms of washing dishes, e.g. by hand dish wash (HDW) or automatic dish wash (ADW). Washing dishes includes, but is not limited to, the cleaning of all forms of crockery such as plates, cups, glasses, bowls, all forms of cutlery such as spoons, knives, forks and serving utensils as well as ceramics, plastics, metals, china, glass and acrylics.

Dish washing composition: The term "dish washing composition" refers to all forms of compositions for cleaning hard surfaces. The present invention is not restricted to any particular type of dish wash composition or any particular detergent.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic or carbohydrate binding module having one or more (e.g., several) amino acids absent from the amino and/or carboxyl terminus of a mature polypeptide or domain; wherein the fragment has beta-glucanase or carbohydrate binding activity. In one aspect, a fragment contains at least 340 amino acid residues, or at least 230 amino acid residues, or at least 210 amino acid residues or at least 200 amino acid residues, or at least 180 amino acid residues, wherein the fragment has beta-glucanase activity.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics, metals, china, glass and acrylics.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, *Current Opinion In Microbiology,* 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.–80° C., e.g., 50° C., 55° C., 60° C., 65° C., or 70° C., and a suitable pH such as 4-9, e.g., 5.0, 5.5, 6.0, 6.5, or 7.0.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication, as well as a recombinant host cell, an isolated host cell (e.g., an isolated recombinant host cell), an isolated host cell that is not a human embryonic stem cell. In preferred embodiments of the invention a recombinant host cell is a heterologous recombinant host cell (e.g., a host cell that is not a *Bacillus agaradhaerens* host cell, or a host cell that is not a *Bacillus* sp-62449 host cell, or a host cell that is not a *Bacillus akibai* host cell, or a host cell that is not a *Bacillus mojavensis* host cell).

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). A fermentation broth produced by culturing a recombinant host cell expressing the polynucleotide of the invention will comprise the polypeptide of the invention in an isolated form.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Lichenase activity: The term "lichenase activity" means enzymes that hydrolysis beta-1,3, beta-1,4-glucans (e.g. EC 3.2.1.73).

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is selected from the group consisting of: amino acids 1 to 222 of SEQ ID NO: 7, amino acids 1 to 351 of SEQ ID NO: 2, amino acids 1 to 351 of SEQ ID NO: 3, amino acids 1 to 245 of SEQ ID NO: 5, amino acids 1 to 214 of SEQ ID NO: 9. The amino acids −28 to −1 of SEQ ID NO: 2 are a signal peptide. The amino acids −28 to −1 of SEQ ID NO: 3 are a signal peptide. The amino acids −31 to −1 of SEQ ID NO: 5 are a signal peptide. The amino acids −15 to −1 of SEQ ID NO: 7 are a signal peptide. The amino acids −29 to −1 of SEQ ID NO: 9 are a signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having beta-glucanase activity. In one aspect, the mature polypeptide coding sequence is selected from the group consisting of: nucleotides 85 to 1137 of SEQ ID NO: 1, nucleotides 94 to 828 of SEQ ID NO: 4, nucleotides 46 to 711 of SEQ ID NO: 6, nucleotides 88 to 729 of SEQ ID NO: 8. The nucleotides 1 to 84 of SEQ ID NO: 1 encode a signal peptide. The nucleotides 1 to 93 of SEQ ID NO: 4 encode a signal peptide. The nucleotides 1 to 45 of SEQ ID NO: 6 encode a signal peptide. The nucleotides 1 to 87 of SEQ ID NO: 8 encode a signal peptide.

Malodor: The term "malodor" means an odor which is not desired on clean items. The cleaned item should smell fresh and clean without malodors adhered to the item. One example of malodor is compounds with an unpleasant smell, which may be produced by microorganisms. Another example is sweat or body odor adhered to an item which has been in contact with humans or animals. Another example of malodor can be the smell from spices, for example curry or other exotic spices adhering to an item such as a piece of textile. One way of measuring the ability of an item to adhere malodor is by using the Malodor Assay.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence Identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the —nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the —nobrief option) is used as the percent identity and is calculated as follows:

(Identical Deoxyribonucleotides×100)/(Length of Alignment−Total Number of Gaps in Alignment)

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 1.6×SSC, 0.2% SDS at 60° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.8×SSC, 0.2% SDS at 60° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.8×SSC, 0.2% SDS at 65° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.4×SSC, 0.2% SDS at 65° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having beta-glucanase activity. In one aspect, a subsequence contains at least 1052 nucleotides of SEQ ID NO: 1 or the cDNA sequence thereof, at least 1037 nucleotides of SEQ ID NO: 1 or the cDNA sequence thereof, or 1022 nucleotides of SEQ ID NO: 1 or the cDNA sequence thereof).

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used it is intended to include the broader term textiles as well.

Variant: The term "variant" means a polypeptide having beta-glucanase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. The variants of the present invention have at least 20%, e.g., at least 40%, at least 50%, at least 60%, at least 70%, at least 80%, at least 90%, at least 95%, or at least 100% of the beta-glucanase activity of the polypeptide of sequence selected from the group consisting of: SEQ ID NO: 7, SEQ ID NO: 2, SEQ ID NO: 3, SEQ ID NO: 5, SEQ ID NO: 9 or the mature polypeptide of sequence selected from the group consisting of: SEQ ID NO: 7, SEQ ID NO: 2, SEQ ID NO: 3, SEQ ID NO: 5, SEQ ID NO: 9.

Wild-type beta-glucanase: The term "wild-type" beta-glucanase means a beta-glucanase expressed by a naturally occurring microorganism, such as a bacterium, yeast, or filamentous fungus found in nature.

Wash performance: The term "wash performance" is defined herein as the ability of an enzyme or a blend of enzymes to remove stains present on an object to be cleaned during e.g. wash or hard surface cleaning relative to the wash performance without one or more on the enzymes present.

DETAILED DESCRIPTION OF THE INVENTION

Polypeptides Having Beta-Glucanase Activity

This invention provides the use of novel beta-glucanases and one or more amylases (and/or one or more proteases) for cleaning or detergent compositions which have a benefit in removing stains and which can be used in cleaning or detergent applications or for processes such as cleaning hard-surfaces, dish wash and laundering. The invention also provides the use of beta-glucanases that are wash stable in detergent formulations in the presence of amylases. The beta-glucanases of the invention may show synergistic effect with one or more amylases (and/or one or more proteases)

(e.g. wherein a preferred method for determining the REM synergistic effect is disclosed in Examples disclosed herein, e.g., Example 7).

In an embodiment, the present invention relates to a cleaning or detergent composition comprising a polypeptide(s) having beta-glucanase activity, wherein said polypeptides having a sequence identity to the mature polypeptide of the sequence selected from the group consisting of: SEQ ID NO: 2, SEQ ID NO: 3, SEQ ID NO: 5, SEQ ID NO: 7, SEQ ID NO: 9; at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have beta-glucanase activity; and one or more amylases (and/or one or more proteases), preferably said polypeptide having beta-glucanase activity and said one or more amylases (and/or one or more proteases) have a synergistic effect; further preferably said synergistic effect is a REM synergistic effect, further most preferably said REM synergistic effect is of more than 6.5 at about 40° C. for about 30 minutes at pH of about 7.5, further most preferably said REM synergistic effect is of more than 6.1 at about 40° C. for about 30 minutes at pH of about 10, further most preferably said REM synergistic effect is of more than 6.2 at about 40° C. for about 30 minutes at pH of about 10, further most preferably said beta-glucanase activity is not an endo-cellulase activity on 3-1,4 linkages between D-glucose units of cellulose.

In an embodiment, the present invention relates to polypeptides having a sequence identity to the mature polypeptide of the sequence selected from the group consisting of: SEQ ID NO: 2, SEQ ID NO: 3, SEQ ID NO: 5, SEQ ID NO: 7, SEQ ID NO: 9; at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have beta-glucanase activity. An embodiment of the present invention is a composition (e.g. a cleaning or detergent composition) comprising said beta-glucanase polypeptide(s) and one or more amylases (and/or one or more proteases).

In one aspect, the polypeptides differ by up to 10 amino acids, e.g., 1, 2, 3, 4, 5, 6, 7, 8, 9, or 10, from the mature polypeptide of sequence selected from the group consisting of: SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In an embodiment, the polypeptides have at least 81% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 81% identity to the mature polypeptide of sequence selected from the group consisting of SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 82% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 82% identity to the mature polypeptide of sequence selected from the group consisting of SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 83% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 83% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 84% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 84% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 85% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 85% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 86% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 86% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 87% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 87% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 88% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 88% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 89% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 89% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 90% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 90% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 91% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 91% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 92% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 92% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 93% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 93% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 94% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 94% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 95% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 95% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 96% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 96% identity to the mature polypeptide of sequence selected from the group consisting of SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 97% identity to the mature polypeptide of sequence selected from the group consisting of: SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 97% identity to the mature polypeptide of sequence selected from the group consisting of SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 98% identity to the mature polypeptide of sequence selected from the group consisting of: SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 98% identity to the mature polypeptide of sequence selected from the group consisting of: SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have at least 99% identity to the mature polypeptide of sequence selected from the group consisting of SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having at least 99% identity to the mature polypeptide of sequence selected from the group consisting of SEQ ID NO: 2, SEQ ID NO: 3, SEQ ID NO: 5, SEQ ID NO: 7, SEQ ID NO: 9 and one or more amylases (and/or one or more proteases).

In an embodiment, the polypeptides have 100% identity to the mature polypeptide of sequence selected from the group consisting of: SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In one embodiment, the present invention relates to a cleaning or detergent composition comprising a beta-glucanase having 100% identity to the mature polypeptide of sequence selected from the group consisting of SEQ ID NO: 2, SEQ ID NO: 3, SEQ ID NO: 5, SEQ ID NO: 7, SEQ ID NO: 9 and one or more amylases (and/or one or more proteases).

In another embodiment a polypeptide(s) having beta-glucanase activity and one or more amylases (and/or one or more proteases) have a synergistic effect; preferably said synergistic effect is a REM synergistic effect, further preferably said REM synergistic effect is of more than 6.5 at about 40° C. for about 30 minutes at pH of about 7.5, further preferably said REM synergistic effect is of more than 6.1 at about 40° C. for about 30 minutes at pH of about 10, further preferably said REM synergistic effect is of more than 6.2 at about 40° C. for about 30 minutes at pH of about 10, further preferably said beta-glucanase activity is not an endo-cellulase activity on β-1,4 linkages between D-glucose units of cellulose.

In another embodiment REM synergistic effect is of more than 1.4 (such as 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0) at about 40° C. (or 35° C., 45° C., 50° C., 55° C., 60° C.) for about 30 minutes (or 15 min, 20 min, 25 min, 35 min, 40 min) at pH of about 7.0 (or 7.5, 8.0, 8.5, 9.0, 9.5, 10.0, 10.5, 11.0, 11.5, 12.0, 12.5, 13.0, 13.5), e.g. in Wascator bottle wash in Model detergent A1 at 40° C., 30 min (pH 7.7), or Wascator bottle wash in Model detergent X1 at 40° C., 30 min (pH 10.1), or Wascator bottle wash in ADW Model detergent A1 at 40° C., 30 min (pH 10.2) (e.g. see Example 7).

In another embodiment a pH optimum of a polypeptide(s) of the present invention is selected in the range from about 6 to about 9. In another embodiment a pH optimum of a polypeptide(s) of the present invention is selected from the group consisting of: 6, 6.5, 7, 7.5, 8, 8.5, 9. In another embodiment a pH optimum of a polypeptide(s) of the present invention is at least 6 (or at least 6.5, or at least 7, or at least 7.5, or at least 8, or at least 8.5, or at least 9). In another embodiment a pH optimum of a polypeptide(s) of the present invention is more than 6 (or more than 6.5, or more than 7, or more than 7.5, or more than 8, or more than 8.5, or more than 9).

In another embodiment a pH optimum of a polypeptide(s) of the present invention is selected in the range from about 6 to about 9, wherein said polypeptide has a significantly higher relative activity at pH 10 ranging from 23-90% compared to a beta-glucanase from *Bacillus subitilis* or *Bacillus amyloliquefaciens*. In another embodiment a pH optimum of a polypeptide(s) of the present invention is selected from the group consisting of: 6, 6.5, 7, 7.5, 8, 8.5, 9, wherein said polypeptide has a significantly higher relative activity at pH 10 ranging from 23-90% compared to a beta-glucanase from *Bacillus subitilis* or *Bacillus amyloliquefaciens*. In another embodiment a pH optimum of a polypeptide(s) of the present invention is at least 6 (or at least 6.5, or at least 7, or at least 7.5, or at least 8, or at least 8.5, or at least 9), wherein said polypeptide has a significantly higher relative activity at pH 10 ranging from 23-90% compared to a beta-glucanase from *Bacillus subitilis* or *Bacillus amyloliquefaciens*. In another embodiment a pH optimum of a polypeptide(s) of the present invention is more than 6 (or more than 6.5, or more than 7, or more than 7.5, or more than 8, or more than 8.5, or more than 9), wherein said polypeptide has a significantly higher relative activity at pH 10 ranging from 23-90% compared to a beta-glucanase from *Bacillus subitilis* or *Bacillus amyloliquefaciens*.

In one aspect, the polypeptides differ by no more than thirty amino acids, e.g., by twenty five amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of sequence selected from the group consisting of: SEQ ID NO: 2, SEQ ID NO: 3, SEQ ID NO: 5, SEQ ID NO: 7, SEQ ID NO: 9. An embodiment is a composition (e.g. a cleaning or detergent composition) comprising said beta-glucanase polypeptide and one or more amylases (and/or one or more proteases).

In an embodiment, the polypeptide has been isolated. A polypeptide of the present invention preferably comprises or consists of the amino acid sequence selected from the group consisting of: SEQ ID NO: 2, SEQ ID NO: 3, SEQ ID NO: 5, SEQ ID NO: 7, SEQ ID NO: 9 or an allelic variant thereof; or is a fragment thereof having beta-glucanase activity. In another aspect, the polypeptide comprises or consists of the mature polypeptide of sequence selected from the group consisting of: SEQ ID NO: 2, SEQ ID NO: 3, SEQ ID NO: 5, SEQ ID NO: 7, SEQ ID NO: 9. An embodiment of the present invention is a composition (e.g. a cleaning or detergent composition) comprising said beta-glucanase polypeptide and one or more amylases (and/or one or more proteases).

In another aspect, the polypeptide comprises or consists of amino acids amino acids 1 to 351 of SEQ ID NO: 2, amino acids 1 to 351 of SEQ ID NO: 3, amino acids 1 to 245 of SEQ ID NO: 5, amino acids 1 to 222 of SEQ ID NO: 7, amino acids 1 to 214 of SEQ ID NO: 9. An embodiment of the present invention is a composition (e.g. a cleaning or detergent composition) comprising said beta-glucanase polypeptide and one or more amylases (and/or one or more proteases).

In another embodiment beta-glucanase of the present invention is not an endo-cellulase having activity on β-1,4 linkages between D-glucose units of cellulose. In another embodiment beta-glucanase of the present invention have licheninase (EC 3.2.1.73) enzymatic activity having activity on β-1,3 β-1,4 glucans. An embodiment of the present invention is a composition (e.g. a cleaning or detergent composition) comprising said beta-glucanase polypeptide and one or more amylases (and/or one or more proteases).

In another embodiment beta-glucanase of the present invention comprises alkaline beta-glucanase activity (e.g. beta-glucanase activity in an aqueous solution at pH 7.5 or above, e.g. beta-glucanase activity at pH selected from the group consisting of 7.5, 8, 9, 10, 11, 12, 13, 13.5, e.g. beta-glucanase activity at pH in the range from about 7.5 to about 13.5, wherein said aqueous solution optionally comprises a bleaching agent, preferably said pH is selected in the range from about 7.5 to about 12.5, further preferably said pH is selected in the range from about 8.5 to about 11.5, most preferably said pH is selected in the range from about 9.5 to about 10.5). An embodiment of the present invention is a composition (e.g. a cleaning or detergent composition) comprising said beta-glucanase polypeptide and one or more amylases (and/or one or more proteases).

In another embodiment a beta-glucanase of the present invention is capable of:

i) having beta-glucanase activity for at least 15 minutes in an aqueous solution with a pH selected in the range from about 7.5 to about 13.5, wherein said aqueous solution optionally comprises a bleaching agent, preferably said pH is selected in the range from about 7.5 to about 12.5, further preferably said pH is selected in the range from about 8.5 to about 11.5, most preferably said pH is selected in the range from about 9.5 to about 10.5; and/or ii) having beta-glucanase activity for at least 15 minutes in an aqueous solution at a temperature selected in the range from about 20° C. to about 75° C., wherein said aqueous solution optionally comprises a bleaching agent.

An embodiment of the present invention is a composition (e.g. a cleaning or detergent composition) comprising said beta-glucanase polypeptide and one or more amylases (and/or one or more proteases).

In another embodiment a beta-glucanase of the present invention is capable of having beta-glucanase activity in an aqueous solution at a temperature selected in the range from about 20° C. to about 75° C., wherein said aqueous solution optionally comprises a bleaching agent, preferably said temperature is selected in the range from about 40° C. to about 60° C. In another embodiment a beta-glucanase of the present invention is capable of having beta-glucanase activity in an aqueous solution at a temperature selected from the group consisting of: 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 90° C. An embodiment of the present invention is a composition (e.g. a cleaning or detergent composition) comprising said beta-glucanase polypeptide and one or more amylases (and/or one or more proteases).

In another embodiment a beta-glucanase of the present invention is capable of having beta-glucanase activity for at least 15 minutes, preferably at least 30 minutes. In another embodiment a beta-glucanase of the present invention is capable of having beta-glucanase activity for a period of time selected from the group consisting of: at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30 minutes, e.g. in combination with any single or multiple embodiments as disclosed herein. An embodiment of the present invention is a composition (e.g. a cleaning or detergent composition) comprising said beta-glucanase polypeptide and one or more amylases (and/or one or more proteases).

In another embodiment, a cleaning or detergent composition comprising a beta-glucanase polypeptide and one or more amylases, wherein said amylase is an alpha-amylase.

In another embodiment, a cleaning or detergent composition of the invention comprising a beta-glucanase polypeptide and one or more amylases, wherein said alpha-amylase is selected from the group consisting of:

(a) a polypeptide having at least 90% sequence identity to SEQ ID NO: 13 (corresponding to SEQ ID NO: 2 of WO 95/10603);

(b) a polypeptide having at least 90% sequence identity to SEQ ID NO: 13 (corresponding to SEQ ID NO: 2 in WO 95/10603) wherein the polypeptide comprises a substitution in one or more of positions: 15, 23, 105, 106, 124, 128, 133, 154, 156, 178, 179, 181, 188, 190, 197, 201, 202, 207, 208, 209, 211, 243, 264, 304, 305, 391, 408, and/or 444;

(c) a polypeptide having at least 90% sequence identity to SEQ ID NO: 14 (corresponding to SEQ ID NO: 6 in WO 02/010355);

(d) a polypeptide having at least 90% sequence identity to the hybrid polypeptide of SEQ ID NO: 15 (comprising residues 1-33 of SEQ ID NO: 6 of WO 2006/066594 and residues 36-483 of SEQ ID NO: 4 of WO 2006/066594);

(e) a polypeptide having at least 90% sequence identity to the hybrid polypeptide of SEQ ID NO: 15 (comprising residues 1-33 of SEQ ID NO: 6 of WO 2006/066594 and residues 36-483 of SEQ ID NO: 4 of WO 2006/066594), wherein the hybrid polypeptide comprises a substitution, a deletion or an insertion in one of more of positions: 48, 49, 107, 156, 181, 190, 197, 201, 209 and/or 264;

(f) a polypeptide having at least 90% sequence identity to SEQ ID NO: 16 (corresponding to SEQ ID NO: 6 of WO 02/019467);

(g) a polypeptide having at least 90% sequence identity to SEQ ID NO: 16 (corresponding to SEQ ID NO: 6 of WO 02/019467), wherein the polypeptide comprises a substitution, a deletion or an insertion in one of more of positions: 181, 182, 183, 184, 195, 206, 212, 216 and/or 269;

(h) a polypeptide having at least 90% sequence identity to SEQ ID NO: 17, SEQ ID NO: 18 or SEQ ID NO: 19 (corresponding to SEQ ID NO: 1, SEQ ID NO: 2 or SEQ ID NO: 7 of WO 96/023873)

(i) a polypeptide having at least 90% sequence identity to SEQ ID NO: 17, SEQ ID NO: 18 or SEQ ID NO: 19 (corresponding to SEQ ID NO: 1, SEQ ID NO: 2 or SEQ ID NO: 7 of WO 96/023873), wherein the polypeptide comprises a substitution, a deletion or an insertion in one of more of positions: 140, 183, 184 195, 206, 243, 260, 304 and/or 476;

(j) a polypeptide having at least 90% sequence identity to SEQ ID NO: 20 (corresponding to SEQ ID NO: 2 of WO 08/153815);

(k) a polypeptide having at least 90% sequence identity to SEQ ID NO: 21 (corresponding to SEQ ID NO: 10 of WO 01/66712);

(l) a polypeptide having at least 90% sequence identity to SEQ ID NO: 21 (corresponding to SEQ ID NO: 10 of WO 01/66712), wherein the polypeptide comprises a substitution, a deletion or an insertion in one of more of positions: 176, 177, 178, 179, 190, 201, 207, 211 and/or 264;

(m) a polypeptide having at least 90% sequence identity to SEQ ID NO: 22 (corresponding to SEQ ID NO: 2 of WO 09/061380);

(n) a polypeptide having at least 90% sequence identity to SEQ ID NO: 22 (corresponding to SEQ ID NO: 2 of WO 09/061380), wherein the polypeptide comprises a substitution, a deletion or an insertion in one of more of positions: 87, 98, 125, 128, 131, 165, 178, 180, 181, 182, 183, 201, 202, 225, 243, 272, 282, 305, 309, 319, 320, 359, 444 and/or 475;

(o) a polypeptide having at least 90% sequence identity to SEQ ID NO: 21, wherein the polypeptide comprises a substitution, a deletion or an insertion in one of more of positions: 28, 118, 174; 181, 182, 183, 184, 186, 189, 195, 202, 298, 299, 302, 303, 306, 310, 314; 320, 324, 345, 396, 400, 439, 444, 445, 446, 449, 458, 471 and/or 484;

(p) a polypeptide having at least 90% sequence identity to SEQ ID NO: 12;

(q) a polypeptide having at least 90% sequence identity (e.g., at least 95% or 100% sequence identity) to a variant of SEQ ID NO:23 having alterations G182*+D183*;

(r) a polypeptide having at least 90% sequence identity (e.g., at least 95% or 100% sequence identity) to a variant of SEQ ID NO:24 having alterations H183*+G184*+I405L+A421H+A422P+A428T;

(s) a polypeptide having at least 90% sequence identity (e.g., at least 95% or 100% sequence identity) to a variant of SEQ ID NO:24 having alterations M9L+R118K+G149A+G182T+G186A+D183*+G184*+N195F+M202L+T257I+Y295F+N299Y+R320K+M323T+A339S+E345R+R458K;

(t) a polypeptide having at least 90% sequence identity (e.g., at least 95% or 100% sequence identity) to a variant of SEQ ID NO: 24 having alterations R178*+G179*+E187P+I203Y+R458N+T459S+D460T+G476K (u) a polypeptide having at least 90% sequence identity (e.g., at least 95% or 100% sequence identity) to a variant of SEQ ID NO: 27 having alteration M202L;

(v) a polypeptide having at least 90% sequence identity (e.g., at least 95% or 100% sequence identity) to a variant of SEQ ID NO: 28 having alterations R180*+S181*+S243Q+G475K;

(w) a polypeptide having at least 90% sequence identity (e.g., at least 95% or 100% sequence identity) to a variant of SEQ ID NO: 29 having alterations D183*+G184*+W140Y+N195F+I206Y+Y243F+E260G+G304R+G476K;

(x) a polypeptide having at least 90% sequence identity (e.g., at least 95% or 100% sequence identity) to a variant of SEQ ID NO: 30 having alterations H1*+N54S+V56T+K72R+G109A+F113Q+R116Q+W167F+Q172G+A174S+G184T+N195F+V206L+K391A+P473R+G476K;

(y) a polypeptide having at least 90% sequence identity (e.g., at least 95% or 100% sequence identity) to a variant of SEQ ID NO: 31 having alterations M9L+R118K+G149A+G182T+G186A+D183*+G184*+N195F+T246V+T257I+Y295F+N299Y+R320K+M323T+A339S+E345R+R458K.

In another embodiment, a cleaning or detergent composition of the invention comprising a beta-glucanase polypeptide and one or more proteases, wherein said protease is selected from the group consisting of:

a) a polypeptide having protease activity, which has at least 60% sequence identity (e.g., at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity) to SEQ ID NO: 34;

b) a polypeptide having protease activity, which has at least 60% sequence identity (e.g., at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity) to SEQ ID NO: 35;

c) a polypeptide having protease activity, which has at least 60% sequence identity (e.g., at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity) to SEQ ID NO: 36.

In another embodiment, the present invention relates to a polypeptide having beta-glucanase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence selected from the group consisting of: SEQ ID NO: 1, SEQ ID NO: 4, SEQ ID NO: 6, SEQ ID NO: 8, (ii) the cDNA sequence thereof, or (iii) the full-length complement of (i) or (ii) (Sambrook et al., 1989, Molecular Cloning, A Laboratory Manual, 2d edition, Cold Spring Harbor, New York). In an embodiment, the polypeptide has been isolated. An embodiment of the present invention is a composition (e.g. a cleaning or detergent composition) comprising said beta-glucanase polypeptide and one or more amylases (and/or one or more proteases).

The polynucleotide of sequence selected from the group consisting of: SEQ ID NO: 1, SEQ ID NO: 4, SEQ ID NO: 6, SEQ ID NO: 8 or a subsequence thereof, as well as the polypeptide of sequence selected from the group consisting of: SEQ ID NO: 2, SEQ ID NO: 3, SEQ ID NO: 5, SEQ ID NO: 7, SEQ ID NO: 9 or a fragment thereof may be used to design nucleic acid probes to identify and clone DNA encoding polypeptides having beta-glucanase activity from strains of different genera or species according to methods well known in the art. An embodiment of the present invention is a composition (e.g. a cleaning or detergent composition) comprising said beta-glucanase polypeptide and one or more amylases (and/or one or more proteases). In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention. An embodiment of the present invention is a composition (e.g. a cleaning or detergent composition) comprising said beta-glucanase polypeptide and one or more amylases (and/or one or more proteases).

A genomic DNA or cDNA library prepared from such other strains may be screened for DNA that hybridizes with the probes described above and encodes a polypeptide having beta-glucanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with sequence selected from the group consisting of: SEQ ID NO: 1, SEQ ID NO: 4, SEQ ID NO: 6, SEQ ID NO: 8 or a subsequence thereof, the carrier material is used in a Southern blot. An embodiment of the present invention is a composition (e.g. a cleaning or detergent composition) comprising said beta-glucanase polypeptide and one or more amylases (and/or one or more proteases).

For purposes of the present invention, hybridization indicates that the polynucleotide hybridizes to a labeled nucleic acid probe corresponding to (i) sequence selected from the group consisting of: SEQ ID NO: 1, SEQ ID NO: 4, SEQ ID NO: 6, SEQ ID NO: 8; (ii) the mature polypeptide coding sequence selected from the group consisting of: SEQ ID NO: 1, SEQ ID NO: 4, SEQ ID NO: 6, SEQ ID NO: 8; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art. An embodiment of the present invention is a composition (e.g. a cleaning or detergent composition) comprising said beta-glucanase polypeptide and one or more amylases (and/or one or more proteases).

In one aspect, the nucleic acid probe is nucleotides 85 to 1137 or nucleotides 1 to 1137 of SEQ ID NO: 1. In one aspect, the nucleic acid probe is nucleotides 1 to 828 or nucleotides 94 to 828 of SEQ ID NO: 4. In one aspect, the nucleic acid probe is nucleotides 1 to 711 or nucleotides 46 to 711 of SEQ ID NO: 6. In one aspect, the nucleic acid probe is nucleotides 1 to 729 or nucleotides 88 to 729 of SEQ ID NO: 8. An embodiment of the present invention is a composition (e.g. a cleaning or detergent composition) comprising said beta-glucanase polypeptide and one or more amylases (and/or one or more proteases).

In another aspect, the nucleic acid probe is a polynucleotide that encodes the polypeptide of sequence selected from the group consisting of: SEQ ID NO: 2, SEQ ID NO: 3, SEQ ID NO: 5, SEQ ID NO: 7, SEQ ID NO: 9; the mature polypeptide thereof; or a fragment thereof. An embodiment of the present invention is a composition (e.g. a cleaning or detergent composition) comprising said beta-glucanase polypeptide and one or more amylases (and/or one or more proteases).

In another aspect, the nucleic acid probe is a sequence selected from the group consisting of: SEQ ID NO: 1, SEQ ID NO: 4, SEQ ID NO: 6, SEQ ID NO: 8. An embodiment of the present invention is a composition (e.g. a cleaning or detergent composition) comprising said beta-glucanase polypeptide and one or more amylases (and/or one or more proteases).

In another embodiment, the present invention relates to an polypeptide having beta-glucanase activity encoded by a polynucleotide having a sequence identity to the mature polypeptide coding sequence of the sequence selected from the group consisting of: SEQ ID NO: 2, SEQ ID NO: 3, SEQ ID NO: 5, SEQ ID NO: 7, SEQ ID NO: 9 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. An embodiment of the present invention is a composition (e.g. a cleaning or detergent composition) comprising said beta-glucanase polypeptide and one or more amylases (and/or one or more proteases). In a further embodiment, the polypeptide has been isolated.

In another embodiment, the present invention relates to variants of the mature polypeptide of sequence selected from the group consisting of: SEQ ID NO: 2, SEQ ID NO: 3, SEQ ID NO: 5, SEQ ID NO: 7, SEQ ID NO: 9 comprising a substitution, deletion, and/or insertion at one or more (e.g., several) positions. An embodiment of the present invention is a composition (e.g. a cleaning or detergent composition) comprising said beta-glucanase polypeptide and one or more amylases (and/or one or more proteases). In an embodiment, the number of amino acid substitutions, deletions and/or insertions introduced into the mature polypeptide of sequence selected from the group consisting of: SEQ ID NO: 2, SEQ ID NO: 3, SEQ ID NO: 5, SEQ ID NO: 7, SEQ ID NO: 9 is up to 10, e.g., 1, 2, 3, 4, 5, 6, 7, 8, 9, or 10. An embodiment of the present invention is a composition (e.g. a cleaning or detergent composition) comprising said beta-glucanase polypeptide and one or more amylases (and/or one or more proteases). The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain. An embodiment of the present invention is a composition (e.g. a cleaning or detergent composition) comprising said beta-glucanase polypeptide and one or more amylases (and/or one or more proteases).

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, AlaN/Val, Ser/Gly, Tyr/Phe, Ala/Pro, Lys/Arg, Asp/Asn, Leu/Ile, LeuNal, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for beta-glucanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Beta-Glucanase Activity

A polypeptide having beta-glucanase activity of the present invention may be obtained from microorganisms of any genus (e.g. genus *Bacillus*). For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* polypeptide having beta-glucanase activity, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* polypeptide.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, Bacillus sp., Bacillus akibai, Bacillus agaradhaerens, Bacillus mojavensis* or *Bacillus thuringiensis* polypeptide.

In another aspect, the polypeptide is not a fungal polypeptide (e.g. a polypeptide of the present invention excludes fungal polypeptides). An embodiment of the present invention is a composition (e.g. a cleaning or detergent composition) comprising said beta-glucanase polypeptide and one or more amylases (and/or one or more proteases).

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

In preferred embodiments a polypeptide of the present invention is a bacterial polypeptide (preferably isolated from a bacterium/bacteria from genus *Bacillus*). In further preferred embodiments a polypeptide of the present invention belongs to Glycoside Hydrolase Family 16 (GH16) (e.g. has Glycoside hydrolases (EC 3.2.1.-) activity). For example, the polypeptide may be a polypeptide having beta-glucanase activity from within a genus *Bacillus*, e.g. from *Bacillus sp-62449, Bacillus akibai, Bacillus agaradhaerens, Bacillus mojavensis*. An embodiment of the present invention is a composition (e.g. a cleaning or detergent composition) comprising said beta-glucanase polypeptide and one or more amylases (and/or one or more proteases).

Catalytic Domains

In one embodiment, the present invention also relates to catalytic domains having a sequence identity to amino acids 33 to 249 of SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 33 to 249 of SEQ ID NO: 2. The catalytic domain preferably comprises or consists of amino acids 33 to 249 of SEQ ID NO: 2 or an allelic variant thereof; or is a fragment thereof having beta-glucanase activity. An embodiment of the present invention is a composition (e.g. a cleaning or detergent composition) comprising said beta-glucanase polypeptide and one or more amylases (and/or one or more proteases).

In one embodiment, the present invention also relates to catalytic domains having a sequence identity to amino acids 62 to 245 of SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 62 to 245 of SEQ ID NO: 2. The catalytic domain preferably comprises or consists of amino acids 62 to 245 of SEQ ID NO: 2 or an allelic variant thereof; or is a fragment thereof having beta-glucanase activity. An embodiment of the present invention is a composition (e.g. a cleaning or detergent composition) comprising said beta-glucanase polypeptide and one or more amylases (and/or one or more proteases).

In one embodiment, the present invention also relates to catalytic domains having a sequence identity to amino acids 33 to 249 of SEQ ID NO: 3 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 33 to 249 of SEQ ID NO: 3. The catalytic domain preferably comprises or consists of amino acids 33 to 249 of SEQ ID NO: 3 or an allelic variant thereof; or is a fragment thereof having beta-glucanase activity. An embodiment of the present invention is a composition (e.g. a cleaning or detergent composition) comprising said beta-glucanase polypeptide and one or more amylases (and/or one or more proteases).

In one embodiment, the present invention also relates to catalytic domains having a sequence identity to amino acids 62 to 245 of SEQ ID NO: 3 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 62 to 245 of SEQ ID NO: 3. The catalytic domain preferably comprises or consists of amino acids 62 to 245 of SEQ ID NO: 3 or an allelic variant thereof; or is a fragment thereof having beta-glucanase activity. An embodiment of the present invention is a composition (e.g. a cleaning or detergent composition) comprising said beta-glucanase polypeptide and one or more amylases (and/or one or more proteases).

In one embodiment, the present invention also relates to catalytic domains having a sequence identity to amino acids 32 to 254 of SEQ ID NO: 5 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 32 to 254 of SEQ ID NO: 5. The catalytic domain preferably comprises or consists of amino acids 32 to 254 of SEQ ID NO: 5 or an allelic variant thereof; or is a fragment thereof having beta-glucanase activity. An embodiment of the present invention is a composition (e.g. a cleaning or detergent composition) comprising said beta-glucanase polypeptide and one or more amylases (and/or one or more proteases).

In one embodiment, the present invention also relates to catalytic domains having a sequence identity to amino acids 60 to 249 of SEQ ID NO: 5 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 60 to 249 of SEQ ID NO: 5. The catalytic domain preferably comprises or consists of amino acids 60 to 249 of SEQ ID NO: 5 or an allelic variant thereof; or is a fragment thereof having beta-glucanase activity. An embodiment of the present invention is a composition (e.g. a cleaning or detergent composition) comprising said beta-glucanase polypeptide and one or more amylases (and/or one or more proteases).

In one embodiment, the present invention also relates to catalytic domains having a sequence identity to amino acids 20 to 236 of SEQ ID NO: 7 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. An embodiment of the present invention is a composition (e.g. a cleaning or detergent composition) comprising said beta-glucanase polypeptide and one or more amylases (and/or one or more proteases). In one aspect, the catalytic domains comprise amino acid sequences that differ by up to 10 amino acids, e.g., 1, 2, 3, 4, 5, 6, 7, 8, 9, or 10, from amino acids 20 to 236 of SEQ ID NO: 7. The catalytic domain preferably comprises or consists of amino acids 20 to 236 of SEQ ID NO: 7 or an allelic variant thereof- or is a fragment thereof having beta-glucanase activity. An embodiment of the present invention is a composition (e.g. a cleaning or detergent composition) comprising said beta-glucanase polypeptide and one or more amylases (and/or one or more proteases).

In one embodiment, the present invention also relates to catalytic domains having a sequence identity to amino acids 49 to 230 of SEQ ID NO: 7 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. An embodiment of the present invention is a composition (e.g. a cleaning or detergent composition) comprising said beta-glucanase polypeptide and one or more amylases (and/or one or more proteases). In one aspect, the catalytic domains comprise amino acid sequences that differ by up to 10 amino acids, e.g., 1, 2, 3, 4, 5, 6, 7, 8, 9, or 10, from amino acids 49 to 230 of SEQ ID NO: 7. The catalytic domain preferably comprises or consists of amino acids 49 to 230 of SEQ ID NO: 7 or an allelic variant thereof- or is a fragment thereof having beta-glucanase activity. An embodiment of the present invention is a composition (e.g. a cleaning or detergent composition) comprising said beta-glucanase polypeptide and one or more amylases (and/or one or more proteases).

In one embodiment, the present invention also relates to catalytic domains having a sequence identity to amino acids 30 to 243 of SEQ ID NO: 9 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. An embodiment of the present invention is a composition (e.g. a cleaning or detergent composition) comprising said beta-glucanase polypeptide and one or more amylases (and/or one or more proteases). In one aspect, the catalytic domains comprise amino acid sequences that differ by up to 10 amino acids, e.g., 1, 2, 3, 4, 5, 6, 7, 8, 9, or 10, from amino acids 30 to 243 of SEQ ID NO: 9. The catalytic domain preferably comprises or consists of amino acids 30 to 243 of SEQ ID NO: 9 or an allelic variant thereof; or is a fragment thereof having beta-glucanase activity. An embodiment of the present invention is a composition (e.g. a cleaning or detergent composition) comprising said beta-glucanase polypeptide and one or more amylases (and/or one or more proteases).

In one embodiment, the present invention also relates to catalytic domains having a sequence identity to amino acids 55 to 239 of SEQ ID NO: 9 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. An embodiment of the present invention is a composition (e.g. a cleaning or detergent composition) comprising said beta-glucanase polypeptide and one or more amylases (and/or one or more proteases). In one aspect, the catalytic domains comprise amino acid sequences that differ by up to 10 amino acids, e.g., 1, 2, 3, 4, 5, 6, 7, 8, 9, or 10, from amino acids 55 to 239 of SEQ ID NO: 9. The catalytic domain preferably comprises or consists of amino acids 55 to 239 of SEQ ID NO: 9 or an allelic variant thereof; or is a fragment thereof having beta-glucanase activity. An embodiment of the present invention is a composition (e.g.

a cleaning or detergent composition) comprising said beta-glucanase polypeptide and one or more amylases (and/or one or more proteases).

Binding Domains

The GH16 beta-glucanase of the invention may comprise a carbohydrate binding module (or CBM). In one embodiment a CBM is in amino acids 264-377 of SEQ ID NO: 2. An embodiment of the present invention is a composition (e.g. a cleaning or detergent composition) comprising said beta-glucanase polypeptide and one or more amylases (and/or one or more proteases). In another embodiment a CBM is in amino acids 264-377 of SEQ ID NO: 3. An embodiment of the present invention is a composition (e.g. a cleaning or detergent composition) comprising said beta-glucanase polypeptide and one or more amylases (and/or one or more proteases).

In one embodiment, the present invention also relates to carbohydrate binding module having a sequence identity to amino acids 264 to 377 of SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. An embodiment of the present invention is a composition (e.g. a cleaning or detergent composition) comprising said beta-glucanase polypeptide and one or more amylases (and/or one or more proteases). In one aspect, the carbohydrate binding module comprise amino acid sequences that differ by up to 10 amino acids, e.g., 1, 2, 3, 4, 5, 6, 7, 8, 9, or 10, from amino acids 264 to 377 of SEQ ID NO: 2. An embodiment of the present invention is a composition (e.g. a cleaning or detergent composition) comprising said beta-glucanase polypeptide and one or more amylases (and/or one or more proteases).

In one embodiment, the present invention also relates to carbohydrate binding module having a sequence identity to amino acids 264 to 377 of SEQ ID NO: 3 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. An embodiment of the present invention is a composition (e.g. a cleaning or detergent composition) comprising said beta-glucanase polypeptide and one or more amylases (and/or one or more proteases). In one aspect, the carbohydrate binding module comprise amino acid sequences that differ by up to 10 amino acids, e.g., 1, 2, 3, 4, 5, 6, 7, 8, 9, or 10, from amino acids 264 to 377 of SEQ ID NO: 3. An embodiment of the present invention is a composition (e.g. a cleaning or detergent composition) comprising said beta-glucanase polypeptide and one or more amylases (and/or one or more proteases).

The carbohydrate binding module preferably comprises or consists of amino acids 264 to 377 of SEQ ID NO: 2 or an allelic variant thereof- or is a fragment thereof having carbohydrate binding activity. An embodiment of the present invention is a composition (e.g. a cleaning or detergent composition) comprising said beta-glucanase polypeptide and one or more amylases (and/or one or more proteases). The carbohydrate binding module preferably comprises or consists of amino acids 264 to 377 of SEQ ID NO: 3 or an allelic variant thereof; or is a fragment thereof having carbohydrate binding activity. An embodiment of the present invention is a composition (e.g. a cleaning or detergent composition) comprising said beta-glucanase polypeptide and one or more amylases (and/or one or more proteases).

In another embodiment, the present invention also relates to carbohydrate binding module variants of amino acids 264 to 377 of SEQ ID NO: 2 (or SEQ ID NO: 3) comprising a substitution, deletion, and/or insertion at one or more (e.g., several) positions. In one aspect, the number of amino acid substitutions, deletions and/or insertions introduced into the sequence of amino acids 264 to 377 of SEQ ID NO: 2 (or SEQ ID NO: 3) is up to 10, e.g., 1, 2, 3, 4, 5, 6, 8, 9, or 10. An embodiment of the present invention is a composition (e.g. a cleaning or detergent composition) comprising said beta-glucanase polypeptide and one or more amylases (and/or one or more proteases).

A carbohydrate binding module of the present invention may be applied in a fusion protein comprising at least one carbohydrate binding module operably linked to a catalytic domain. The catalytic domain may be from a hydrolase, isomerase, ligase, lyase, oxidoreductase, or transferase, aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase. The polynucleotide encoding the catalytic domain may be obtained from any prokaryotic, eukaryotic, or other source.

Polynucleotides

The present invention also relates to polynucleotides encoding a polypeptide, a catalytic domain, or carbohydrate binding module of the present invention, as described herein. In an embodiment, the polynucleotide encoding the polypeptide, catalytic domain, or carbohydrate binding module of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of sequence selected from the group consisting of: SEQ ID NO: 1, SEQ ID NO: 4, SEQ ID NO: 6, SEQ ID NO: 8 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, Protein Expression and Purification 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* trose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, Bacillus* sp-62449, *Bacillus akibai, Bacillus agaradhaerens, Bacillus mojavensis* and *Bacillus thuringiensis* cells.

The bacterial host cell may also be any *Streptococcus* cell including, but not limited to, *Streptococcus equisimilis,*

*Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysacchadies. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma virde* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention (e.g., in vitro or ex vivo methods of production), comprising (a) cultivating a cell, which in its wild-type form produces the polypeptide, under conditions conducive for production of the polypeptide; and optionally, (b) recovering the polypeptide. In one aspect, the cell is a *Bacillus* cell. In another aspect, the cell is a *Bacillus* sp-62449, or *Bacillus akibai*, or *Bacillus agaradhaerens*, or *Bacillus mojavensis* cell.

The present invention also relates to methods of producing a polypeptide of the present invention (e.g., in vitro or ex vivo methods of production), comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Production in Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The present invention also relates to methods of producing a polypeptide(s) or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations

The present invention also relates to a fermentation broth formulation comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed fermentation broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed fermentation broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed fermentation broth or composition may contain the unfractionated contents of the fermentation materials derived at the end of the fermentation. Typically, the cell-killed fermentation brothor composition contains the spent culture medium and cell debris present after the microbial cells (e.g., filamentous fungal cells) are grown to saturation, incubated under carbon-limiting conditions to allow protein synthesis. In some embodiments, the cell-killed fermentation broth or composition contains the spent cell culture medium, extracellular enzymes, and killed filamentous fungal cells. In some embodiments, the microbial cells present in the cell-killed fermentation broth or composition can be permeabilized and/or lysed using methods known in the art.

A fermentation broth as described herein is typically a liquid, but may contain insoluble components, such as killed cells, cell debris, culture media components, and/or insoluble enzyme(s). In some embodiments, insoluble components may be removed to provide a clarified liquid composition.

The fermentation broth formulations and cell compositions of the present invention may be produced by a method described in WO 90/15861 or WO 2010/096673.

Enzyme Compositions

The present invention also relates to compositions comprising a polypeptide(s) of the present invention. An embodiment is a cleaning or detergent composition comprising a beta-glucanase polypeptide of the invention and one or more amylases (and/or one or more proteases). Preferably, the compositions are enriched in such a polypeptide. The term "enriched" indicates that the beta-glucanase activity of the composition has been increased, e.g., with an enrichment factor of at least 1.1.

The compositions may comprise a polypeptide(s) of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. An embodiment is a cleaning or detergent composition comprising a beta-glucanase polypeptide of the invention and one or more amylases (and/or one or more proteases).

The compositions may be prepared in accordance with methods known in the art and may be in the form of a liquid or a dry composition. The compositions may be stabilized in accordance with methods known in the art. An embodiment is a cleaning or detergent composition comprising a beta-glucanase polypeptide of the invention and one or more amylases (and/or one or more proteases).

Examples are given below of preferred uses of the compositions of the present invention. The dosage of the composition and other conditions under which the composition is used may be determined on the basis of methods known in the art.

Uses

The beta-glucanases of the invention may be used in applications where beta-glucan (e.g. beta-D-glucan, beta-1, 3-1,4 glucan, mix-linkage beta-glucan, barley beta-glucan, oatmeal beta-glucan) needs to be degraded (e.g. under alkaline conditions). An embodiment is a cleaning or detergent composition comprising a beta-glucanase polypeptide of the invention and one or more amylases (and/or one or more proteases). Examples of where beta-glucanases could be used include detergent applications, paper and pulp productions. In one aspect, beta-glucanases of the invention may be used for washing or cleaning a textile and/or a hard surface such as dish wash including Automatic Dish Wash (ADW), Hand Dish Wash (HDW), and/or in a cleaning process such as laundry or hard surface cleaning including dish wash including Automatic Dish Wash (ADW) and industrial cleaning, and/or for laundering and/or hard surface cleaning including dish wash including Automatic Dish Wash (ADW), and/or for at least one of the following: preventing, reducing or removing a biofilm and/or malodor from an item, and/or for anti-redeposition. An embodiment is a cleaning or detergent composition comprising a beta-glucanase polypeptide of the invention and one or more amylases (and/or one or more proteases).

Such beta-glucanases preferably have at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of the sequence selected from the group consisting of: SEQ ID NO: 7, SEQ ID NO: 2, SEQ ID NO: 3, SEQ ID NO: 5, SEQ ID NO: 9. An embodiment of the present invention is a composition (e.g. a cleaning or detergent composition) comprising said beta-glucanase polypeptide and one or more amylases (and/or one or more proteases).

Biofilm can develop on textile when microorganisms are present on an item and stick together on the item. Some microorganisms tend to adhere to the surface of items such as textiles. Some microorganisms adhere to such surfaces and form a biofilm on the surface. The biofilm may be sticky and the adhered microorganisms and/or the biofilm may be difficult to remove. Furthermore, the biofilm adhere soil due to the sticky nature of the biofilm. The commercial laundry detergent compositions available on the marked do not remove such adhered microorganisms or biofilm.

The present invention concerns the use of a polypeptide(s) having beta-glucanase activity for preventing, reducing or removing a biofilm from an item, wherein the polypeptide is obtained from a bacterial source and wherein the item is a textile. An embodiment is a cleaning or detergent composition comprising a beta-glucanase polypeptide of the invention and one or more amylases (and/or one or more proteases). In one embodiment of the invention the polypeptide having beta-glucanase activity is used for preventing, reducing or removing the stickiness of an item. An embodiment is a cleaning or detergent composition comprising a beta-glucanase polypeptide of the invention and one or more amylases (and/or one or more proteases).

Compositions

The present invention also relates to compositions comprising a beta-glucanase of the invention (e.g., a polypeptide(s) of the present invention). The present invention also relates to compositions comprising a beta-glucanase of the invention (e.g., a polypeptide(s) of the present invention) and one or more additional enzymes. The present invention also relates to compositions comprising a beta-glucanase of the invention (e.g., a polypeptide(s) of the present invention) and one or more amylases (and/or one or more proteases), preferably said one or more amylases is one or more alpha-amylases. An embodiment is a cleaning or detergent composition comprising a beta-glucanase polypeptide of the invention and one or more amylases (and/or one or more proteases).

In one embodiment, the present invention relates to compositions in particular to cleaning compositions and/or detergent compositions comprising a beta-glucanase of the invention and a suitable surfactant. An embodiment is a cleaning or detergent composition comprising a beta-glucanase polypeptide of the invention and one or more amylases (and/or one or more proteases).

The present invention also relates to compositions comprising an isolated polypeptide having beta-glucanase activity selected from the group consisting of: a) a polypeptide having at least 75% sequence identity, at least 80% sequence identity, at least 81% sequence identity, at least 82% sequence identity, at least 83% sequence identity, at least 84% sequence identity, at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity or even 100% sequence identity to the mature polypeptide of the sequence selected from the group consisting of: SEQ ID NO: 2, SEQ ID NO: 3, SEQ ID NO: 5, SEQ ID NO: 7, SEQ ID NO: 9; b) a polypeptide encoded by a polynucleotide that hybridizes under medium stringency conditions with (i) the mature polypeptide coding sequence of the sequence selected from the group consisting of: SEQ ID NO: 1, SEQ ID NO: 4, SEQ ID NO: 6, SEQ ID NO: 8 or (ii) the full-length complementary strand of (i); c) a polypeptide encoded by a polynucleotide having at least 75% sequence identity, at least 80% sequence identity, at least 81% sequence identity, at least 82% sequence identity, at least 83% sequence identity, at least 84% sequence identity, at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity or even 100% sequence identity to the mature polypeptide coding sequence of the sequence selected from the group consisting of: SEQ ID NO: 1, SEQ ID NO: 4, SEQ ID NO: 6, SEQ ID NO: 8; e) a variant comprising a substitution, deletion, and/or insertion of one or more (e.g. several) amino acids of the mature polypeptide of the sequence selected from the group consisting of: SEQ ID NO: 2, SEQ ID NO: 3, SEQ ID NO: 5, SEQ ID NO: 7, SEQ ID NO: 9; and f) a fragment of a polypeptide of (a), (b), (c), or (d) that has beta-glucanase activity. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 60% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 75% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 81% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 82% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 83% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 84% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 85% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 86% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 87% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 88% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 89% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 90% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 91% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 92% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 93% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 94% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 95% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 96% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 97% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 98% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 99% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment the compositions of the invention comprise an isolated polypeptide having beta-glucanase activity and having at least 100% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

In one embodiment, the detergent composition may be adapted for specific uses such as laundry, in particular household laundry, dish washing or hard surface cleaning.

In another embodiment a composition of the present invention is a cleaning or a detergent composition. An embodiment is a cleaning or detergent composition comprising a beta-glucanase polypeptide of the invention and one or more amylases (and/or one or more proteases).

Alkaline Liquid detergents having high pH are widely used in cleaning, such as laundry and dish wash cleaning. Liquid detergents with elevated pH are especially commonly used by consumers in North America. The high pH cleaning compositions are also used in industrial cleaning processes. Alkaline detergents include liquids having detergent properties. The pH of such detergents usually ranges in pH from 9 to 12.5. The high pH detergents typically comprise components such as surfactants, builders and bleach components and additionally they may also contain a significant amount of water and alkalis such as NaOH, TSP (Trisodium phosphate), ammonia, Sodium carbonate, Potassium hydroxide (KOH) these alkalis are usually added in amount corresponding to 0.1 to 30 percent weight (wt). Adding enzymes to detergents is highly advantageous as the specific activities of these enzymes effectively removes specific stains from surfaces such as textile and cutlery. However, the difficulty of maintaining acceptable enzyme stability in the high pH liquid detergents has for many years prohibited inclusion of enzymes into these detergents. In another embodiment the present invention relates high pH liquid cleaning compositions comprising an alkaline stable beta-glucanase of the present invention suitable for use in such compositions.

In another embodiment a composition of the present invention preferably contains alkaline buffer system to provide a pH of at least about 7.5, at least about 8, at least about 9, preferably pH 10 or above. Preferably the pH is from about 9 to about 13. In order to achieve the high pH it is necessary to have present an alkali metal hydroxide especially sodium or potassium hydroxide, normally in an amount of 0.1 to about 30% by weight (percentage by weight, abbreviated wt %) of the composition, and preferably 1.0 to 2.5%, or higher amounts of a suitable alkali metal silicate such as metal silicate, according to the desired pH for the product.

In another embodiment a composition of the present invention has pH 6.5 or above, preferably pH of 7.0 or above, more preferably pH of 7.5 or above and optionally comprises a bleaching agent; preferably said pH is selected in the range from about 7.5 to about 13.5, further preferably said pH is selected in the range from about 7.5 to about 12.5, most preferably said pH is selected in the range from about 8.5 to about 11.5, further most preferably said pH is selected in the range from about 9.5 to about 10.5. In a preferred embodiment, detergent compositions with such preferred pH-ranges are solid.

In another embodiment the present invention relates to a liquid cleaning composition having pH 6.5 or above, preferably pH 7.5 or above, comprising at least 0.001 (e.g., at least 0.01) wt % beta-glucanase, wherein said beta-glucanase has an amino acid sequence which has at least 81% sequence identity to the mature polypeptide of the sequence selected from the group consisting of: SEQ ID NO: 2, SEQ ID NO: 3, SEQ ID NO: 5, SEQ ID NO: 7, SEQ ID NO: 9. In further related embodiments beta-glucanase has an amino acid sequence which has at least 82% (or at least 83%, or 84%, or 85%, or 86%, or 87%, or 88%, or 89%, or 90%, or 91%, or 92%, or 93%, or 94%, or 95%, or 96%, or 97%, or 98% or 99% or 100%) sequence identity to the mature polypeptide of the sequence selected from the group consisting of: SEQ ID NO: 2, SEQ ID NO: 3, SEQ ID NO: 5, SEQ ID NO: 7, SEQ ID NO: 9. An embodiment is a cleaning or detergent composition comprising a beta-glucanase polypeptide of the invention and one or more amylases (and/or one or more proteases).

The detergent compositions of the invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. The detergent compositions of the invention may find use in hard surface cleaning, automatic dishwashing applications, as well as cosmetic applications such as dentures, teeth, hair and skin. An embodiment is a cleaning or detergent composition comprising a beta-glucanase polypeptide of the invention and one or more amylases (and/or one or more proteases). It can also be used to clean the parts of the dishwasher or washing machine interior during cleaning process, especially the hidden parts, like the water pipelines inside the machine, especially these in the rotatable arms, and the sieve/filter.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous. An embodiment is a cleaning or detergent composition comprising a beta-glucanase polypeptide of the invention and one or more amylases (and/or one or more proteases).

Unless otherwise noted, all component or composition levels provided herein are made in reference to the active level of that component or composition, and are exclusive of impurities, for example, residual solvents or by-products, which may be present in commercially available sources. An embodiment is a cleaning or detergent composition comprising a beta-glucanase polypeptide of the invention and one or more amylases (and/or one or more proteases).

The beta-glucanase of the invention is normally incorporated in the detergent composition at a level of from 0.000001% to 2% of enzyme protein by weight of the composition, preferably at a level of from 0.00001% to 1% of enzyme protein by weight of the composition, more preferably at a level of from 0.0001% to 0.75% of enzyme protein by weight of the composition, even more preferably at a level of from 0.001% to 0.5% of enzyme protein by weight of the composition. An embodiment is a cleaning or detergent composition comprising a beta-glucanase polypeptide of the invention and one or more amylases (and/or one or more proteases).

Furthermore, the beta-glucanase of the invention is normally incorporated in the detergent composition in such amounts that their concentration in the wash water is at a level of from 0.0000001% to 1% enzyme protein, preferably at a level of from 0.000005% to 0.01% of enzyme protein, more preferably at a level of from 0.000001% to 0.005% of enzyme protein, even more preferably at a level of from 0.00001% to 0.001% of enzyme protein in wash water. An embodiment is a cleaning or detergent composition comprising a beta-glucanase polypeptide of the invention and one or more amylases (and/or one or more proteases).

As is well known, the amount of enzyme will also vary according to the particular application and/or as a result of the other components included in the compositions.

A composition for use in automatic dishwash (ADW), for example, may include 0.0001%-50%, such as 0.001%-25%, such as 0.002%-20%, such as 0.01-15% of enzyme protein by weight of the composition. An embodiment is a cleaning or detergent composition comprising a beta-glucanase polypeptide of the invention and one or more amylases (and/or one or more proteases).

A composition for use in automatic dishwash (ADW), for example, may include 0.001%-50%, such as 0.01%-25%, such as 0.02%-20%, such as 0.1-15% of enzyme protein by weight of the composition. An embodiment is a cleaning or detergent composition comprising a beta-glucanase polypeptide of the invention and one or more amylases (and/or one or more proteases).

A composition for use in laundry granulation, for example, may include 0.0001%-50%, such as 0.001%-20%, such as 0.01%-15%, such as 0.05%-10% of enzyme protein by weight of the composition. An embodiment is a cleaning or detergent composition comprising a beta-glucanase polypeptide of the invention and one or more amylases (and/or one or more proteases).

A composition for use in laundry liquid, for example, may include 0.0001%-10%, such as 0.001-7%, such as 0.1%-5% of enzyme protein by weight of the composition. An embodiment is a cleaning or detergent composition comprising a beta-glucanase polypeptide of the invention and one or more amylases (and/or one or more proteases).

A preferred detergent composition, comprises the polypeptide of the invention in concentrations of 0.00001 mg enzyme protein/g composition to 100 mg enzyme protein/g composition, preferred 0.0001 mg enzyme protein/g composition to 50 mg enzyme protein/g composition, more preferred 0.001 mg enzyme protein/g composition to 20 mg enzyme protein/g composition, especially preferred 0.01 mg enzyme protein/g composition to 10 mg enzyme protein/g composition.

A preferred detergent composition, especially a composition formulated as unit dose product, comprises the polypeptide of the invention in amounts from 0.01 mg/job to 100 mg enzyme protein/job, preferred 0.1 mg enzyme protein/job to 20 mg/job, more preferred 0.2 to 10 mg enzyme protein/job, especially preferred 0.3 to 5 mg enzyme protein/job. For example, amounts of 0.5 mg 1 mg, 1.5 mg, 2 mg or 2.5 mg enzyme protein/job can be used. The expression mg per job (mg/job) or mg/application refers to the amount of active substance used in relation to the total weight of the composition used for a complete cleaning cycle (which is to say in the case of detergent agents, the total amount of the cleaning agent used in a complete cleaning cycle of washing). In the case of preportioned cleaning agents, this information is the amount of the active substance in mg based on the total weight of the preportioned cleaning composition.

Said amounts are also applicable for each of the other individual enzyme proteins (e.g. amylase or protease) used in the dishwashing composition of the invention.

In some preferred embodiments, the detergent compositions provided herein are typically formulated such that, during use in aqueous cleaning operations, the wash water has a pH of from about 5.0 to about 13.5, or in alternative embodiments, even from about 6.0 to about 10.5, such as from about 5 to about 11, from about 5 to about 10, from about 5 to about 9, from about 5 to about 8, from about 5 to about 7, from about 6 to about 11, from about 6 to about 10, from about 6 to about 9, from about 6 to about 8, from about 6 to about 7, from about 7 to about 11, from about 7 to about 10, from about 7 to about 9, or from about 7 to about 8. Preferably, the detergent compositions provided herein are typically formulated such that, during use in aqueous cleaning operations, the wash water has a pH selected in the range from about 7.5 to about 13.5, further preferably said pH is selected in the range from about 8.5 to about 11.5, most preferably said pH is selected in the range from about 9.5 to about 10.5; further most preferably pH 7.5 or above. An embodiment is a cleaning or detergent composition comprising a beta-glucanase polypeptide of the invention and one or more amylases (and/or one or more proteases).

In one embodiment, the beta-glucanase of the invention has improved stability, in particular improved storage stability in a high pH liquid cleaning composition, compared to known beta-glucanases. In a preferred embodiment, the beta-glucanase of the invention has improved stability, in particular improved storage stability, and on par or improved wash performance compared to the known beta-glucanases. An embodiment is a cleaning or detergent composition comprising a beta-glucanase polypeptide of the invention and one or more amylases (and/or one or more proteases).

In some preferred embodiments, granular or liquid laundry products are formulated such that the wash water has a pH from about 5.5 to about 8. In other preferred embodiments, granular or liquid laundry products are formulated such that the wash water has a pH selected in the range from about 7.5 to about 13.5, further preferably said pH is selected in the range from about 8.5 to about 11.5, most preferably said pH is selected in the range from about 9.5 to about 10.5; further most preferably pH 7.5 or above. Techniques for controlling pH at recommended usage levels include the use of buffers, alkalis, acids, etc., and are well known to those skilled in the art. An embodiment is a cleaning or detergent composition comprising a beta-glucanase polypeptide of the invention and one or more amylases (and/or one or more proteases).

Enzyme components weights are based on total protein. All percentages and ratios are calculated by weight unless otherwise indicated. All percentages and ratios are calculated based on the total composition unless otherwise indicated. In the exemplified detergent composition, the enzymes levels are expressed by pure enzyme by weight of the total composition and unless otherwise specified, the detergent ingredients are expressed by weight of the total composition.

The enzymes of the present invention also find use in detergent additive products. A detergent additive product comprising a beta-glucanase of the invention is suited for inclusion in a wash process when, e.g., temperature is low, such as at temperatures about 40° C. or below, the pH is between 6 and 8 and the washing time short, e.g., below 30 min. A detergent additive product comprising a beta-glucanase of the invention is further ideally suited for inclusion in an alkaline wash process when, e.g., a pH selected in the range from about 7.5 to about 13.5, a temperature selected in the range from about 20° C. to about 75° C., and the washing time short, e.g., below 30 min, e.g. at least 15 minutes. An embodiment is a cleaning or detergent composition comprising a beta-glucanase polypeptide of the invention and one or more amylases (and/or one or more proteases). Alternatively, a detergent additive product comprising a beta-glucanase of the invention is suited for cleaning of a household dishwasher, e.g. from built-up residues on the filter and in the sump of the machines, preferably from residues containing beta-glucan-containing fibres. Such a machine-cleaning additive product may be suitable to clean at the same time from other residues like fat or limescale.

The detergent additive product may be a beta-glucanase of the invention and preferably an additional enzyme. In one embodiment, the additive is packaged in dosage form for addition to a cleaning process. The single dosage may comprise a pill, tablet, gelcap or other single dosage unit including powders and/or liquids. In some embodiments, filler and/or carrier material(s) are included, suitable filler or carrier materials include, but are not limited to, various salts of sulfate, carbonate and silicate as well as talc, clay and the like. In some embodiments filler and/or carrier materials for liquid compositions include water and/or low molecular weight primary and secondary alcohols including polyols and diols. Examples of such alcohols include, but are not limited to, methanol, ethanol, propanol and isopropanol.

In one particularly preferred embodiment the beta-glucanase according to the invention is employed in a granular composition or liquid, the beta-glucanase may be in form of an encapsulated particle. In one embodiment, the encapsulating material is selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof.

The compositions according to the invention typically comprise one or more detergent ingredients. The term detergent compositions include articles and cleaning and treatment compositions. The term cleaning composition includes, unless otherwise indicated, tablet, granular or powder—form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, gel-form, liquid and rinse-aid types for household and institutional use. The composition can also be in unit dose packages, including those known in the art and those that are water soluble, water insoluble and/or water permeable. These may encompass singlechamber and multichamber pouches.

In embodiments in which cleaning and/or detergent components may not be compatible with the beta-glucanase of the present invention, suitable methods may be used for keeping the cleaning and/or detergent components and the beta-glucanase separated (i.e., not in contact with each other) until combination of the two components is appropriate. Such separation methods include any suitable method known in the art (e.g., gelcaps, encapsulation, tablets, and physical separation e.g., by use of a water dissolvable pouch having one or more compartments).

As mentioned when the beta-glucanase of the invention is employed as a component of a detergent composition (e.g., a laundry washing detergent composition, or a dishwashing detergent composition), it may, for example, be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are polyethyleneglycol (PEG) products with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV)). The enzymes of the detergent compositions of the invention may also be stabilized using conventional stabilizing agents such as polyol, e.g., propylene glycol or glycerol, a sugar or sugar alcohol, lactic acid, and the composition may be formulated as described in, e.g., WO 92/19709 and WO 92/19708. The enzymes of the invention may also be stabilized by adding reversible enzyme inhibitors, e.g., of the protein type (as described in EP 544 777) or the boronic acid type. In a preferred embodiment the enzyme stabilizers are of the boronic acid type, more preferably 4-formyl phenyl boronic acid. The dishwashing composition of the invention is preferably free of boric acid and/or borate, which is to say in particular comprises boric acid and borate in amounts of less than 0.1 wt. %, preferably less than 0.01 wt. %, based on the total composition.

Other enzyme stabilizers are well known in the art, such as peptide aldehydes and protein hydrolysate, e.g. the beta-glucanase according to the invention may be stabilized using peptide aldehydes or ketones such as described in WO2005/105826 and WO2009/118375.

Protected enzymes for inclusion in a detergent composition of the invention may be prepared, as mentioned above, according to the method disclosed in EP 238 216.

The composition may be augmented with one or more agents for preventing or removing the formation of the biofilm. These agents may include, but are not limited to, dispersants, surfactants, detergents, other enzymes, antimicrobials, and biocides.

The compositions of the invention may be applied in dosing elements to be used in an auto-dosing device. The dosing elements comprising the composition of the present invention can be placed into a delivery cartridge as that described in WO 2007/052004 and WO 2007/0833141 or WO 2011/051420, WO 2011/051415, WO 2011/051416, WO 2011/051417, WO 2011/051418, WO 2011/120546 and WO 2011/131260. The dosing elements can have an elongated shape and set into an array forming a delivery cartridge which is the refill for an auto-dosing dispensing device as described in case WO 2007/051989. The delivery cartridge is to be placed in an auto-dosing delivery device, such as that described in WO 2008/053191.

Suitable disclosure of auto-dosing devices can be found in WO 2007/083139, WO 2007/051989, WO 2007/083141, WO 2007/083142 and EP2361964.

Other Enzymes

In one embodiment, a beta-glucanase of the invention is combined with one or more enzymes, such as at least two enzymes, more preferred at least three, four or five enzymes. Preferably, the enzymes have different substrate specificity, e.g., proteolytic activity, amylolytic activity, lipolytic activity, hemicellulytic activity or pectolytic activity. An embodiment is a cleaning or detergent composition comprising a beta-glucanase polypeptide of the invention and one or more amylases (and/or one or more proteases).

The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of animal, vegetable or microbial origin. Particularly suitable cellulases include those of bacterial or fungal origin. Chemically modified or protein engineered variants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 1999/001544.

Commercially available cellulases include Celluzyme®, and Carezyme® (Novozymes A/S), Clazinase®, and Puradax HA® (Genencor International Inc.), and KAC-500 (B)® (Kao Corporation).

Proteases:

Suitable proteases include those of bacterial, fungal, plant, viral or animal origin e.g. microbial or vegetable origin. Microbial origin is preferred. Chemically modified or protein engineered variants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO093/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from Cellulomonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the protease variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase@Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases:

Suitable lipases include those of animal, vegetable or microbial origin. Particularly suitable lipases include those of bacterial or fungal origin. Chemically modified or protein engineered variants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, Biochemica et Biophysica Acta, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™, and Lipex™ (Novozymes A/S).

Amylases:

Suitable amylases which can be used together with beta-glucanase of the invention may be an alpha-amylase or a glucoamylase and may be of bacterial or fungal origin. Chemically modified or protein engineered variants are included. Amylases include, for example, alpha-amylases obtained from Bacillus, e.g., a special strain of Bacillus licheniformis, described in more detail in GB 1,296,839. Suitable amylases include amylases having SEQ ID NO: 3 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from B. amyloliquefaciens shown in SEQ ID NO: 6 of WO 2006/066594 and residues 36-483 of the B. licheniformis alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from B. amyloliquefaciens shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T491+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184. Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476. Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T1311, T1651, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131 I+T1651+K178L+T182G+Y305R+G475K wherein the variants are C-terminally truncated and optionally further comprises a substitution at position 243 and/or a deletion at position 180 and/or position 181. Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions. Other examples are amylase variants such as those described in WO2011/098531, WO2013/001078 and WO2013/001087. Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases:

Suitable peroxidases/oxidases include those of plant, bacterial or fungal origin. Chemically modified or protein engineered variants are included. Examples of useful peroxidases include peroxidases from Coprinus, e.g., from C. cinereus, and variants thereof as those described in WO 93/24618, WO 95/10602, and WO 98/15257.

Commercially available peroxidases include Guardzyme® (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in

Surfactants

Typically, the detergent composition comprises (by weight of the composition, e.g., total amount of surfactant by weight of the composition) one or more surfactants in the range of 0% to 50%, preferably from 2% to 40%, more preferably from 5% to 35%, more preferably from 7% to 30%, most preferably from 10% to 25%, even most preferably from 15% to 20%. In a preferred embodiment the detergent is a liquid or powder detergent comprising less than 40%, preferably less than 30%, more preferably less than 25%, even more preferably less than 20% by weight of surfactant. The composition may comprise from 1% to 15%, preferably from 2% to 12%, 3% to 10%, most preferably from 4% to 8%, even most preferably from 4% to 6% of one or more surfactants. The composition may comprise from 0.1% to 15%, preferably from 0.2% to 12%, 30.5% to 10%, most preferably from 41.0% to 8.0%, even most preferably from 4% to 6% of one or more surfactants (total amount of surfactant by weight of the composition). Preferred surfactants are anionic surfactants, non-ionic surfactants, cationic surfactants, zwitterionic surfactants, amphoteric surfactants, and mixtures thereof. Preferably, the major part of the surfactant is anionic. Suitable anionic surfactants are well known in the art and may comprise fatty acid carboxylates (soap), branched-chain, linear-chain and random chain alkyl sulfates or fatty alcohol sulfates or primary alcohol sulfates or alkyl benzenesulfonates such as LAS and LAB or phenylalknesulfonates or alkenyl sulfonates or alkenyl benzenesulfonates or alkyl ethoxysulfates or fatty alcohol ether sulfates or alpha-olefin sulfonate or dodecenyl/tetradecnylsuccinic acid. The anionic surfactants may be alkoxylated. The detergent composition may also comprise from 1 wt % to 10 wt % of non-ionic surfactant, preferably from 2 wt % to 8 wt %, more preferably from 3 wt % to 7 wt %, even more preferably less than 5 wt % of non-ionic surfactant. Suitable non-ionic surfactants are well known in the art and may comprise alcohol ethoxylates, and/or alkyl ethoxylates, and/or alkylphenol ethoxylates, and/or glucamides such as fatty acid N-glucosyl N-methyl amides, and/or alkyl polyglucosides and/or mono- or diethanolamides or fatty acid amides. The detergent composition may also comprise from 0 wt % to 10 wt % of cationic surfactant, preferably from 0.1 wt % to 8 wt %, more preferably from 0.5 wt % to 7 wt %, even more preferably less than 5 wt % of cationic surfactant. Suitable cationic surfactants are well known in the art and may comprise alkyl quaternary ammonium compounds, and/or alkyl pyridinium compounds and/or alkyl quaternary phosphonium compounds and/or alkyl ternary sulphonium compounds. The composition preferably comprises surfactant in an amount to provide from 100 ppm to 5,000 ppm surfactant in the wash liquor during the laundering process. The composition upon contact with water typically forms a wash liquor comprising from 0.5 g/l to 10 g/l detergent composition. Many suitable surface active compounds are available and fully described in the literature, for example, in "Surface-Active Agents and Detergents", Volumes I and 11, by Schwartz, Perry and Berch.

All nonionic surfactants known to a person skilled in the art may be used as nonionic surfactants. Suitable nonionic surfactants are, for example, alkyl glycosides of the general formula RO(G)x, where R corresponds to a primary straight-chain or methyl-branched, in particular methyl-branched at the 2-position, aliphatic group having 8 to 22, preferably 12 to 18 carbon atoms, and G is the symbol that denotes a glycose unit having 5 or 6 carbon atoms, preferably glucose. The degree of oligomerization x, which indicates the distribution of monoglycosides and oligoglycosides, is any number between 1 and 10; x is preferably 1.2 to 1.4.

Another class of nonionic surfactants that can preferably be used, which can be used either as the sole nonionic surfactant or in combination with other nonionic surfactants, is alkoxylated, preferably ethoxylated or ethoxylated and propoxylated fatty acid alkyl esters, preferably having 1 to 4 carbon atoms in the alkyl chain.

Nonionic surfactants of the amine oxide type, for example N-cocoalkyl-N,N-dimethylamine oxide and N-tallowalkyl-N,N-dihydroxyethylamine oxide, and of the fatty acid alkanolamide type may also be suitable. The quantity of these nonionic surfactants is preferably no more than that of the ethoxylated fatty alcohols, in particular no more than half thereof. Further suitable surfactants are polyhydroxyfatty acid amides, also known as PHFA.

Low-foaming nonionic surfactants can be used as preferred surfactants. With particular preference, the cleaning agents, preferably dishwashing agents, in particular machine dishwashing agents contain nonionic surfactants from the group of alkoxylated alcohols. Alkoxylated, advantageously ethoxylated, in particular primary alcohols having preferably 8 to 18 carbon atoms and on average 1 to 12 mol ethylene oxide (EO) per mol of alcohol, in which the alcohol residue can be linear or preferably methyl-branched at the 2-position, or can contain linear and methyl-branched residues in the mixture, such as those usually present in oxo alcohol groups, are preferably used as nonionic surfactants. However, alcohol ethoxylates having linear groups of alcohols of native origin having 12 to 18 carbon atoms, for example of coconut, palm, tallow fatty or oleyl alcohol, and an average of 2 to 8 mol EO per mol of alcohol are particularly preferred. The preferred ethoxylated alcohols include, for example, C12-14 alcohols having 3 EO or 4 EO, C9-11 alcohol having 7 EO, C13-15 alcohols having 3 EO, 5 EO, 7 EO, or 8 EO, C12-18 alcohols having 3 EO, 5 EO, or 7 EO, and mixtures thereof, such as mixtures of C12-14 alcohol having 3 EO and C12-18 alcohol having 5 EO. The degrees of ethoxylation indicated represent statistical averages that can correspond to an integer or a fractional number for a specific product. Preferred alcohol ethoxylates exhibit a restricted distribution of homologs (narrow range ethoxylates, NRE). In addition to these nonionic surfactants, fatty alcohols having more than 12 EO can also be used. Examples of these are tallow fatty alcohol having 14 EO, 25 EO, 30 EO, or 40 EO.

Nonionic surfactants that have a melting point above room temperature are particularly preferred. Nonionic surfactant(s) having a melting point above 20° C., preferably above 25° C., particularly preferably between 25 and 60° C., and in particular between 26.6 and 43.3° C., is/are particularly preferred.

Surfactants that are preferably to be used come from the groups of alkoxylated nonionic surfactants, in particular ethoxylated primary alcohols. It has been found that dishwashing compositions comprising a polypeptide according to the invention in combination with nonionic surfactants are surprisingly capable of reducing the built up of soils in the interior of the dish washing machine, especially on the sieve.

Builders

The main role of builder is to sequester divalent metal ions (such as calcium and magnesium ions) from the wash solution that would otherwise interact negatively with the surfactant system. Builders are also effective at removing metal ions and inorganic soils from the fabric surface, leading to improved removal of particulate and beverage stains. Builders are also a source of alkalinity and can buffer the pH of the wash water to a level above 7.5, e.g. 9.5 to 11. The buffering capacity is also termed reserve alkalinity, and should preferably be greater than 4, e.g., for solid detergent compositions.

The detergent compositions of the present invention may comprise one or more detergent builders or builder systems. Many suitable builder systems are described in the literature, for example in Powdered Detergents, Surfactant science series volume 71, Marcel Dekker, Inc. Builder may comprise from 0% to 60%, preferably from 5% to 45%, more preferably from 10% to 40%, most preferably from 15% to 35%, even more preferably from 20% to 30% builder by weight of the subject composition. The composition may comprise from 0% to 15%, preferably from 1% to 12%, 2% to 10%, most preferably from 3% to 8%, even most preferably from 4% to 6% of builder by weight of the subject composition.

The builders include in particular silicates, carbonates and organic cobuilders, especially polycarboxylate(s) and/or aminocarboxylate(s).

Crystalline layered silicates may be used in the agents described herein. Such cleaning agents, preferably dishwashing agents, in particular machine dishwashing agents, preferably contain a weight fraction of crystalline layered silicate from 0.1 to 20 wt %, preferably from 0.2 to 15 wt %, and in particular from 0.4 to 10 wt %, in each case based on the total weight of these agents.

Other builders are the alkali carriers. Valid examples of alkali carriers include alkali metal hydroxides, alkali metal carbonates, alkali metal hydrogen carbonates, alkali metal sesquicarbonates, the described alkali silicates, alkali metal silicates and mixtures of the above-mentioned substances, wherein within the meaning of the present invention preferably the alkali carbonates, in particular sodium or potassium carbonate, sodium hydrogen carbonate or sodium sesquicarbonate may be used. However, also the corresponding potassium analogs may be useful in addition to or in complete replacement of the sodium salts. Due to the low chemical compatibility of the optional alkali metal hydroxides with the remaining ingredients of cleaning agents, in particular dishwashing agents, preferably machine dishwashing agents, compared to other builder substances, they are preferably used only in small quantities or not at all.

Builders include, but are not limited to, the alkali metal, ammonium and alkanolammonium salts of polyphosphates (e.g., tripolyphosphate STPP), alkali metal silicates, alkaline earth and alkali metal carbonates, aluminosilicate builders (e.g., zeolite) and polycarboxylate compounds, ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Ethanole amines (MEA, DEA, and TEA) may also contribute to the buffering capacity in liquid detergents.

Preferred dishwash compositions of the invention are "phosphate-free". "Phosphate-free," as used herein, means that the composition in question is essentially free of phosphates, which is to say in particular comprises phosphates in amounts of less than 0.1 wt. %, preferably less than 0.01 wt. %, based on the total composition. The expression "phosphates", as used in this context, does not include the phosphonates described hereafter.

The use of carbonate(s) and/or hydrogen carbonate(s), preferably alkali carbonate(s), particularly preferably sodium carbonate, in quantities from 2 to 50 wt %, preferably from 5 to 40 wt %, and in particular from 7.5 to 30 wt %, in each case based on the weight of the agent, preferably machine dishwashing agent, is particularly preferred. Agents that, based on the weight of the machine dishwashing agent, contain less than 20 wt %, especially less than 17 wt %, preferably less than 13 wt %, and in particular less than 9 wt % carbonate(s) and/or hydrogen carbonate(s), preferably alkali carbonate(s), particularly preferably sodium or potassium carbonate, are particularly preferred.

In particular, polycarboxylates/polycarboxylic acids, polymeric polycarboxylates, aspartic acid, polyacetals, dextrins, further organic cobuilders, and phosphonates should be mentioned as organic cobuilders. These substance classes are described hereafter.

Usable organic builder substances are, for example, the polycarboxylic acids that can be used in the form of the free acid and/or of the sodium salts thereof, wherein polycarboxylic acids shall be understood to mean those carboxylic acids that carry more than one acid function. These include, for example, citric acid, adipic acid, succinic acid, glutaric acid, malic acid, tartaric acid, maleic acid, fumaric acid, saccharic acids, nitrilotriacetic acid (NTA), provided that such use is not objectionable for ecological reasons, and mixtures thereof. In addition to the builder effect, the free acids typically also have the property of being an acidifying component and are thus also used as agents to set a lower and milder pH value. In particular, citric acid, succinic acid, glutaric acid, adipic acid, gluconic acid and arbitrary mixtures of these should be mentioned here.

The use of citric acid and/or citrates in these agents has proven to be particularly advantageous for the cleaning and rinsing power of agents described herein. Preferred are therefore cleaning agents, preferably dishwashing agents, particularly preferably machine dishwashing agents, characterized in that the agent contains citric acid or a salt of citric acid, and the weight fraction of the citric acid or of the salt of citric acid especially is more than 10 wt %, preferably more than 15 wt %, and in particular between 20 and 40 wt %.

Aminocarboxylic acids and/or the salts thereof are another significant class of phosphate-free builders. Particularly preferred representatives of this class are methylglycine diacetic acid (MGDA) or the salts thereof, and glutamine diacetic acid (GLDA) or the salts thereof, or ethylenediamine diacetic acid (EDDS) or the salts thereof. The content of these amino carboxylic acids or of the salts thereof can amount to, for example, between 0.1 and 15 wt %, preferably between 0.5 and 10 wt %, and in particular between 0.5 and 6 wt %. Aminocarboxylic acids and the salts thereof can be used together with the above-mentioned builders, in particular also with the phosphate-free builders.

Suitable builders moreover include polymeric polycarboxylates; for example, these are the alkali metal salts of polyacrylic acid or of polymethacrylic acid, for example those having a relative molar mass from 500 to 70,000 g/mol. Suitable polymers are in particular polyacrylates, which preferably have a molar mass from 2000 to 20,000 g/mol. Due to the superior solubility thereof, short-chain polyacrylates having molar masses from 2000 to 10,000 g/mol, and particularly preferably from 3000 to 5000 g/mol, may in turn be preferred from this group.

In a preferred embodiment the dish washing composition of the invention may comprise, if allowed according to the jurisdiction of the country where the dishwashing composition is used, phosphonates, preferable 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), diethylenetriamine penta(methylenephosphonic acid) (DTPMP), aminotris(methylenephosphonic acid) (ATMP).

In an alternative embodiment the dish washing composition of the invention are phosphate-free as defined above and comprise no ore only small amounts of phosphonates. In a preferred embodiment the dish washing composition contains less than 15 mg/job phosphorus, more preferred less than 10 mg/job phosphorus, most preferred less than 1 mg/job phosphorus.

Bleaches

The detergent compositions of the present invention may comprise one or more bleaching agents. In particular powdered detergents may comprise one or more bleaching agents. Suitable bleaching agents include other photobleaches, pre-formed peracids, sources of hydrogen peroxide, bleach activators, hydrogen peroxide, bleach catalysts and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) other photobleaches for example Vitamin K3;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone, and mixtures thereof. Suitable percarboxylic acids include hydrophobic and hydrophilic peracids having the formula R—(C=O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include inorganic salts such as alkali metal silicate, carbonate or borate salts or mixtures thereof, or organic materials such as water-soluble or dispersible polymers, waxes, oils or fatty soaps. Useful bleaching compositions are described in U.S. Pat. Nos. 5,576,282, and 6,306,812;

(4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof; and (5) bleach catalysts that are capable of accepting an oxygen atom from peroxyacid and transferring the oxygen atom to an oxidizable substrate are described in WO 2008/007319. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof. The bleach catalyst will typically be comprised in the detergent composition at a level of from 0.0005% to 0.2%, from 0.001% to 0.1%, or even from 0.005% to 0.05% by weight.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Adjunct Materials

Dispersants—The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms.

Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—The detergent compositions of the present invention will preferably also contain additional components that may tint articles being cleaned, such as fluorescent whitening agent or optical brighteners. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives.

Preferred fluorescent whitening agents are Tinopal DMS and Tinopal CBS available from Ciba-Geigy AG, Basel, Switzerland. Tinopal DMS is the disodium salt of 4, 4'-bis- (2-morpholino-4 anilino-s-triazin-6-ylamino) stilbene disulphonate. Tinopal CBS is the disodium salt of 2,2'-bis-(phenyl-styryl) disulphonate.

Also preferred are fluorescent whitening agents is the commercially available Parawhite KX, supplied by Paramount Minerals and Chemicals, Mumbai, India.

Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Fabric hueing agents—The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1 876 226. The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch.

Soil release polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series, volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523. Furthermore random graft co-polymers are suitable soil release polymers Suitable graft co-polymers are described in more detail in WO 2007/138054, WO 2006/108856 and WO 2006/113314. Other soil release polymers are substituted polysaccharide structures especially substituted cellulosic structures such as modified cellulose deriviatives such as those described in EP 1 867 808 or WO 2003/040279. Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

In one aspect the detergent is a compact fluid laundry detergent composition comprising: a) at least about 10%, preferably from 20 to 80% by weight of the composition, of surfactant selected from anionic surfactants, non ionic surfactants, soap and mixtures thereof; b) from about 1% to about 30%, preferably from 5 to 30%, by weight of the composition, of water; c) from about 1% to about 15%, preferably from 3 to 10% by weight of the composition, of non-aminofunctional solvent; and d) from about 5% to about 20%, by weight of the composition, of a performance additive selected from chelants, soil release polymers, enzymes and mixtures thereof—wherein the compact fluid laundry detergent composition comprises at least one of:

(i) the surfactant has a weight ratio of the anionic surfactant to the nonionic surfactant from about 1.5:1 to about 5:1, the surfactant comprises from about 15% to about 40%, by weight of the composition, of anionic surfactant and comprises from about 5% to about 40%, by weight of the composition, of the soap; (ii) from about 0.1% to about 10%, by weight of the composition, of a suds boosting agent selected from suds boosting polymers, cationic surfactants, zwitterionic surfactants, amine oxide surfactants, amphoteric surfactants, and mixtures thereof; and (ii) both (i) and (ii). All the ingredients are described in WO 2007/130562. Further polymers useful in detergent formulations are described in WO 2007/149806.

In another aspect the detergent is a compact granular (powdered) detergent comprising a) at least about 10%, preferably from 15 to 60% by weight of the composition, of surfactant selected from anionic surfactants, non-ionic surfactants, soap and mixtures thereof; b) from about 10 to 80% by weight of the composition, of a builder, preferably from 20% to 60% where the builder may be a mixture of builders selected from i) phosphate builder, preferably less than 20%, more preferably less than 10% even more preferably less than 5% of the total builder is a phosphate builder; ii) a zeolite builder, preferably less than 20%, more preferably less than 10% even more preferably less than 5% of the total builder is a zeolite builder; iii) citrate, preferably 0 to 5% of the total builder is a citrate builder; iv) polycarboxylate, preferably 0 to 5% of the total builder is a polycarboxylate builder v) carbonate, preferably 0 to 30% of the total builder is a carbonate builder and vi) sodium silicates, preferably 0 to 20% of the total builder is a sodium silicate builder; c) from about 0% to about 25% by weight of the composition, of fillers such as sulphate salts, preferably from 1% to 15%, more preferably from 2% to 10%, more preferably from 3% to 5% by weight of the composition, of fillers; and d) from about 0.1% to 20% by weight of the composition, of enzymes, preferably from 1% to 15%, more preferably from 2% to 10% by weight of the composition, of enzymes.

The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cutinases, and pectinase.

In a preferred aspect of the present invention the beta-glucanase of the invention may be combined with at least two enzymes. These additional enzymes are described in details in the section "other enzymes", more preferred at least three, four or five enzymes. Preferably, the enzymes have different substrate specificity, e.g., carbolytic activity, proteolytic activity, amylolytic activity, lipolytic activity, hemicellulytic activity or pectolytic activity. The enzyme combination may for example be a beta-glucanase of the invention with another stain removing enzyme, e.g., a beta-glucanase of the invention and a protease, a beta-glucanase of the invention and a serine protease, a beta-glucanase of the invention and an amylase, a beta-glucanase of the invention and a cellulase, beta-glucanase of the invention and a lipase, a beta-glucanase of the invention and a cutinase, a beta-glucanase of the invention and a pectinase or a beta-glucanase of the invention and an anti-redeposition enzyme. More preferably, the beta-glucanase of the invention is combined with at least two other stain removing enzymes, e.g., a beta-glucanase of the invention, a lipase and an amylase; or a beta-glucanase of the invention, a protease and an amylase; or a beta-glucanase of the invention, a protease and a lipase; or a beta-glucanase of the invention, a protease and a pectinase; or a beta-glucanase of the invention, a protease and a cellulase; or a beta-glucanase of the invention, a protease and a hemicellulase; or a beta-glucanase of the invention, a protease and a cutinase; or a beta-glucanase of the invention, an amylase and a pectinase; or a beta-glucanase of the invention, an amylase and a cutinase; or a beta-glucanase of the invention, an amylase and a cellulase; or a beta-glucanase of the invention, an amylase and a hemicellulase; or a beta-glucanase of the invention, a lipase and a pectinase; or a beta-glucanase of the invention, a lipase and a cutinase; or a beta-glucanase of the invention, a lipase and a cellulase; or a beta-glucanase of the invention, a lipase and a hemicellulase. Even more preferably, a beta-glucanase of the invention may be combined with at least three other stain removing enzymes, e.g., a beta-glucanase of the invention, a protease, a lipase and an amylase; or a beta-glucanase of the invention, a protease, an amylase and a pectinase; or a beta-glucanase of the invention, a protease, an amylase and a cutinase; or a beta-glucanase of the invention, a protease, an amylase and a cellulase; or a beta-glucanase of the invention, a protease, an amylase and a hemicellulase; or a beta-glucanase of the invention, an amylase, a lipase and a pectinase; or a beta-glucanase of the invention, an amylase, a lipase and a cutinase; or a beta-glucanase of the invention, an amylase, a lipase and a cellulase; or a beta-glucanase of the invention, an amylase, a lipase and a hemicellulase; or a beta-glucanase of the invention, a protease, a lipase and a pectinase; or a beta-glucanase of the invention, a protease, a lipase and a cutinase; or a beta-glucanase of the invention, a protease, a lipase and a cellulase; or a beta-glucanase of the invention, a protease, a lipase and a hemicellulase. A beta-glucanase according to the present invention may be combined with any of the enzymes selected from the non-exhaustive list comprising: carbohydrases, such as an amylase, a hemicellulase, a pectinase, a cellulase, a xanthanase or a pullulanase, a peptidase, a protease or a lipase.

In a preferred embodiment, a beta-glucanase of the invention is combined with a serine protease, e.g., an S8 family protease such as Savinase®.

In another embodiment of the present invention, a beta-glucanase of the invention may be combined with one or more metalloproteases, such as an M4 metalloprotease, including Neutrase® or Thermolysin. Such combinations may further comprise combinations of the other detergent enzymes as outlined above.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one beta-glucanase of the invention. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alterative and/or improved properties compared to the common used detergent enzymes such as proteases, lipases and amylases is needed to achieve a similar or improved wash performance when compared to the traditional detergent compositions.

Typical detergent compositions includes various components in addition to the enzymes, these components have different effects, some components like the surfactants lower the surface tension in the detergent, which allows the stain being cleaned to be lifted and dispersed and then washed away, other components like bleach systems removes discolor often by oxidation and many bleaches also have strong bactericidal properties, and are used for disinfecting and sterilizing. Yet other components like builder and chelator softens, e.g., the wash water by removing the metal ions from the liquid.

In a particular embodiment, the invention concerns the use of a composition comprising a beta-glucanase of the invention, wherein said enzyme composition further comprises at least one or more of the following a surfactant, a builder, a chelator or chelating agent, bleach system or bleach component in laundry or dish wash.

In a preferred embodiment of the invention the amount of a surfactant, a builder, a chelator or chelating agent, bleach system and/or bleach component are reduced compared to amount of surfactant, builder, chelator or chelating agent, bleach system and/or bleach component used without the added beta-glucanase of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of beta-glucanase of the invention, such as a conventional amount of such component. In one aspect, the beta-glucanase of the invention is used in detergent compositions wherein said composition is free of at least one component which is a surfactant, a builder, a chelator or chelating agent, bleach system or bleach component and/or polymer.

Detergent Compositions

In one embodiment, the invention is directed to detergent compositions comprising an enzyme of the present invention in combination with one or more additional cleaning composition components. The choice of additional components is within the skill of the artisan and includes conventional ingredients, including the exemplary non-limiting components set forth below.

The choice of components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

In one embodiment, the invention is directed to an ADW (Automatic Dish Wash) compositions comprising an enzyme of the present invention in combination with one or more additional ADW composition components. The choice of additional components is within the skill of the artisan and includes conventional ingredients, including the exemplary non-limiting components set forth below.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyttrimethylammonium bromide (CTAB), dimethyldistearylammonium chloride (DSDMAC), and alkylbenzyidimethylammonium, alkyl quatemary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0% to about 40% by weight of a zwitterionic surfactant. Non-limiting examples of zwitterionic surfactants include betaines such as alkyidimethylbetaines, sulfobetaines, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry/ADW/hard surface cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N'-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-30% by weight, such as about 1% to about 20%, of a bleaching system. Any bleaching system known in the art for use in laundry/ADW/hard surface cleaning detergents may be utilized. Suitable bleaching system components include bleaching catalysts, photobleaches, bleach activators, sources of hydrogen peroxide such as sodium percarbonate, sodium perborates and hydrogen peroxide-urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone®, and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767.

It is also possible to use combinations of conventional bleach activators. These bleach activators are preferably used in quantities of up to 10 wt %, in particular 0.1 wt % to 8 wt %, particularly 2 to 8 wt %, and particularly preferably 2 to 6 wt %, based in each case on the total weight of the bleach activator-containing agent.

A particular family of bleach activators of interest was disclosed in EP624154 and particulary preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally, ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

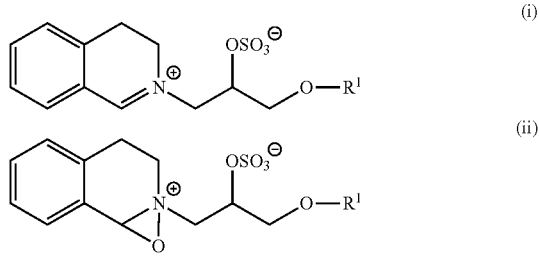

(iii) and mixtures thereof;

wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propyiheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst.

In a preferred embodiment the dishwashing compositions, in particular machine dishwashing compositions, especially solid automatic dishwashing compostions can furthermore contain bleach catalysts. The usable bleach catalysts include, but are not limited to, the group of the bleach-boosting transition metal salts and transition metal complexes, preferably the Mn, Fe, Co, Ru or Mo complexes, particularly preferably from the group of the manganese and/or cobalt salts and/or complexes, in particular the cobalt (ammine) complexes, the cobalt (acetate) complexes, the cobalt (carbonyl) complexes, the chlorides of cobalt or manganese, manganese sulfate and the complexes of manganese with 1,4,7-trimethyl-1,4,7-triazacyclononane (Mn3-TACN) or 1,2,4,7-tetramethyl-1,4,7-triazacyclononane (Mn4-TACN).

Cleaning compositions, preferably dishwashing compositions, in particular machine dishwashing compositions that contain 0.001 to 1 wt %, preferably 0.01 to 0.1 wt % bleach catalyst, preferably an Mn complex, in particular a complex of manganese with 1,4,7-trimethyl-1,4,7-triazacyclononane (Mn3-TACN) or 1,2,4,7-tetramethyl-1,4,7-triazacyclononane (Mn4-TACN) are preferred.

The source of peracid may be selected from (a) preformed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquatemium ethoxy sulfate. Other exemplary polymers are disclosed in, e.g., WO 2006/130575. Salts of the above-mentioned polymers are also contemplated.

In a preferred embodiment the composition of the invention also comprises one or more copolymeric polycarboxylates, in particular those of acrylic acid with methacrylic acid, and of acrylic acid or methacrylic acid with maleic acid.

The (co)polymeric polycarboxylates can be used either as a powder or as an aqueous solution. The content of (co)polymeric polycarboxylates in the cleaning agents, preferably dishwashing agents, in particular machine dishwashing agents, is preferably 0.5 to 20 wt %, and in particular 3 to 10 wt %.

To improve water solubility, the polymers can also contain allyl sulfonic acids, such as allyloxybenzene sulfonic acid and methallyl sulfonic acid, as a monomer. Further preferred copolymers are those that contain acrolein and acrylic acid/acrylic acid salts or acrolein and vinylacetate as monomers.

Moreover, all compounds that are able to form complexes with alkaline earth ions can be used as builders.

In a most preferred embodiment of the invention the dishwash detergent and cleaning composition of the invention additionally comprises a copolymer that contains at least one sulfonic acid containing monomer, a so-called sulfo polymer.

The amount by weight of the sulfo polymer in the total weight of the detergent or cleaning agent produced according to the invention is preferably 0.1 to 20% by weight, in particular 0.5 to 18% by weight, particularly preferably 1.0 to 15% by weight, in particular 4 to 14% by weight, particularly 6 to 12% by weight.

The aqueous solutions of the at least one sulfo polymer typically contain 20 to 70% by weight, in particular 30 to 50% by weight, preferably approx. 35 to 40% by weight sulfo polymer(s).

A polysulfonate copolymer, optionally a hydrophobically modified poly¬sulfonate copolymer, is preferably used as the sulfo polymer. The copolymers may contain two, three, four or more different monomer units.

Preferred polysulfonate copolymers contain at least one monomer from the group of unsaturated carboxylic acids in addition to monomer(s) containing sulfonic acid groups.

Unsaturated carboxylic acids of the formula R1(R2)C=C(R3)COOH, in which R1 to R3 independently of one another stand for —H, —CH3, a linear or branched saturated alkyl radical with 2 to 12 carbon atoms, a linear or branched mono- or polyunsaturated alkenyl radical with 2 to 12 carbon atoms, —NH2, —OH or —COOH-substituted alkyl or alkenyl radicals as defined above, or standing for —COOH or COOR4, where R4 is a saturated or unsaturated linear or branched hydrocarbon radical with 1 to 12 carbon atoms are particularly preferably used as unsaturated carboxylic acid(s).

Particularly preferred unsaturated carboxylic acids include acrylic acid, methacrylic acid, ethacrylic acid, α-chloroacrylic acid, α-cyanoacrylic acid, crotonic acid, α-phenylacrylic acid, maleic acid, maleic anhydride, fumaric acid, itaconic acid, citraconic acid, methylene malonic acid, sorbic acid, cinnamic acid or mixtures thereof. The unsaturated dicarboxylic acids may of course also be used.

Preferred monomers containing sulfonic acid groups are those of the formula

R5(R6)C=C(R7)-X—SO3H, where R5 to R7 independently of one another stand for —H, —CH3, a linear or branched saturated alkyl radical with 2 to 12 carbon atoms, a linear or branched mono- or polyunsaturated alkenyl radical with 2 to 12 carbon atoms, —NH2, —OH or —COOH-substituted alkyl or alkenyl radicals or —COOH or —COOR4, where R4 is a saturated or unsaturated linear or branched hydrocarbon radical with 1 to 12 carbon atoms, and X stands for a spacer group, which is optionally present and is selected from —(CH2)n—where n=0 to 4, —COO—(CH2)k—where k=1 to 6, —C(O)—NH—C(CH3)2-, —C(O)—NH—C(CH3)2-CH2- and —C(O)—NH—CH(CH3)-CH2-. Among these monomers, the preferred ones are those of the formulas

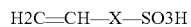

H2C=CH—X—SO3H

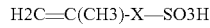

H2C=C(CH3)-X—SO3H

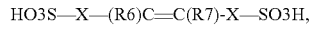

HO3S—X—(R6)C=C(R7)-X—SO3H, where R6 and R7, independently of one another, are selected from H, CH3, CH2CH3, —CH2CH2CH3 and —CH(CH3)2, and X stands for a spacer group, which is optionally present and is selected from —(CH2)n—where n=0 to 4, COO—(CH2)k—where k=1 to 6, —C(O)—NH—C(CH3)2-, —C(O)—NH—C(CH3)2-CH2- and C(O)—NH—CH(CH3)-CH2-.

Particularly preferred monomers that contain sulfonic acid groups include 1-acrylamido-1-propanesulfonic acid, 2-acrylamido-2-propanesulfonic acid, 2-acryl¬amido-2-methyl-1-propanesulfonic acid, 2-methacrylamido-2-methyl-1-propane¬sulfonic acid, 3-methacrylamido-2-hydroxypropanesulfonic acid, allylsulfonic acid, methallylsulfonic acid, allyloxybenzenesulfonic acid, methallyloxy¬benzene¬sulfonic acid, 2-hydroxy-3-(2-propenyloxy)propanesulfonic acid, 2-methyl-2-propene-1¬sulfonic acid, styrenesulfonic acid, vinylsulfonic acid, 3-sulfopropyl acrylate, 3 sulfopropyl methacrylate, sulfomethacrylamide, sulfomethyl methacrylamide as well as mixtures of the aforementioned acids or their water-soluble salts.

The sulfonic acid groups in the polymers may be present entirely or partially in neutralized form, i.e., in some or all of the sulfonic acid groups, the acidic hydrogen atom in the sulfonic acid group may be replaced by metal ions, preferably alkali metal ions and in particular sodium ions. The use of copolymers containing partially or fully neutralized sulfonic acid groups is preferred according to the invention.

The monomer distribution in the copolymers preferred for use according to the invention is preferably 5% to 95% by weight in copolymers that contain only monomers containing carboxylic acid groups and monomers containing sulfonic acid groups, particularly preferably the amount of the monomer containing sulfonic acid groups is 50% to 90% by weight and the amount of the monomer containing carboxylic acid groups is 10% to 50% by weight and the monomers here are preferably selected from those listed above.

The molecular weight of the sulfo copolymers preferred for use according to the invention may be varied to adjust the properties of the polymers to the desired intended purpose. Preferred cleaning compositions are characterized in that the copolymers have molecular weights of 2000 to 200,000 gmol−1, preferably 4000 to 25,000 gmol−1 and in particular 5000 to 15,000 gmol−1.

In another preferred embodiment, the copolymers also comprise at least one nonionic, preferably hydrophobic, monomer in addition to the monomer that contains carboxyl groups and the monomer that contains sulfonic acid groups. The clear rinsing performance of automatic dishwasher detergents according to the invention has been improved by using these polymers in particular.

Anionic copolymers comprising monomers that contain carboxylic acid groups, monomers that contain sulfonic acid groups and nonionic monomers, in particular hydrophobic monomers, are therefore preferred according to the invention.

Preferably monomers of the general formula R1(R2)C=C(R3)-X—R4, in which R1 to R3 independently of one another stand for —H, —CH3 or —C2H5, X stands for a spacer group that is optionally present and is selected from —CH2-, —C(O)O— and C(O)—NH—, and R4 stands for a linear or branched saturated alkyl radical with 2 to 22 carbon atoms or for an unsaturated, preferably aromatic radical with 6 to 22 carbon atoms, are preferably used as the nonionic monomers.

Particularly preferred nonionic monomers include butene, isobutene, pentene, 3-methylbutene, 2-methylbutene, cyclopentene, hexene, 1-hexene, 2 methyl-1-pentene, 3-methyl-1-pentene, cyclohexene, methyl cyclopentene, cycloheptene, methyl cyclohexene, 2,4,4-trimethyl-1-pentene, 2,4,4-trimethyl-2 pentene, 2,3-dimethyl-1-hexene, 2,4-dimethyl-1-hexene, 2,5-dimethyl-1-hexene, 3,5-dimethyl-1-hexene, 4,4-dimethyl-1-hexane, ethyl cyclohexyne, 1-octene, α-olefins with 10 or more carbon atoms such as, for example, 1-decene, 1-dodecene, 1-hexadecene, 1-octadecene and C22 α-olefin, 2-styrene, α-methylstyrene, 3-methylstyrene, 4 propylstyrene, 4-cyclohexylstyrene, 4-dodecylstyrene, 2-ethyl-4-benzylstyrene, 1 vinylnaphthalene, 2-vinylnaphthalene, acrylic acid methyl ester, acrylic acid ethyl ester, acrylic acid propyl ester, acrylic acid butyl ester, acrylic acid pentyl ester, acrylic acid hexyl ester, methacrylic acid methyl ester, N (methyl)acrylamide, acrylic acid 2-ethylhexyl ester, methacrylic acid 2-ethyihexyl ester, N (2 ethylhexyl)acrylamide, acrylic acid octyl ester, methacrylic acid octyl ester, N (octyl)acrylamide, acrylic acid lauryl ester, methacrylic acid lauryl ester, N (lauryl)acrylamide, acrylic acid stearyl ester, methacrylic acid stearyl ester, N (stearyl)acrylamide, acrylic acid behenyl ester, methacrylic acid behenyl ester and N (behenyl)acrylamide or mixtures thereof.

The monomer distribution of the hydrophobically modified copolymers preferred for use according to the invention preferably amounts to 5% to 80% by weight, with respect to the monomers that contain sulfonic acid groups, the hydrophobic monomer and the monomer that contains carboxylic acid groups; the amount of the monomer that contains sulfonic acid groups and of the hydrophobic monomer is particularly preferably 5% to 30% by weight each, and the amount of the monomer that contains carboxylic acid groups is 60% to 80% by weight; the monomers here are preferably selected from those listed above.

Surprisingly, it has been found that a polypeptide of the invention in combination with a copolymer that comprises monomers that contain sulfonic acid groups (Sulfopolymer) in a dish washing composition, preferably an automatic dish washing composition has several advantages.

Firstly, the compositions do not only clean the dishes surprisingly better, show less filming on glasses, show less limescale accumulation, exhibit excellent shine after rinsing and show less deposits on the dish ware. These compositions also reduce the built up of mixed dirt in the interior of the dishwashing machine, especially the sieve.

Furthermore, the compositions contain specific enzyme stabilizing agents. It has been found that these combinations comprising a polypeptide of the invention in combination with a copolymer that comprises monomers that contain sulfonic acid groups (Sulfopolymer) show a better cleaning performance on enzyme related soil. This is due without being bound to the theory due to a better stabilization of the enzymes in the composition. This can be observed especially in dish washing composition that are in form of a liquid or a gel.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Adjunct Materials

Any detergent components known in the art for use in laundry/ADW/hard surface cleaning detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry/ADW/hard surface cleaning detergents may be utilized. The choice of such ingredients is well within the skill of the artisan.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3] triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Washing Method

The detergent compositions of the present invention are ideally suited for use in laundry applications. Accordingly, the present invention includes a method for laundering a fabric. The method comprises the steps of contacting a fabric to be laundered with a cleaning laundry solution comprising the detergent composition according to the invention. The fabric may comprise any fabric capable of being laundered in normal consumer use conditions. The solution preferably has a pH of from about 5.5 to about 8, further preferably pH selected in the range from about 7.5 to about 13.5, or in the range from about 7.5 to about 12.5, or in the range from about 8.5 to about 11.5, or in the range from about 9.5 to about 10.5, or pH 7.5 or above.

A preferred embodiment concerns a method of cleaning, the method comprising the steps of: contacting an object with a high pH cleaning composition (e.g. pH 7.5 or above) comprising a beta-glucanase of the invention under conditions suitable for cleaning the object. In a preferred embodiment the cleaning composition is used in a laundry or a dish wash process.

Still another embodiment relates to a method for removing stains from fabric or dishware which comprises contacting the fabric or dishware with a high pH cleaning composition (e.g. pH 7.5 or above) comprising a beta-glucanase of the invention under conditions suitable for cleaning the object.

Also contemplated are compositions and methods of treating fabrics (e.g., to desize a textile) using the cleaning composition of the invention. The high pH cleaning composition can be used in any fabric-treating method which is well known in the art.

In another embodiment the high pH cleaning composition of the present invention is suited for use in liquid laundry and liquid hard surface applications, including dish wash and car wash. Accordingly, the present invention includes a method for laundering a fabric or washing a hard surface. The method comprises the steps of contacting the fabric/dishware to be cleaned with a solution comprising the high pH cleaning composition according to the invention. The fabric may comprise any fabric capable of being laundered in normal consumer use conditions. The hard surface may comprise any dishware such as crockery, cutlery, ceramics, plastics such as melamine, metals, china, glass, acrylics or other hard surfaces such as cars, floors etc. The solution preferably has a pH, e.g. 7.5 or above, e.g. from about 9 to about 13.5.

The compositions may be employed at concentrations of from about 100 ppm, preferably 500 ppm to about 15,000 ppm in solution. The water temperatures typically range from about 5° C. to about 90° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8. In preferred embodiments the washing method is conducted at a pH selected in the range from about 7.5 to about 13.5, or in the range from about 7.5 to about 12.5, or in the range from about 8.5 to about 11.5, or in the range from about 9.5 to about 10.5, or pH 7.5 or above.

In some preferred embodiments, the high pH cleaning compositions provided herein are typically formulated such that, during use in aqueous cleaning operations, the wash water has a pH of from about 9 to about 13.5, or in alternative embodiments, or from about 10 to about 13.5 even from about 11 to about 13.5. In some preferred embodiments the liquid laundry products are formulated to have a pH from about 12 to about 13.5. Techniques for controlling pH at recommended usage levels include the use of buffers, acids, alkalis, etc., and are well known to those skilled in the art. In the context of the present invention alkalis are used to adjust pH to about 9 to 13.5 preferably about 10 to 13.5.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11 dH, about 12° dH, about 13° dH, about 14° dH, about 15° dH, about 16° dH, about 17° dH, about 18° dH, about 19° dH, about 20° dH, about 21 dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present invention relates to a method of cleaning a fabric, a dishware or hard surface with a detergent composition comprising a beta-glucanase of the invention.

A preferred embodiment concerns a method of cleaning, said method comprising the steps of: contacting an object with a cleaning composition comprising a beta-glucanase of the invention under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition comprising a beta-glucanase of the invention under conditions suitable for cleaning said object.

Low Temperature Uses

One embodiment of the invention concerns a method of doing laundry, dish wash or industrial cleaning comprising contacting a surface to be cleaned with a beta-glucanase of the invention, and wherein said laundry, dish wash, industrial or institutional cleaning is performed at a temperature of about 40° C. or below. One embodiment of the invention relates to the use of a beta-glucanase in laundry, dish wash or a cleaning process wherein the temperature in laundry, dish wash, industrial cleaning is about 40° C. or below In another embodiment, the invention concerns the use of a beta-glucanase according to the invention in a beta-glucan removing process, wherein the temperature in the beta-glucan removing process is about 40° C. or below.

In each of the above-identified methods and uses, the wash temperature is about 40° C. or below, such as about 39° C. or below, such as about 38° C. or below, such as about 37° C. or below, such as about 36° C. or below, such as about 35° C. or below, such as about 34° C. or below, such as about 33° C. or below, such as about 32° C. or below, such as about 31° C. or below, such as about 30° C. or below, such as about 29° C. or below, such as about 28° C. or below, such as about 27° C. or below, such as about 26° C. or below, such as about 25° C. or below, such as about 24° C. or below, such as about 23° C. or below, such as about 22° C. or below, such as about 21° C. or below, such as about 20° C. or below, such as about 19° C. or below, such as about 18° C. or below, such as about 17° C. or below, such as about 16° C. or below, such as about 15C or below, such as about 14° C. or below, such as about 13° C. or below, such as about 12° C. or below, such as about 11° C. or below, such as about 10° C. or below, such as about 9° C. or below, such as about 8° C. or below, such as about 7° C. or below, such as about 6° C. or below, such as about 5° C. or below, such as about 4° C. or below, such as about 3° C. or below, such as about 2° C. or below, such as about 1° C. or below.

In another preferred embodiment, the wash temperature is in the range of about 5-40° C., such as about 5-30° C., about 5-20° C., about 5-10° C., about 10-40° C., about 10-30° C., about 10-20° C., about 15-40° C., about 15-30° C., about 15-20° C., about 20-40° C., about 20-30° C., about 25-40° C., about 25-30° C., or about 30-40° C. In particular preferred embodiments the wash temperature is about 20° C., about 30° C., or about 40° C.

High Temperature Uses

One embodiment of the invention concerns a method of doing laundry, dish wash or industrial cleaning comprising contacting a surface to be cleaned with a beta-glucanase of the invention, and wherein said laundry, dish wash, industrial or institutional cleaning is performed at a temperature of about 75° C. or below. One embodiment of the invention relates to the use of a beta-glucanase in laundry, dish wash or a cleaning process wherein the temperature in laundry, dish wash, industrial cleaning is about 70° C. or below.

In another embodiment, the invention concerns the use of a beta-glucanase according to the invention in a beta-glucan removing process, wherein the temperature in the beta-glucan removing process is about 65° C. or below.

In each of the above-identified methods and uses, the wash temperature is about 60° C. or below, such as about 59° C. or below, such as about 58° C. or below, such as about 57° C. or below, such as about 56° C. or below, such as about 55° C. or below, such as about 54° C. or below, such as about 53° C. or below, such as about 52° C. or below, such as about 51° C. or below, such as about 50° C. or below, such as about 49° C. or below, such as about 48° C. or below, such as about 47° C. or below, such as about 46° C. or below, such as about 45° C. or below, such as about 44° C. or below, such as about 43° C. or below, such as about 42° C. or below, such as about 41° C. or below.

In another preferred embodiment, the wash temperature is in the range of about 41-90° C., such as about 41-80° C., about 41-85° C., about 41-80° C., about 41-75° C., about 41-70° C., about 41-65° C., about 41-60° C.

Methods for Reducing or Preventing Soil Redeposition Using a Polypeptide(s) or Detergent Composition Comprising a Polypeptide(s) of the Present Invention An embodiment of the invention is a method for reducing or preventing soil redeposition using a detergent composition comprising a polypeptide(s) of the invention.

In one embodiment, the detergent composition further comprises one or more detergent components selected from the group comprising surfactants, builders, hydrotopes, bleaching systems, polymers, fabric hueing agents, adjunct materials, dispersants, dye transfer inhibiting agents, fluorescent whitening agents and soil release polymers, or any mixture thereof. The detergent composition may be in the form of a bar, a homogenous tablet, a tablet having two or more layers, a pouch having one or more compartments, the compartment(s) containing one or more different phases, a regular or compact powder, a granulate, a paste, a gel, or a regular, compact or concentrated liquid, two or more liquids and/or gels in a multichamber-bottle and may be used for dish wash or laundering.

In another embodiment, the detergent composition comprises one or more additional enzymes selected from the group comprising proteases, amylases, lipases, cutinases, cellulases, endoglucanases, xyloglucanases, pectinases, pectin lyases, xanthanases, peroxidaes, haloperoxygenases, catalases and mannanases, or any mixture thereof.

In a further embodiment, the detergent composition comprises one or more detergent components selected from the group comprising surfactants, builders, hydrotopes, bleaching systems, polymers, fabric hueing agents, adjunct materials, dispersants, dye transfer inhibiting agents, fluorescent whitening agents and soil release polymers, or any mixture thereof and one or more additional enzymes selected from the group comprising proteases, amylases, lipases, cutinases, cellulases, endoglucanases, xyloglucanases, pectinases, pectin lyases, xanthanases, peroxidaes, haloperoxygenases, catalases and mannanases, or any mixture thereof.

The method may comprise the following steps:
 (a) providing a wash liquor by dissolving/mixing the detergent composition in water;
 (b) washing the objects/fabrics/textiles in the wash liquor;
 (c) draining the wash liquor and optionally repeating the wash cycle; and
 (d) rinsing and optionally drying the objects/fabrics/textiles.

In a preferred embodiment the method may comprise the following steps:
 (1) providing water and rinsing the objects
 (2) optionally, draining the water and providing fresh water
 (3) dosing the detergent composition into the water to form a wash liquor
 (4) agitating the wash liquor, thereby washing the objects, optionally heating the liquor
 (5) draining the wash liquor
 (6) optionally providing fresh water, rinsing the objects, and draining the liquid
 (7) optionally providing fresh water, rinsing the objects, and during this step dosing an optional additional agent into the liquor, e.g. a rinse-aid, optionally heating the liquor, and afterwards draining the liquor.
 (8) optionally letting remaining liquid evaporate from the objects.

A preferred embodiment of the invention is a method for reducing soil redeposition using a detergent composition comprising: a polypeptide(s) having beta-glucanase activity, selected from the group consisting of:

(a) a polypeptide having at least 60% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;
 (b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);
 (c) a polypeptide encoded by a polynucleotide having at least 60% sequence identity to the mature polypeptide coding sequence of the sequence selected from the group consisting of: SEQ ID NO: 1, SEQ ID NO: 4, SEQ ID NO: 6, SEQ ID NO: 8;
 (d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
 (e) a fragment of the polypeptide of (a), (b), (c), or (d) that has beta-glucanase activity A preferred embodiment of the invention is a method for reducing soil redeposition using a detergent composition comprising: a polypeptide(s) having beta-glucanase activity, selected from the group consisting of:

(a) a polypeptide having at least 60% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;
 (b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);
 (c) a polypeptide encoded by a polynucleotide having at least 60% sequence identity to the mature polypeptide coding sequence of the sequence selected from the group consisting of: SEQ ID NO: 1, SEQ ID NO: 4, SEQ ID NO: 6, SEQ ID NO: 8;
 (d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
 (e) a fragment of the polypeptide of (a), (b), (c), or (d) that has beta-glucanase activity; wherein said cleaning or detergent composition further comprising:
 (i) one or more amylases; and/or
 (ii) one or more proteases.

The Invention is Further Defined in the Following Paragraphs:

1. A polypeptide having beta-glucanase activity, selected from the group consisting of:
 (a) a polypeptide having at least 60% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;
 (b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);
 (c) a polypeptide encoded by a polynucleotide having at least 60% sequence identity to the mature polypeptide coding sequence of the sequence selected from the group consisting of: SEQ ID NO: 1, SEQ ID NO: 4, SEQ ID NO: 6, SEQ ID NO: 8;

(d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity; preferably said beta-glucanase activity is not an endo-cellulase activity on β-1,4 linkages between D-glucose units of cellulose.

2. The polypeptide of paragraph 1, having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of the sequence selected from the group consisting of: SEQ ID NO: 2, SEQ ID NO: 3, SEQ ID NO: 5, SEQ ID NO: 7, SEQ ID NO: 9.

3. The polypeptide of paragraph 1 or 2, which is encoded by a polynucleotide that hybridizes under low stringency conditions, low-medium stringency conditions, medium stringency conditions, medium-high stringency conditions, high stringency conditions, or very high stringency conditions with (i) the mature polypeptide coding sequence of the sequence selected from the group consisting of: SEQ ID NO: 1, SEQ ID NO: 4, SEQ ID NO: 6, SEQ ID NO: 8; or (ii) the full-length complement of (i).

4. The polypeptide of any of paragraphs 1-3, which is encoded by a polynucleotide having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide coding sequence of the sequence selected from the group consisting of: SEQ ID NO: 1, SEQ ID NO: 4, SEQ ID NO: 6, SEQ ID NO: 8.

5. The polypeptide of any of paragraphs 1-4, comprising or consisting of i) the sequence selected from the group consisting of: SEQ ID NO: 2, SEQ ID NO: 3, SEQ ID NO: 5, SEQ ID NO: 7, SEQ ID NO: 9; or ii) the mature polypeptide of the sequence selected from the group consisting of SEQ ID NO: 2, SEQ ID NO: 3, SEQ ID NO: 5, SEQ ID NO: 7, SEQ ID NO: 9.

6. The polypeptide of paragraph 5, wherein the mature polypeptide is selected from the group consisting of: amino acids 1 to 351 of SEQ ID NO: 2, amino acids 1 to 351 of SEQ ID NO: 3, amino acids 1 to 245 of SEQ ID NO: 5, amino acids 1 to 222 of SEQ ID NO: 7, amino acids 1 to 214 of SEQ ID NO: 9.

7. The polypeptide of any of paragraphs 1-4, which is a variant of the mature polypeptide of the sequence selected from the group consisting of: i) SEQ ID NO: 2, ii) SEQ ID NO: 3, iii) SEQ ID NO: 5, iv) SEQ ID NO: 7, v) SEQ ID NO: 9; wherein said variant comprising a substitution, deletion, and/or insertion at one or more positions.

8. The polypeptide of paragraph 1, which is a fragment of the sequence selected from the group consisting of: SEQ ID NO: 2, SEQ ID NO: 3, SEQ ID NO: 5, SEQ ID NO: 7, SEQ ID NO: 9, wherein the fragment has beta-glucanase activity.

9. The polypeptide of any of paragraphs 1-8, wherein said polypeptide is capable of having beta-glucanase activity in an aqueous solution with a pH selected in the range from about 7.5 to about 13.5, wherein said aqueous solution optionally comprises a bleaching agent, preferably said pH is selected in the range from about 7.5 to about 12.5, further preferably said pH is selected in the range from about 8.5 to about 11.5, most preferably said pH is selected in the range from about 9.5 to about 10.5.

10. The polypeptide of any of paragraphs 1-9, wherein said polypeptide is capable of having beta-glucanase activity in an aqueous solution at a temperature selected in the range from about 20° C. to about 75° C., wherein said aqueous solution optionally comprises a bleaching agent, preferably said temperature is selected in the range from about 40° C. to about 60° C.

11. The polypeptide of any of paragraphs 9-10, wherein said polypeptide is capable of having beta-glucanase activity for at least 15 minutes, preferably for 30 minutes.

12. The polypeptide of any of paragraphs 1-11, wherein said beta-glucanase activity comprises alkaline beta-glucanase activity, wherein said alkaline beta-glucanase activity is beta-glucanase activity at pH 7.5 or above.

13. The polypeptide of any of paragraphs 1-12, wherein said beta-glucanase activity comprises licheninase EC 3.2.1.73 activity, preferably said beta-glucanase activity is licheninase EC 3.2.1.73 activity.

14. A composition comprising one or more polypeptides of any of paragraphs 1-13, preferably said composition is not a dish wash composition.

15. The composition of paragraph 14, further comprising one or more detergent components.

16. The composition of paragraph 15, wherein the detergent component is selected from the group consisting of: surfactants, hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants, and solubilizers.

17. The composition of any of paragraphs 14-16, further comprising one or more additional enzymes, preferably said one or more additional enzymes is:

i) one or more amylases, further preferably said one or more amylases is one or more alpha-amylases; or ii) one or more proteases; or iii) one or more amylases as in (i) and one or more proteases.

18. The composition of any of paragraphs 14-17, further comprising an enzyme selected from the group consisting of: DNases, perhydrolases, amylases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, and combinations thereof.

19. The composition of any of paragraphs 14-18, wherein said composition has pH of 7.5 or above and optionally, comprises a bleaching agent; preferably said pH is selected in the range from about 7.5 to about 13.5, further preferably said pH is selected in the range from about 7.5 to about 12.5, most preferably said pH is selected in the range from about 8.5 to about 11.5, further most preferably said pH is selected in the range from about 9.5 to about 10.5.

20. The composition of any of paragraphs 14-19, wherein said composition has improved stability and/or performance under alkaline conditions, preferably said alkaline conditions have pH 7.5 or above.

21. The composition of any of paragraphs 14-20, wherein said composition is a cleaning or detergent composition, preferably said cleaning or detergent composition is not a dish wash composition.

22. Use of one or more polypeptides of any of paragraphs 1-13 or the composition of any of paragraphs 14-21 for degrading a beta-glucan, preferably said beta-glucan is a beta-D-glucan, further preferably said beta-glucan is a beta-1,3-1,4 glucan, most preferably said beta-glucan is a mix-linkage beta-glucan, further most preferably said beta-glucan is a barley beta-glucan or oatmeal beta-glucan (e.g., from cooked oats and/or from cooked and burned-in oats and/or from uncooked oats); optionally said use is carried out under alkaline conditions having pH 7.5 or above.

23. Use of one or more polypeptides of any of paragraphs 1-13 or the composition of any of paragraphs 14-21 for washing or cleaning a textile and/or a hard surface such as dish wash including Automatic Dish Wash (ADW), preferably said washing or cleaning is washing or cleaning of cooked oats and/or cooked and burned-in oats and/or uncooked oats; optionally said use is carried out under alkaline conditions having pH 7.5 or above, preferably said use is not use in dish wash.

24. Use of one or more polypeptides of any of paragraphs 1-13 or the composition of any of paragraphs 14-21 in a cleaning process such as laundry or hard surface cleaning including dish wash including Automatic Dish Wash (ADW) and industrial cleaning; optionally said use is carried out under alkaline conditions having pH 7.5 or above, preferably said use is not use in dish wash.

25. Use of one or more polypeptides of any of paragraphs 1-13 or the composition of any of paragraphs 14-21 for laundering and/or hard surface cleaning including dish wash including Automatic Dish Wash (ADW), wherein said polypeptide or said composition has an enzyme detergency benefit; optionally said use is carried out under alkaline conditions having pH 7.5 or above, preferably said use is not use in dish wash.

26. Use of one or more polypeptides of any of paragraphs 1-13 or the composition of any of paragraphs 14-21 for at least one of the following: preventing, reducing or removing a biofilm from an item, preferably a malodor is reduced or removed from said item; optionally said use is carried out under alkaline conditions having pH 7.5 or above, preferably said use is not use in dish wash.

27. A process of degrading a beta-glucan comprising applying one or more polypeptides of any of paragraphs 1-13 or a composition of any of paragraphs 14-21 to said beta-glucan, preferably said beta-glucan is a beta-D-glucan, further preferably said beta-glucan is a beta-1,3-1,4 glucan, most preferably said beta-glucan is a mix-linkage beta-glucan, further most preferably said beta-glucan is a barley beta-glucan or oatmeal beta-glucan (e.g., from cooked oats and/or from cooked and burned-in oats and/or from uncooked oats); optionally, said process is carried out under alkaline conditions having pH 7.5 or above, preferably said process is not dish wash process.

28. The process of paragraph 27, wherein said beta-glucan is on the surface of a textile or hard surface, such as dish wash, preferably said beta-glucan is from cooked oats and/or from cooked and burned-in oats and/or from uncooked oats.

29. A fermentation broth formulation or cell culture composition comprising one or more polypeptides of any of paragraphs 1-13.

30. A polynucleotide encoding the polypeptide of any of paragraphs 1-13.

31. A nucleic acid construct or expression vector capable of expressing a polynucleotide of paragraph 30, preferably said nucleic acid construct or said expression vector comprising the polynucleotide of paragraph 30 operably linked to one or more control sequences that direct the production of the polypeptide in an expression host.

32. A recombinant host cell comprising the polynucleotide of paragraph 30, preferably said polynucleotide is operably linked to one or more control sequences that direct the production of the polypeptide, further preferably said recombinant host cell is an isolated recombinant host cell, further most preferably said recombinant host cell is a heterologous host cell (e.g., a host cell that is not a *Bacillus agaradhaerens* host cell or a host cell that is not a *Bacillus* sp-62449 host cell or a host cell that is not a *Bacillus akibai* host cell or a host cell that is not a *Bacillus mojavensis* host cell).

33. A composition comprising at least one of the following: i) a polynucleotide of paragraph 30; or ii) a nucleic acid construct of paragraph 31; or iii) an expression vector of paragraph 31.

34. A method for producing the polypeptide of any of paragraphs 1-13, comprising cultivating a cell, which in its wild-type form produces the polypeptide, under conditions conducive for production of the polypeptide.

35. The method of paragraph 34, further comprising recovering the polypeptide.

36. A method for producing a polypeptide having beta-glucanase activity, comprising cultivating the host cell of paragraph 32 under conditions conducive for production of the polypeptide.

37. The method of paragraph 36, further comprising recovering the polypeptide.

38. A transgenic plant, plant part or plant cell transformed with a polynucleotide encoding the polypeptide of any of paragraphs 1-13.

39. A method for producing a polypeptide having beta-glucanase activity, comprising cultivating the transgenic plant or plant cell of paragraph 38 under conditions conducive for production of the polypeptide.

40. The method of paragraph 39, further comprising recovering the polypeptide.

41. A polypeptide having beta-glucanase activity, wherein said polypeptide is selected from the group consisting of:
(a) a polypeptide having at least 89% sequence identity to the mature polypeptide of the sequence selected from the group consisting of: SEQ ID NO: 7, SEQ ID NO: 2, SEQ ID NO: 3, SEQ ID NO: 5, SEQ ID NO: 9;
(b) a polypeptide encoded by a polynucleotide having at least 89% sequence identity to the mature polypeptide coding sequence of the sequence selected from the group consisting of: SEQ ID NO: 6, SEQ ID NO: 1, SEQ ID NO: 4, SEQ ID NO: 8.

42. The polypeptide of paragraph 41, having at least 90%, at least 91%, at least 92%, at least 93%, at least 94%, at least 95%, at least 96%, at least 97%, at least 98%, at least 99% or 100% sequence identity to the mature polypeptide of the sequence selected from the group consisting of: SEQ ID NO: 7, SEQ ID NO: 2, SEQ ID NO: 3, SEQ ID NO: 5, SEQ ID NO: 9.

43. The polypeptide of any of paragraphs 41-42, wherein the mature polypeptide is selected from the group consisting of: amino acids 1 to 222 of SEQ ID NO: 7, amino acids 1 to 351 of SEQ ID NO: 2, amino acids 1 to 351 of SEQ ID NO: 3, amino acids 1 to 245 of SEQ ID NO: 5, amino acids 1 to 214 of SEQ ID NO: 9.

44. The polypeptide of any of paragraphs 41-43, wherein said polypeptide is capable of:
  i) having beta-glucanase activity for at least 15 minutes in an aqueous solution with a pH selected in the range from about 7.5 to about 13.5, wherein said aqueous solution optionally comprises a bleaching agent, preferably said pH is selected in the range from about 7.5 to about 12.5, further preferably said pH is selected in the range from about 8.5 to about 11.5, most preferably said pH is selected in the range from about 9.5 to about 10.5; and/or
  ii) having beta-glucanase activity for at least 15 minutes in an aqueous solution at a temperature selected in the range from about 20° C. to about 75° C., wherein said aqueous solution optionally comprises a bleaching agent.

45. The polypeptide of any of paragraphs 41-44, wherein said beta-glucanase activity comprises licheninase EC 3.2.1.73 activity.

46. The polypeptide of paragraph 45, wherein said beta-glucanase activity is licheninase EC 3.2.1.73 activity.

47. A composition comprising one or more polypeptides of any of paragraphs 41-46, preferably said composition is not a dish wash composition.

48. The composition of paragraph 47, further comprising:
  i) one or more detergent components; and/or
  ii) one or more additional enzymes, preferably said one or more additional enzymes is:
    a) one or more amylases, further preferably said one or more amylases is one or more alpha-amylases; or
    b) one or more proteases; or
    c) one or more amylases as in (a) and one or more proteases.

49. The composition of any of paragraphs 47-48, wherein said composition has pH of 7.5 or above and optionally comprises a bleaching agent; preferably said pH is selected in the range from about 7.5 to about 13.5, further preferably said pH is selected in the range from about 7.5 to about 12.5, most preferably said pH is selected in the range from about 8.5 to about 11.5, further most preferably said pH is selected in the range from about 9.5 to about 10.5.

50. The composition of any of paragraphs 47-49, wherein said composition is a cleaning or a detergent composition, preferably said cleaning or detergent composition is not a dish wash composition.

51. Use of one or more polypeptides of any of paragraphs 41-46 or the composition of any of paragraphs 47-50 in a cleaning process such as laundry or hard surface cleaning including dish wash; optionally said use is carried out under alkaline conditions having pH 7.5 or above.

52. A fermentation broth formulation or cell culture composition comprising one or more polypeptides of any of paragraphs 41-46.

53. A polynucleotide encoding one or more polypeptides of any of paragraphs 41-46.

54. A nucleic acid construct or expression vector capable of expressing a polynucleotide of paragraph 53, preferably said nucleic acid construct or said expression vector comprising the polynucleotide of paragraph 53 operably linked to one or more control sequences that direct the production of the polypeptide in an expression host.

55. A recombinant host cell comprising one or more polynucleotides of paragraph 53, preferably said polynucleotide is operably linked to one or more control sequences that direct the production of the polypeptide, further preferably said recombinant host cell is an isolated recombinant host cell, further most preferably said recombinant host cell is a heterologous host cell (e.g., a host cell that is not a *Bacillus agaradhaerens* host cell or a host cell that is not a *Bacillus* sp-62449 host cell or a host cell that is not a *Bacillus akibai* host cell or a host cell that is not a *Bacillus mojavensis* host cell).

56. A cleaning or detergent composition comprising one or more polypeptides having beta-glucanase activity, selected from the group consisting of:
  (a) a polypeptide having at least 60% sequence identity to the mature polypeptide of the sequence selected from the group consisting of: SEQ ID NO: 2, SEQ ID NO: 3, SEQ ID NO: 5, SEQ ID NO: 7, SEQ ID NO: 9;
  (b) a polypeptide encoded by a polynucleotide that hybridizes under low stringency conditions with (i) the mature polypeptide coding sequence of the sequence selected from the group consisting of: SEQ ID NO: 1, SEQ ID NO: 4, SEQ ID NO: 6, SEQ ID NO: 8, or (ii) the full-length complement of (i);
  (c) a polypeptide encoded by a polynucleotide having at least 60% sequence identity to the mature polypeptide coding sequence of the sequence selected from the group consisting of: SEQ ID NO: 1, SEQ ID NO: 4, SEQ ID NO: 6, SEQ ID NO: 8;
  (d) a variant of the mature polypeptide of the sequence selected from the group consisting of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
  (e) a fragment of the polypeptide of (a), (b), (c), or (d) that has beta-glucanase activity; and
  (i) one or more amylases; and/or
  (ii) one or more proteases,
  preferably said polypeptide having beta-glucanase activity and said one or more amylases and/or one or more proteases have a synergistic effect; further preferably said synergistic effect is a REM synergistic effect, further most preferably said REM synergistic effect is of more than 6.5 at about 40° C. for about 30 minutes at pH of about 7.5, further most preferably said REM synergistic effect is of more than 6.1 at about 40° C. for about 30 minutes at pH of about 10, further most preferably said REM synergistic effect is of more than 6.2 at about 40° C. for about 30 minutes at pH of about 10, further most preferably said beta-glucanase activity is not an endo-cellulase activity on β-1,4 linkages between D-glucose units of cellulose;
  preferably said cleaning or detergent composition is not a dish wash composition.

57. The cleaning or detergent composition of paragraph 56, wherein said polypeptide has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of the sequence selected from the group consisting of: SEQ ID NO: 2, SEQ ID NO: 3, SEQ ID NO: 5, SEQ ID NO: 7, SEQ ID NO: 9.

58. The cleaning or detergent composition of paragraph 57 or 58, wherein said polypeptide is encoded by a polynucleotide that hybridizes under low stringency conditions, low-medium stringency conditions, medium stringency conditions, medium-high stringency conditions, high stringency conditions, or very high stringency conditions with (i) the mature polypeptide coding sequence of the sequence selected from the group consisting of: SEQ ID NO: 1, SEQ ID NO: 4, SEQ ID NO: 6, SEQ ID NO: 8; or (ii) the full-length complement of (i).

59. The cleaning or detergent composition of any of paragraphs 56-58, wherein said polypeptide is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide coding sequence of the sequence selected from the group consisting of: SEQ ID NO: 1, SEQ ID NO: 4, SEQ ID NO: 6, SEQ ID NO: 8.

60. The cleaning or detergent composition of any of paragraphs 56-59, wherein said polypeptide comprises or consists of: i) the sequence selected from the group consisting of: SEQ ID NO: 2, SEQ ID NO: 3, SEQ ID NO: 5, SEQ ID NO: 7, SEQ ID NO: 9; or ii) the mature polypeptide of the sequence selected from the group consisting of: SEQ ID NO: 2, SEQ ID NO: 3, SEQ ID NO: 5, SEQ ID NO: 7, SEQ ID NO: 9.

61. The cleaning or detergent composition of paragraph 60, wherein the mature polypeptide is selected from the group consisting of: i) amino acids 1 to 351 of SEQ ID NO: 2, ii) amino acids 1 to 351 of SEQ ID NO: 3, iii) amino acids 1 to 245 of SEQ ID NO: 5, iv) amino acids 1 to 222 of SEQ ID NO: 7, v) amino acids 1 to 214 of SEQ ID NO: 9.

62. The cleaning or detergent composition of any of paragraphs 56-59, wherein said polypeptide is a variant of the mature polypeptide of the sequence selected from the group consisting of: i) SEQ ID NO: 2, ii) SEQ ID NO: 3, iii) SEQ ID NO: 5, iv) SEQ ID NO: 7, v) SEQ ID NO: 9; wherein said variant comprising a substitution, deletion, and/or insertion at one or more positions.

63. The cleaning or detergent composition of paragraph 56, wherein said polypeptide is a fragment of the sequence selected from the group consisting of: SEQ ID NO: 2, SEQ ID NO: 3, SEQ ID NO: 5, SEQ ID NO: 7, SEQ ID NO: 9, wherein the fragment has beta-glucanase activity.

64. The cleaning or detergent composition of any of paragraphs 56-63, wherein said polypeptide is capable of having beta-glucanase activity in an aqueous solution with a pH in the range from about 7.5 to about 13.5, wherein said aqueous solution optionally comprises a bleaching agent, preferably said pH is in the range from about 7.5 to about 12.5, further preferably said pH is in the range from about 8.5 to about 11.5, most preferably said pH is in the range from about 9.5 to about 10.5.

65. The cleaning or detergent composition of any of paragraphs 56-64, wherein said polypeptide is capable of showing beta-glucanase activity in an aqueous solution at a temperature selected in the range from about 20° C. to about 75° C., and/or in the range from about 40° C. to about 60° C., wherein said aqueous solution optionally comprises a bleaching agent.

66. The cleaning or detergent composition of any of paragraphs 64-65, wherein said polypeptide is capable of having beta-glucanase activity for at least 15 minutes, preferably for at least 30 minutes.

67. The cleaning or detergent composition of any of paragraphs 56-66, wherein said beta-glucanase activity comprises alkaline beta-glucanase activity, wherein said alkaline beta-glucanase activity is beta-glucanase activity at pH 7.5 or above.

68. The cleaning or detergent composition of any of paragraphs 56-67, wherein said beta-glucanase activity comprises licheninase EC 3.2.1.73 activity, preferably said beta-glucanase activity is licheninase EC 3.2.1.73 activity.

69. The cleaning or detergent composition of any of paragraphs 56-68, wherein said amylase is an alpha-amylase.

70. The cleaning or detergent composition of any of paragraphs 56-69, further comprising one or more detergent components.

71. The cleaning or detergent composition of paragraph 70, wherein the detergent component is selected from the group consisting of: surfactants, hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants, and solubilizers.

72. The cleaning or detergent composition of any of paragraphs 56-71, further comprising one or more additional enzymes.

73. The cleaning or detergent composition of any of paragraphs 56-72, further comprising an enzyme selected from the group consisting of: DNases, perhydrolases, amylases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, and combinations thereof.

74. The cleaning or detergent composition of any of paragraphs 56-73, wherein said composition has pH of 7.5 or above and optionally, comprises a bleaching agent; preferably said pH is selected in the range from about 7.5 to about 13.5, further preferably said pH is selected in the range from about 7.5 to about 12.5, most preferably said pH is selected in the range from about 8.5 to about 11.5, further most preferably said pH is selected in the range from about 9.5 to about 10.5.

75. The cleaning or detergent composition of any of paragraphs 69-74, wherein said alpha-amylase is selected from the group consisting of:
(a) a polypeptide having at least 90% sequence identity to SEQ ID NO: 13 (corresponding to SEQ ID NO: 2 of WO 95/10603);

(b) a polypeptide having at least 90% sequence identity to SEQ ID NO: 13 (corresponding to SEQ ID NO: 2 in WO 95/10603) wherein the polypeptide comprises a substitution in one or more of positions: 15, 23, 105, 106, 124, 128, 133, 154, 156, 178, 179, 181, 188, 190, 197, 201, 202, 207, 208, 209, 211, 243, 264, 304, 305, 391, 408, and/or 444; (c) a polypeptide having at least 90% sequence identity to SEQ ID NO: 14 (corresponding to SEQ ID NO: 6 in WO 02/010355);

(d) a polypeptide having at least 90% sequence identity to the hybrid polypeptide of SEQ ID NO: 15 (comprising residues 1-33 of SEQ ID NO: 6 of WO 2006/066594 and residues 36-483 of SEQ ID NO: 4 of WO 2006/066594);

(e) a polypeptide having at least 90% sequence identity to the hybrid polypeptide of SEQ ID NO: 15 (comprising residues 1-33 of SEQ ID NO: 6 of WO 2006/066594 and residues 36-483 of SEQ ID NO: 4 of WO 2006/066594), wherein the hybrid polypeptide comprises a substitution, a deletion or an insertion in one of more of positions: 48, 49, 107, 156, 181, 190, 197, 201, 209 and/or 264;

(f) a polypeptide having at least 90% sequence identity to SEQ ID NO: 16 (corresponding to SEQ ID NO: 6 of WO 02/019467);

(g) a polypeptide having at least 90% sequence identity to SEQ ID NO: 16 (corresponding to SEQ ID NO: 6 of WO 02/019467), wherein the polypeptide comprises a substitution, a deletion or an insertion in one of more of positions: 181, 182, 183, 184, 195, 206, 212, 216 and/or 269;

(h) a polypeptide having at least 90% sequence identity to SEQ ID NO: 17, SEQ ID NO: 18 or SEQ ID NO: 19 (corresponding to SEQ ID NO: 1, SEQ ID NO: 2 or SEQ ID NO: 7 of WO 96/023873)

(i) a polypeptide having at least 90% sequence identity to SEQ ID NO: 17, SEQ ID NO: 18 or SEQ ID NO: 19 (corresponding to SEQ ID NO: 1, SEQ ID NO: 2 or SEQ ID NO: 7 of WO 96/023873), wherein the polypeptide comprises a substitution, a deletion or an insertion in one of more of positions: 140, 183, 184 195, 206, 243, 260, 304 and/or 476;

(j) a polypeptide having at least 90% sequence identity to SEQ ID NO: 20 (corresponding to SEQ ID NO: 2 of WO 08/153815);

(k) a polypeptide having at least 90% sequence identity to SEQ ID NO: 21 (corresponding to SEQ ID NO: 10 of WO 01/66712);

(l) a polypeptide having at least 90% sequence identity to SEQ ID NO: 21 (corresponding to SEQ ID NO: 10 of WO 01/66712), wherein the polypeptide comprises a substitution, a deletion or an insertion in one of more of positions: 176, 177, 178, 179, 190, 201, 207, 211 and/or 264;

(m) a polypeptide having at least 90% sequence identity to SEQ ID NO: 22 (corresponding to SEQ ID NO: 2 of WO 09/061380);

(n) a polypeptide having at least 90% sequence identity to SEQ ID NO: 22 (corresponding to SEQ ID NO: 2 of WO 09/061380), wherein the polypeptide comprises a substitution, a deletion or an insertion in one of more of positions: 87, 98, 125, 128, 131, 165, 178, 180, 181, 182, 183, 201, 202, 225, 243, 272, 282, 305, 309, 319, 320, 359, 444 and/or 475; (o) a polypeptide having at least 90% sequence identity to SEQ ID NO: 21, wherein the polypeptide comprises a substitution, a deletion or an insertion in one of more of positions: 28, 118, 174; 181, 182, 183, 184, 186, 189, 195, 202, 298, 299, 302, 303, 306, 310, 314; 320, 324, 345, 396, 400, 439, 444, 445, 446, 449, 458, 471 and/or 484; and (p) a polypeptide having at least 90% sequence identity to SEQ ID NO: 12;

(q) a variant of SEQ ID NO:23 having alterations G182*+D183*;

(r) a variant of SEQ ID NO:24 having alterations H183*+G184*+I405L+A421H+A422P+A428T;

(s) a variant of SEQ ID NO:24 having alterations M9L+R118K+G149A+G182T+G186A+D183*+G184*+N195F+M202L+T257I+Y295F+N299Y+R320K+M323T+A339S+E345R+R458K;

(t) a variant of SEQ ID NO: 24 having alterations R178*+G179*+E187P+I203Y+R458N+T459S+D460T+G476K (u) a variant of SEQ ID NO: 27 having alteration M202L;

(v) a variant of SEQ ID NO: 28 having alterations R180*+S181*+S243Q+G475K;

(w) a variant of SEQ ID NO: 29 having alterations D183*+G184*+W140Y+N195F+I206Y+Y243F+E260G+G304R+G476K;

(x) a variant of SEQ ID NO: 30 having alterations H1*+N54S+V56T+K72R+G109A+F113Q+R116Q+W167F+Q172G+A174S+G184T+N195F+V206L+K391A+P473R+G476K;

(y) a variant of SEQ ID NO: 31 having alterations M9L+R118K+G149A+G182T+G186A+D183*+G184*+N195F+T246V+T257I+Y295F+N299Y+R320K+M323T+A339S+E345R+R458K.

76. The cleaning or detergent composition of any of paragraphs 56-75, wherein said protease is selected from the group consisting of:

1) a polypeptide having protease activity, which has at least 60% sequence identity (e.g., at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity) to SEQ ID NO: 34;

2) a polypeptide having protease activity, which has at least 60% sequence identity (e.g., at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity) to SEQ ID NO: 35;

3) a polypeptide having protease activity, which has at least 60% sequence identity (e.g., at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity) to SEQ ID NO: 36.

77. The cleaning or detergent composition of any of paragraphs 56-76, wherein said composition has improved stability and/or performance under alkaline conditions, preferably said alkaline conditions have pH 7.5 or above.

78. The cleaning or detergent composition of any of paragraphs 56-77, wherein said composition is in form selected from a group consisting of: a bar, a homogenous tablet, a tablet having two or more layers, a pouch having one or more compartments, a regular or compact powder, a granule, a paste, a gel, or a regular, compact or concentrated liquid.

79. The cleaning or detergent composition of any of paragraphs 56-78, having an enzyme detergency benefit in cleaning or detergent applications.

80. The cleaning or detergent composition of any of paragraphs 56-79 having improved stability and/or performance, preferably said improved stability and/or performance is under alkaline conditions having pH 7.5 or above.

81. A method for removing a stain from a surface which comprises contacting the surface with a composition according to any of paragraphs 56-80.

82. Use of the cleaning or detergent composition of any of paragraphs 56-80 for degrading a beta-glucan, preferably said beta-glucan is a beta-D-glucan, further preferably said beta-glucan is a beta-1,3-1,4 glucan, most preferably said beta-glucan is a mix-linkage beta-glucan, further most preferably said beta-glucan is a barley beta-glucan or oatmeal beta-glucan (e.g., from cooked oats and/or from cooked and burned-in oats and/or from uncooked oats); optionally said use is carried out under alkaline conditions having pH 7.5 or above.

83. Use of the cleaning or detergent composition of any of paragraphs 56-80 for washing or cleaning a textile and/or a hard surface such as dish wash including Automatic Dish Wash (ADW), preferably said washing or cleaning is washing or cleaning of cooked oats and/or cooked and burned-in oats and/or uncooked oats; optionally said use is carried out under alkaline conditions having pH 7.5 or above.

84. Use of the cleaning or detergent composition of any of paragraphs 56-80 in a cleaning process such as laundry or hard surface cleaning including dish wash including Automatic Dish Wash (ADW) and industrial cleaning; optionally said use is carried out under alkaline conditions having pH 7.5 or above.

85. Use of the cleaning or detergent composition of any of paragraphs 56-80 for laundering and/or hard surface cleaning including dish wash including Automatic Dish Wash (ADW), wherein said composition has an enzyme detergency benefit; optionally said use is carried out under alkaline conditions having pH 7.5 or above.

86. Use of the cleaning or detergent composition of any of paragraphs 56-80 for at least one of the following: preventing, reducing or removing a biofilm from an item, preferably a malodor is reduced or removed from said item; optionally said use is carried out under alkaline conditions having pH 7.5 or above.

87. A process of degrading a beta-glucan comprising applying the cleaning or detergent composition of any of paragraphs 56-80 to said beta-glucan, preferably said beta-glucan is a beta-D-glucan, further preferably said beta-glucan is a beta-1,3-1,4 glucan, most preferably said beta-glucan is a mix-linkage beta-glucan, further most preferably said beta-glucan is a barley beta-glucan or oatmeal beta-glucan (e.g., from cooked oats and/or from cooked and burned-in oats and/or from uncooked oats); optionally, said process is carried out under alkaline conditions having pH 7.5 or above.

88. The process of paragraph 87, wherein said beta-glucan is on the surface of a textile or hard surface, such as dish wash.

89. A method for reducing or preventing soil redeposition using one or more polypeptides or detergent composition of any of preceding paragraphs, preferably said detergent composition is not a dish wash composition.

90. The method of paragraph 89, wherein the detergent composition also comprises one or more further enzymes.

91. The method of any of paragraphs 89-90, wherein the further enzymes are selected from the group comprising proteases, amylases, lipases, cutinases, cellulases, endoglucanases, xyloglucanases, pectinases, pectin lyases, xanthanases, peroxidaes, haloperoxygenases, catalases and mannanases, or any mixture thereof.

92. The method of any of paragraphs 89-91, wherein the detergent composition also comprises one or more detergent components.

93. The method of any of paragraphs 89-92, wherein the detergent components are selected from the group comprising surfactants, builders, hydrotopes, bleaching systems, polymers, fabric hueing agents, adjunct materials, dispersants, dye transfer inhibiting agents, fluorescent whitening agents and soil release polymers, or any mixture thereof.

94. The method of any of paragraphs 89-93, wherein the detergent composition is in the form of a bar, a homogenous tablet, a tablet having two or more layers, a pouch having one or more compartments, a regular or compact powder, a granulate, a paste, a gel, or a regular, compact or concentrated liquid.

95. The method of any of paragraphs 89-94, for dish wash or laundering.

96. Use of one or more polypeptides or cleaning or detergent composition of any of preceding paragraphs for one or more of the following:
  a) reducing or preventing soil redeposition, preferably said use is in a cleaning process or during a cleaning process, further preferably said cleaning or detergent composition is not a dish wash composition, further preferably said cleaning process is not a dish washing process;
  b) removal of cereal containing soil, especially dried-on cereal containing soil, preferably oat flakes containing soil, especially dried-on oat flakes containing soil and/or cooked oats containing soil, and/or cooked and burned-in oats containing soil, and/or uncooked oats containing soil, further preferably said use is in a cleaning process or during a cleaning process, further most preferably said cleaning process is not a dish washing process;
  c) facilitating removal of starch-containing soil in the presence of one or more amylases (e.g., according to any of the preceding paragraphs) and/or for enhancing amylase related cleaning performance, preferably said use is in a cleaning process or during a cleaning process, further preferably said cleaning process is not a dish washing process
  d) facilitating removal of protein-containing soil in the presence of one or more proteases (e.g., according to any of the preceding paragraphs) and/or for enhancing protease related cleaning performance, preferably said use is in a cleaning process or during a cleaning process, further preferably said cleaning process is not a dish washing process.

97. The cleaning or detergent composition of any of preceding paragraphs, wherein said composition has pH of 6.5 or above, preferably of 7.0 or above, more preferably of 7.5 or above and optionally comprises a bleaching agent; preferably said pH is in the range from about 7.5 to about 13.5, further preferably said pH is in the range from about 7.5 to about 12.5, most preferably said pH is in the range from about 8.5 to about 11.5, further most preferably said pH is in the range from about 9.5 to about 10.5; preferably said cleaning or detergent composition is not a dish washing composition.

98. The cleaning or detergent composition of any of preceding paragraphs, further comprising a copolymer that contains at least one sulfonic acid containing monomer, preferably in an amount from 0.1 to 20% by weight, in particular 0.5 to 18% by weight, particularly preferably 1.0 to 15% by weight, in particular 4 to 14% by weight, particularly 6 to 12% by weight, preferably said cleaning or detergent composition is not a dish washing composition.

99. The cleaning or detergent composition of any of preceding paragraphs, wherein said composition comprises said polypeptide in concentrations of 0.00001 mg enzyme protein/g composition to 100 mg enzyme protein/g composition, preferred 0.0001 mg enzyme protein/g composition to 50 mg enzyme protein/g composition, more preferred 0.001 mg enzyme protein/g composition to 20 mg enzyme protein/g composition, especially preferred 0.01 mg enzyme protein/g composition to 10 mg enzyme protein/g composition; preferably said cleaning or detergent composition is not a dish washing composition.

The present invention is further described by the following examples that should not be construed as limiting the scope of the invention.

Examples

Detergent compositions used in the example sections as described herein included the following:

TABLE A

Model detergent A:

| Compound | Content of compound (% w/w) | Active component (% w/w) |
|---|---|---|
| LAS | 12.0 | 97 |
| AEOS, SLES | 17.6 | 28 |
| Soy fatty acid | 2.8 | 90 |
| Coco fatty acid | 2.8 | 99 |
| AEO | 11.0 | 100 |
| Sodium hydroxide | 1.8 | 99 |
| Ethanol/Propan-2-ol | 3.0 | 90/10 |
| MPG | 6.0 | 98 |
| Glycerol | 1.7 | 99.5 |
| TEA | 3.3 | 100 |
| Sodium formate | 1.0 | 95 |
| Sodium citrate | 2.0 | 100 |
| DTMPA (as Na7-salt) | 0.5 | 42 |
| PCA (as Na-salt) | 0.5 | 40 |
| Phenoxy ethanol | 0.5 | 99 |
| Ion exchanged water | 33.6 | — |

Water hardness was adjusted to 15° dH by addition of $CaCl_2$, $MgCl_2$, and $NaHCO_3$ ($Ca^{2+}:Mg^{2+}:HCO_{3-}$ = 4:1:7.5) to the test system.

TABLE B

Model detergent X:

| Compound | Content of compound (% w/w) | Active component (% w/w) |
|---|---|---|
| LAS | 16.5 | 91 |
| AEO* | 2 | 99.5 |
| Sodium carbonate | 20 | 100 |
| Sodium (di)silicate | 12 | 82.5 |

TABLE B-continued

Model detergent X:

| Compound | Content of compound (% w/w) | Active component (% w/w) |
|---|---|---|
| Zeolite A | 15 | 80 |
| Sodium sulfate | 33.5 | 100 |
| PCA | 1 | 100 |

*Model detergent X was mixed without AEO. AEO was added separately before wash.
Water hardness was adjusted to 12° dH by addition of $CaCl_2$, $MgCl_2$, and $NaHCO_3$ ($Ca^{2+}:Mg^{2+}:HCO_{3-}$ = 2:1:4.5) to the test system.

TABLE C

Model detergent Z without bleach:

| Compound | Content of compound (% w/w) | % active component (% w/w) |
|---|---|---|
| LAS | 7.0 | 85.3 |
| Soap | 1.1 | 93 |
| AEO* | 1.5 | 99.5 |
| Soda ash | 20.1 | 99.5 |
| Hydrous sodium silicate | 10.0 | 80.1 |
| Zeolite A | 5.0 | 80 |
| Sodium citrate | 2.0 | 100 |
| HEDP-Na4 | 0.2 | 84 |
| Polyaerylate | 1.1 | 92 |
| Sodium sulfate | 52.0 | 100 |

*Model detergent Z without bleach was mixed without AEO. AEO was added separately before wash.
Water hardness was adjusted to 15° dH by addition of $CaCl_2$, $MgCl_2$, and $NaHCO_3$ ($Ca^{2+}:Mg^{2+}:HCO_{3-}$ = 4:1:7.5) to the test system. pH was used as is (10.6) or adjusted to 11.3 with 4M NaOH.

TABLE D

Model detergent Z with bleach:

| Compound | Content of compound (%w/w) | % active component (% w/w) |
|---|---|---|
| LAS | 7.0 | 85.3 |
| Soap | 1.1 | 93 |
| AEO* | 1.5 | 99.5 |
| Soda ash | 20.1 | 99.5 |
| Hydrous sodium silicate | 10.0 | 80.1 |
| Zeolite A | 5.0 | 80 |
| Sodium citrate | 2.0 | 100 |
| HEDP-Na4 | 0.2 | 84 |
| Polyaerylate | 1.1 | 92 |
| Sodium percarbonate | 9.3 | 86 |
| TEAD | 1.1 | 91.8 |
| Sodium sulfate | 41.6 | 100 |

*Model detergent Z with bleach was mixed without AEO. AEO was added separately before wash.
Water hardness was adjusted to 15° dH by addition of $CaCl_2$, $MgCl_2$, and $NaHCO_3$ ($Ca^{2+}:Mg^{2+}:HCO_{3-}$ = 4:1:7.5) to the test system. pH was either as is (10.5) or adjusted to 11.1 with 4M NaOH.

TABLE E

ADW model detergent A:

| Compound | Content of compound (% w/w) | Active component (% w/w) |
|---|---|---|
| MGDA (Trilon M Granules SG) | 20 | 59 |
| Sodium citrate | 20 | 100 |
| Sodium carbonate | 20 | 100 |
| Sodium percarbonate | 10 | 88 |
| Sodium Silicate | 5 | 80 |

TABLE E-continued

ADW model detergent A:

| Compound | Content of compound (% w/w) | Active component (% w/w) |
|---|---|---|
| Sodium sulfate | 12 | 100 |
| Acusol 588G | 5 | 92 |
| TAED | 3 | 92 |
| Surfac 23-6.5 (liq) | 5 | 100 |

Water hardness was adjusted to 21° dH by addition of CaCl$_2$, MgCl$_2$, and NaHCO$_3$ (Ca$^{2+}$:Mg$^{2+}$:HCO$_3{-}$ = 4:1:10) to the test system.

Example 1: Determination of Beta-Glucanase (Uchenase) Activity

An AZCL-Barley beta-glucan (azunne dye covalently cross-linked beta-glucan) assay was used for detection of endo-glucancase activity (Lichenase activity).

AZCL-Barley beta-glucan (75 mg) was suspended in 15 mL detergent (Model detergents A, X, Z with and without bleach and pH adjusted, ADW Model A). To 1 mL of this solution in Eppendorf tubes was added 10 µL enzyme (0.33 mg enzyme protein/Liter), incubated for 15 min at 40° C. while shaking at 1250 rpm in a pre-heated thermo mixer and spun down for 2 min at 13200 rpm, diluted 5 times with a 5% Triton-X-100 including 10 µM CaCl$_2$ and 250 µL of the solution was transferred to a micro-titer plate and the sample absorbance was measured at 590 nm.

Example 2: Cloning, Expression and Purification of GH16 Endo-β-1,3-1,4-Glucanase from the Genus *Bacillus*

The beta-glucanases were derived from bacterial strains obtain either from the German collection of Microorganisms and Cell Cultures (DSMZ) or by isolation from environmental samples by classical microbiological techniques according to Table 1.

TABLE 1

| Source and Source country of GH16 endo-β-1,3-1,4-glucanase from the genus *Bacillus*: | | |
|---|---|---|
| Strain name | Source | Source Country |
| *Bacillus* sp-62449 | Environmental sample | United States |
| *Bacillus akibai* | Soil | Greece |
| *Bacillus agaradhaerens* | Soil | United States |
| *Bacillus mojavensis* | DSMZ (DSM9205) | United States |

Chromosomal DNA from pure cultures of the individual strains was purified and subjected to full genome sequencing using Illumina technology. The assembled genome sequence and subsequent analysis of the 16S ribosomal subunit gene sequences confirmed the identity of the strains.

The individual genes encoding β-1,3-1,4-glucanases were amplified by PCR and fused with regulatory elements and homology regions for recombination into the *B. subtilis* genome.

The linear integration construct was a SOE-PCR fusion product (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68) made by fusion of the gene between two *Bacillus subtilis* chromosomal regions along with strong promoters and a chloramphenicol resistance marker. The SOE PCR method is also described in patent application WO 2003095658.

The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

The gene was expressed with a *Bacillus clausii* secretion signal (encoding the following amino acid sequence: MKKPLGKIVASTALLISVAFSSSIASA (SEQ ID NO: 10) replacing the native secretion signal. Furthermore the expression construct results in the addition of a N-terminal poly histidine affinity purification tag consisting of the sequence HHHHHHPR (SEQ ID NO: 11) to the expressed mature protein.

The SOE-PCR product was transformed into *Bacillus subtilis* and integrated in the chromosome by homologous recombination into the pectate lyase locus. Subsequently, a recombinant *Bacillus subtilis* clone containing the integrated expression construct was grown in rich liquid culture. The culture broth was centrifuged (20000×g, 20 min) and the supernatant was carefully decanted from the precipitate and used for purification of the enzyme.

Purification of Recombinant Enzymes by Nickel Affinity Chromatography

The pH of the cleared supernatant was adjusted to pH 8, filtrated through a 0.2 µM filter, and the supernatant applied to a 5 ml HisTrap™ excel column. Prior to loading, the column had been equilibrated in 5 column volumes (CV) of 50 mM Tris/HCl pH 8. In order to remove unbound material, the column was washed with 8 CV of 50 mM Tris/HCl pH 8, and elution of the target was obtained with 50 mM HEPES pH 7+10 mM imidazole. The eluted protein was desalted on a HiPrep™ 26/10 desalting column, equilibrated using 3 CV of 50 mM HEPES pH 7+100 mM NaCl. This buffer was also used for elution of the target, and the flow rate was 10 ml/min. Relevant fractions were selected and pooled based on the chromatogram and SDS-PAGE analysis.

Example 3: AZCL-Assay with Beta-Glucanase Enzymes

In this example enzymatic activity were measured on AZCL-Barely beta-glucan substrate under various pH's, temperature and detergent thus modeling various laundry conditions. Measurements of enzymatic activity were carried out as described in example 1, but without the 5 times dilution with 5% Triton-X-100 including 10 µM CaCl$_2$. Comparisons were made with beta-glucanase from *Bacillus amyloliquefaciens* and beta-glucanase from *Bacillus subtilis* in Model detergent A, Model detergent X, Model detergent Z with bleach, Model detergent Z without bleach, Model detergent Z with bleach pH-adjusted and Model Z without bleach pH-adjusted detergent compositions.

TABLE 2

Beta-glucanase activity measured under various pH's, temperatures and laundry detergents using the AZCL-Barley beta-glucan assay (Absorbance):

| Enzyme | pH 7.7 Model A | | pH 10.1 Model X | | pH 10.5 Model Z with bleach | | pH 10.6 Model Z without bleach | | pH 11.1 Model Z with bleach pH-adjusted | | pH 11.3 Model Z without bleach pH-adjusted | |
|---|---|---|---|---|---|---|---|---|---|---|---|---|
| | 40° C. | 60° C. | 40° C. | 60° C. | 40° C. | 60° C. | 40° C. | 60° C. | 40° C. | 60° C. | 40° C. | 60° C. |
| *B. amyloliquefaciens* beta-glucanase (lichenase) | 2.44 | 0.71 | 2.83 | 0.83 | 0.05 | 0.04 | 0.10 | 0.01 | 0.01 | 0.03 | 0.07 | 0.01 |
| *B. subtilis* beta-glucanase (lichenase) | 2.45 | 0.62 | 3.41 | 0.30 | 0.05 | 0.01 | 0.08 | 0.01 | 0.00 | 0.04 | 0.07 | 0.02 |
| *B. akibai* Beta-glucanase (lichenase) | 0.18 | 0.10 | 3.41 | 1.55 | 0.03 | 0.37 | 0.05 | 0.27 | 0.03 | 0.15 | 0.04 | 0.05 |
| *B. agaradhaerens* beta-glucanase (lichenase) | 0.36 | 0.70 | 3.41 | 2.50 | 0.58 | 0.16 | 0.47 | 0.04 | 0.17 | 0.03 | 0.01 | 0.02 |
| *B.* sp-62449 beta-glucanase (lichenase) | 1.22 | 1.15 | 3.25 | 0.08 | 0.22 | 0.10 | 0.30 | 0.01 | 0.05 | 0.04 | 0.04 | 0.01 |
| *B. mojavensis* beta-glucanase (lichenase) | 1.65 | 0.20 | 3.41 | 2.36 | 0.17 | 0.11 | 0.18 | 0.01 | 0.03 | 0.03 | 0.01 | 0.02 |

For details of the model detergent compositions see Tables A-D above.

Example 4: AZCL-Assay of Enzyme Activity on AZCL-Beta-Barley Substrate in Automated Dish Wash Model Detergent Measurements of enzymatic activity were carried out as described in example 1. In this example enzymatic activities of novel beta-glucanases were compared to enzymatic activities of beta-glucanases from *Bacillus amyloliquefaciens* and *Bacillus subtilis* in the automated dish wash detergent ADW model A. The obtained data are shown in Table 3 below:

TABLE 3

Beta-glucanase activity measured under various temperatures in ADW Model A detergent using the AZCL-Barley beta-glucan assay (Absorbance), pH of the ADW model detergent A was 10.2:

| Enzyme | ADW model detergent A | |
|---|---|---|
| | 40° C. | 60° C. |
| Blank | 0.07 | 0.11 |
| *Bacillus amyloliquefaciens* beta-glucanase (lichenase) | 0.46 | 0.34 |
| *Bacillus subtilis* beta-glucanase (lichenase) | 0.42 | 0.21 |
| *Bacillus akibai* beta-glucanase (lichenase) | 0.15 | 2.07 |
| *Bacillus agaradhaerens* beta-glucanase (lichenase) | 0.85 | 1.77 |
| *Bacillus mojavensis* beta-glucanase (lichenase) | 0.85 | 1.06 |
| *Bacillus* sp-62449 beta-glucanase (lichenase) | 1.60 | 0.49 |

Example 5: Beta-Glucanase Stability Measured by TSA

In this example stability of novel beta-glucanases were compared to stabilities of beta-glucanases from *Bacillus amyloliquefaciens* and *Bacillus subtilis*. Thermal shift assays (TSA) were performed with enzyme samples diluted to 0.3 mg/ml in assay buffers: 0.1 M succinic acid, 0.1 M HEPES, 0.1 M CHES, 0.1 M CAPS, 0.15 M KCl, 1 mM CaCl2, 0.01% Triton X100, pH adjusted to 5, 7.5 and 10 respectively. SYPRO Orange dye (Life Technologies S6650) diluted 101× in mQ water. 10 µl diluted enzyme sample+10 µl assay buffer+10 µl dye were mixed in wells of TSA assay plates (LightCycler 480 Multiwell plate 96, white (Roche) and covered with optic seal (LightCycler 480 Sealing foil, Roche). Protein melting analysis was conducted at 25-99° C. at 200° C./h in a Roche Lightcycler 480 II machine running Roche LightCycler 480 software (release 1.5.0 SP4). All samples were analyzed in duplicate. The reported readout is Tm, defined as the midpoint value of the protein melting curves. The obtained data are shown in Table 4 below:

TABLE 4

Stability measured by TSA:

| Enzyme | Buffer pH | TSA |
|---|---|---|
| *Bacillus akibai* beta-glucanase (lichenase) | 5 | 70.9 |
| | 7.5 | 71.8 |
| | 10 | 71.6 |
| *Bacillus agaradhaerens* beta-glucanase (lichenase) | 5 | 58.2 |
| | 7.5 | 64.0 |
| | 10 | 58.6 |

TABLE 4-continued

Stability measured by TSA:

| Enzyme | Buffer pH | TSA |
|---|---|---|
| Bacillus mojavensis beta-glucanase (lichenase) | 5 | 72.8 |
| | 7.5 | 71.2 |
| | 10 | 72.2 |
| Bacillus sp-62449 beta-glucanase (lichenase) | 5 | 43.2 |
| | 7.5 | 53.9 |
| | 10 | 49.4 |
| Bacillus amyloliquefaciens beta-glucanase (lichenase) | 5 | 72.8 |
| | 7.5 | 70.1 |
| | 10 | 73.2 |
| Bacillus subtilis beta-glucanase (lichenase) | 5 | 64.2 |
| | 7.5 | 64.7 |
| | 10 | 64.8 |

Example 6: Beta-Glucanase Substrate Specificity

The substrate specificities of beta-glucanases were further tested using various AZCL-assays from Megazymes (AZCL-Barely beta-glucan, AZCL-HE-cellulose, AZCL-pachyman and AZCL-curdlan (azurine dye covalently cross-linked beta-glucan). The AZCL-substrate (75 mg) was suspended in 15 mL model detergent X. To 1 mL of this solution in Eppendorf tubes was added 10 μL enzyme (0.33 mg enzyme protein/Liter), incubated for 15 min at 40° C. while shaking at 1250 rpm in a pre-heated thermo mixer and spun down for 2 min at 13200 rpm, diluted 5 times with a 5% Triton-X-100 including 10 μM $CaCl_2$ and 250 μL of the solution was transferred to a micro-titer plate and the sample absorbance was measured at 590 nm.

In this example substrate specificity of all 6 beta-glucanases (i.e. from Bacillus akibai, Bacillus agaradhaerens, Bacillus mojavensis, Bacillus sp-62449, Bacillus amyloliquefaciens and Bacillus subtilis) were tested on AZCL-Barley beta-glucan, AZCL-HE-Cellulose AZCL-pachyman and AZCL-curdlan substrates. The obtained results have further confirmed that all 6 tested beta-glucanases have activity on AZCL-Barley beta-glucan substrate only (i.e. positive reaction on AZCL-Barley beta-glucan as a substrate and negative reactions on AZCL-HE-Cellulose AZCL-pachyman and AZCL-curdlan as substrates, Table 5 below). The data shows that tested beta-glucanases only showed activity on beta-glucans containing both beta-1,3 and beta-1,4 linkages and not beta-glucans consisting of pure beta-1,4-glucans or beta-1,3 glucans only or a mixture of beta-1,3- and beta-1,6 linkages. Based on the above results, beta-glucanases of the present invention can be further distinguished from endo-cellulases within beta-glucanase definition as used herein, said endo-cellulases having activity on β-1,4 linkages between D-glucose units of cellulose. Based on the above it is concluded that beta-glucanases of the present invention have licheninase (EC 3.2.1.73) enzymatic activity.

TABLE 5

Substrate specificity of 6 beta-glucanases measured by AZCL-substrates:

| Substrate | Reaction | Substrate for the assay of: | Polymer description |
|---|---|---|---|
| AZCL-Barley beta-glucan | Yes | Lichenase, endo-glucanase and cellulase | β-1,4; β-1,3 linkages between D-glucose units |

TABLE 5-continued

Substrate specificity of 6 beta-glucanases measured by AZCL-substrates:

| Substrate | Reaction | Substrate for the assay of: | Polymer description |
|---|---|---|---|
| AZCL-HE-cellulose | No | Endo-cellulase | β-1,4 linkages between D-glucose units |
| AZCL-curdlan | No | Endo-1,3-beta-D-glucanase | β-1,3 linkages between D-glucose |
| AZCL-pachyman | No | Endo-1,3-beta-D-glucanase | β-1,3 linkages between D-glucose units (branched with β-1,6 glucose units average on every 4) |

Example 7: Synergistic Effect of Beta-Glucanases (Lichenases) of the Invention when Combined with an Alpha-Amylase I. Wascator Bottle Wash Method Description:

A Wascator bottle wash method was used to detect the performance of the enzymes. In a Wascator washing machine (FOM 71 Lab) bottles (60 mL, DSE PP 70×35 Aseptisk, material No.: 216-2620, from VWR) with 25 mL detergent solution including enzyme(s) and four stains (035KC Chocolate porridge oat from Equest, 2 cm in diameter) were added. Two kg ballast (tea towels, cotton) was included in the washing machine. Washed in 25 L water for 30 min at 40° C. in liquid and powder model detergents for laundry (model detergent A1 and model detergent X1, respectively) and in ADW model detergent (ADW model detergent A1). After wash the stains were rinsed with tap water twice (3 L) and dried ON at rt (room temperature) in drying cabinet (Electrolux, Intuition, EDD2400). The remission was measured on a spectrophotometer (Macbeth Color-Eye 7000 Remissions) at 460 nm.

II. Results:

In this example the results of combining the individual lichenases with an alpha-amylase (Stainzyme) (SEQ ID NO: 12) were studied in order to investigate a potential synergistic effect between the two enzymes in various detergents with various pHs using the Wascator bottle wash method. Comparisons were made with lichenase from Bacillus amyloliquefaciens and lichenase from Bacillus subtilis in Model detergent A1, Model detergent X1 and ADW model detergent A1 using 0.01 mg enzyme protein per liter of lichenase and 0.05 mg enzyme protein per liter of Stainzyme at 40° C. The detailed conditions used in this example are described in Tables F-K and the results are shown in Tables 6-8 below.

TABLE F

Experimental condition:

| | |
|---|---|
| Detergent | Model detergent A1 (see Table G below) |
| Detergent dosage | 3.33 g/L |
| Test solution volume | 25 mL |
| pH | As is |
| Wash time | 30 minutes |
| Temperature | 40° C. |
| Water hardness | 15° dH |
| Amylase concentration in test | 0.05 mg/L |
| Beta-glucanase (Lichenase) concentration in test | 0.01 mg/L |
| Test material | O35 KC Chocolate porridge oats |

TABLE G

Model detergent A1:

| Compound | Content of compound (% w/w) | Active component (% w/w) |
|---|---|---|
| LAS | 12.0 | 97 |
| AEOS, SLES | 17.6 | 28 |
| Soy fatty acid | 2.8 | 90 |
| Coco fatty acid | 2.8 | 99 |
| AEO | 11.0 | 100 |
| Sodium hydroxide | 1.8 | 99 |
| Ethanol/Propan-2-ol | 3.0 | 90/10 |
| MPG | 6.0 | 98 |
| Glycerol | 1.7 | 99.5 |
| TEA | 3.3 | 100 |
| Sodium formate | 1.0 | 95 |
| Sodium citrate | 2.0 | 100 |
| DTMPA (as $Na_7$-salt) | 0.5 | 42 |
| PCA (as Na-salt) | 0.5 | 40 |
| Phenoxy ethanol | 0.5 | 99 |
| Ion exchanged water | 33.6 | — |

Water hardness was adjusted to 15° dH by addition of CaCl2, MgCl2, and NaHCO3 (Ca2+:Mg2+:HCO3− = 4:1:7.5) to the test system.

TABLE H

| Experimental condition: | |
|---|---|
| Detergent | Model detergent X1 (see Table I below) |
| Detergent dosage | 1.75 g/L |
| Test solution volume | 25 mL |
| pH | As is |
| Wash time | 30 minutes |
| Temperature | 40° C. |
| Water hardness | 12° dH |
| Amylase concentration in test | 0.05 mg/L |
| Beta-glucanase (Lichenase) concentration in test | 0.01 mg/L |
| Test material | O35 KC Chocolate porridge oats |

TABLE I

Model detergent X1:

| Compound | Content of compound (% w/w) | Active component (% w/w) |
|---|---|---|
| LAS | 16.5 | 91 |
| AEO* | 2 | 99.5 |
| Sodium carbonate | 20 | 100 |
| Sodium (di)silicate | 12 | 82.5 |
| Zeolite A | 15 | 80 |
| Sodium sulfate | 33.5 | 100 |
| PCA | 1 | 100 |

*Model detergent X1 is mixed without AEO. AEO is added separately before wash.
Water hardness was adjusted to 12° dH by addition of CaCl2, MgCl2, and NaHCO3 (Ca2+:Mg2+:HCO3− = 2:1:4.5) to the test system.

TABLE J

| Experimental condition: | |
|---|---|
| Detergent | ADW model detergent A1 (see Table K below) |
| Detergent dosage | 3.77 g/L |
| Test solution volume | 25 mL |
| pH | As is |
| Wash time | 30 minutes |
| Temperature | 40° C. |
| Water hardness | 15° dH |
| Amylase concentration in test | 0.05 mg/L |
| Beta-glucanase (Lichenase) concentration in test | 0.01 mg/L |
| Test material | O35 KC Chocolate porridge oats |

TABLE K

ADW model detergent A1:

| Compound | Content of compound (% w/w) | Active component (% w/w) |
|---|---|---|
| MGDA (Trilon M Granules SG) | 20 | 59 |
| Sodium citrate | 20 | 100 |
| Sodium carbonate | 20 | 100 |
| Sodium percarbonate | 10 | 88 |
| Sodium Silicate | 5 | 80 |
| Sodium sulfate | 12 | 100 |
| Acusol 588G | 5 | 92 |
| TAED | 3 | 92 |
| Surfac 23-6.5 (liq) | 5 | 100 |

Water hardness was adjusted to 21° dH by addition of CaCl2, MgCl2, and NaHCO3 (Ca2+:Mg2+:HCO3− = 4:1:10) to the test system.

ABBREVIATIONS AS USED HEREIN

REM=Measured value

ΔREM=REM—Blank

REM combined=Measured value

ΔREM combined=REM combined—Blank

ΔREM theoretic=ΔREM (Amylase)+ΔREM (Lichenase)

REM Synergistic effect=ΔREM combined—ΔREM theoretic

TABLE 6

Wascator bottle wash in Model detergent A1 at 40° C., 30 min (pH 7.7):

| | Enzymes solo | | Beta-glucanase (Lichenase) in combination with the amylase (Stainzyme) | | | |
|---|---|---|---|---|---|---|
| | REM | ΔREM | REM combined | ΔREM combined | ΔREM theoretic | REM Synergistic effect |
| B. agaradhaerens beta-glucanase (lichenase) | 66.0 | 0.4 | 80.1 | 14.5 | 6.7 | 7.8 |
| B. akibai beta-glucanase (lichenase) | 65.3 | −0.2 | 79.1 | 13.6 | 6.1 | 7.5 |
| B. mojavensis beta-glucanase (lichenase) | 65.8 | 0.2 | 79.3 | 13.7 | 6.5 | 7.2 |
| B. SP-62449 beta-glucanase (lichenase) | 64.9 | −0.7 | 80.0 | 14.4 | 5.6 | 8.8 |

TABLE 6-continued

Wascator bottle wash in Model detergent A1 at 40° C., 30 min (pH 7.7):

|  | Enzymes solo | | REM combined | ΔREM combined | ΔREM theoretic | REM Synergistic effect |
|---|---|---|---|---|---|---|
|  | REM | ΔREM | | | | |
| B. amyloliquefaciens beta-glucanase (lichenase) | 67.3 | 1.8 | 79.5 | 13.9 | 8.1 | 5.9 |
| B. subtilis beta-glucanase (lichenase) | 67.3 | 1.7 | 80.1 | 14.5 | 8.0 | 6.5 |
| Stainzyme | 71.8 | 6.3 | — | — | — | — |
| Blank | 65.5 | 0.0 | — | — | — | — |

TABLE 7

Wascator bottle wash in Model detergent X1 at 40° C., 30 min (pH 10.1):

Beta-glucanase (Lichenase) in combination with the amylase Stainzyme

|  | Enzymes solo | | REM combined | ΔREM combined | ΔREM theoretic | REM Synergistic effect |
|---|---|---|---|---|---|---|
|  | REM | ΔREM | | | | |
| B. agaradhaerens beta-glucanase (lichenase) | 61.4 | −0.4 | 74.5 | 12.7 | 4.4 | 8.2 |
| B. akibai beta-glucanase (lichenase) | 62.2 | 0.3 | 74.9 | 13.1 | 5.2 | 7.9 |
| B. mojavensis beta-glucanase (lichenase) | 61.8 | −0.1 | 74.3 | 12.4 | 4.8 | 7.6 |
| B. SP-62449 beta-glucanase (lichenase) | 61.9 | 0.1 | 73.0 | 11.1 | 5.0 | 6.1 |
| B. amyloliquefaciens beta-glucanase (lichenase) | 59.9 | −1.9 | 72.0 | 10.2 | 2.9 | 7.3 |
| B. subtilis beta-glucanase (lichenase) | 60.8 | −1.0 | 71.8 | 10.0 | 3.8 | 6.1 |
| Stainzyme | 66.7 | 4.9 | — | — | — | — |
| Blank | 61.8 | 0.0 | — | — | — | — |

TABLE 8

Wascator bottle wash in ADW Model detergent A1 at 40° C., 30 min (pH 10.2):

Beta-glucanase (Lichenase) in combination with the amylase Stainzyme

|  | Enzymes solo | | REM combined | ΔREM combined | ΔREM theoretic | REM Synergistic effect |
|---|---|---|---|---|---|---|
|  | REM | ΔREM | | | | |
| B. agaradhaerens beta-glucanase (lichenase) | 60.5 | −2.1 | 75.1 | 12.5 | 6.1 | 6.4 |
| B. akibai beta-glucanase (lichenase) | 60.7 | −1.9 | 73.9 | 11.3 | 6.3 | 5.0 |
| B. mojavensis beta-glucanase (lichenase) | 63.0 | 0.3 | 73.3 | 10.7 | 8.5 | 2.1 |
| B. SP-62449 beta-glucanase (lichenase) | 60.8 | −1.8 | 74.5 | 11.9 | 6.4 | 5.5 |
| B. amyloliquefaciens beta-glucanase (lichenase) | 61.6 | −1.0 | 71.3 | 8.6 | 7.2 | 1.4 |
| B. subtilis beta-glucanase (lichenase) | 58.1 | −4.5 | 72.5 | 9.9 | 3.7 | 6.2 |
| Stainzyme | 70.8 | 8.2 | — | — | — | — |
| Blank | 62.6 | 0.0 | — | — | — | — |

Example 8: Determination of the pH Optimum

Subsequently, the pH optimum of all 6 beta-glucanases was determined on 0.4% w/v AZCL-glucan (barley) substrate in Britton Robinson buffer (100 mM phosphoric acid, 100 mM acetic acid, 100 mM boric acid, 0.01% Trinton X-100, 100 mM KCl, 2 mM CaCl2) adjusted to pH 2-12 with NaOH. An enzyme dilution expected to be in the high end of the linear assay range was selected for all pH values under investigation. The pH optimum was investigated in the pH 2-10 range, and for a few samples both lower and higher pH values were included to positively identify the optimum. The results are shown in this Table 9.

TABLE 9 pH optimum of beta-glucanases (lichenases):

| Organism | Mw, kDa | pI | A595/ mg | pH optimum | pH 10/ pH opt |
|---|---|---|---|---|---|
| Bacillus amyloliquefaciens | 24 | 5.2 | 765 | 6 | 0.01 |
| Bacillus subtilis | 24 | 6.1 | 242 | 6 | 0.11 |
| Bacillus sp-62449 | 40 | 4.4 | 763 | 8 | 0.73 |
| Bacillus akibai | 29 | 5.2 | 5 | 6-9 | 0.9 |
| Bacillus agaradhaerens | 27 | 4.5 | 106 | 9 | 0.68 |
| Bacillus mojavensis | 25 | 7.4 | 313 | 8 | 0.23 |

Based on the above a number of observations were made:

The beta-glucanase from *Bacillus amyloliquefaciens* and *Bacillus subtilis* was found to have a pH optimum of 6.0, and relative to this activity only between 1-11% percent activity at pH 10.0. The new bacterial beta-glucanases were found to have pH optimum ranging from pH 6-9, but with a significantly higher relative activity at pH 10 ranging from 23-90% compared to the enzymes from *Bacillus subitilis* and *Bacillus amyloliquefaciens*. The GH16 beta-glucanase from *B. akibai* had a very broad pH optimum.

Example 9: Synergistic Effect of Lichenases Combined with Alpha-Amylases

I. Wascator Bottle Wash Method Description:

A Wascator bottle wash method was used to detect the performance of the enzymes. In a Wascator washing machine (FOM 71 Lab) was added bottles (60 mL, DSE PP 70×35 Aseptisk, material #: 216-2620, from VWR) with 25 mL detergent solution including enzyme(s) and four stains (O35KC Chocolate porridge oat from Warwick Equest Ltd, Unit 55, Consett Business Park, Consett,County Durham, DH8 6BN, United Kingdom, 2 cm in diameter). Two kg ballast (tea towels, cotton) was included in the washing machine. Washed in 25 L water for 20 or 30 min at 40° C. in liquid and powder model detergents for laundry (model detergent A and model detergent X, respectively) and in ADW model detergent (ADW model detergent A). After wash the stains were rinsed with tap water twice (3 L) and dried overnight at room temperature in drying cabinet (Electrolux, Intuition, EDD2400). The remission was measured on a spectrophotometer (Macbeth Color-Eye 7000 Remissions) at 460 nm.

II. Results:

In this example the results of combining the individual mature lichenases of *Bacillus agaradhaerens* Lichenase (SEQ ID NO: 39, His-tagged, recombinant), *Bacillus akibai* Lichenase (SEQ ID NO: 38, His-tagged, recombinant), *Bacillus mojavensis* Lichenase (SEQ ID NO: 40, His-tagged, recombinant), *Bacillus sp-62449* Lichenase (SEQ ID NO: 37, His-tagged, recombinant), *Bacillus amyloliquefaciens* Lichenase (SEQ ID NO: 32) and *Bacillus subtillis* Lichenase (SEQ ID NO: 33) with different amylases as outlined below were studied in order to investigate a potential synergy effect between the two enzymes in various detergents with various pHs using the Wascator bottle wash method. Comparisons were made with lichenase from *Bacillus amyloliquefaciens* and lichenase from *Bacillus subtilis* in Model detergent A, Model detergent X and ADW model detergent A using lichenase concentration of 0.01 mg enzyme protein per liter and amylase concentration of 0.05 mg enzyme protein per liter at 40° C. The detailed conditions are described in Tables 10-15 and the results are shown in Tables 16-47 below.

TABLE 10

| Experimental condition | |
|---|---|
| Detergent | Model detergent A (see Table 11) |
| Detergent dosage | 3.33 g/L |
| Test solution volume | 25 mL |
| pH | As is |
| Wash time | 20 or 30 minutes |
| Temperature | 40° C. |
| Water hardness | 15° dH |
| Amylase concentration in test | 0.05 mg/L |
| Lichenase concentration in test | 0.01 mg/L |
| Test material | O35 KC Chocolate porridge oats |

TABLE 11

| Model detergent A | | |
|---|---|---|
| Compound | Content of compound (% w/w) | Active component (% w/w) |
| LAS | 12.0 | 97 |
| AEOS, SLES | 17.6 | 28 |
| Soy fatty acid | 2.8 | 90 |

TABLE 11-continued

| Model detergent A | | |
|---|---|---|
| Compound | Content of compound (% w/w) | Active component (% w/w) |
| Coco fatty acid | 2.8 | 99 |
| AEO | 11.0 | 100 |
| Sodium hydroxide | 1.8 | 99 |
| Ethanol/Propan-2-ol | 3.0 | 90/10 |
| MPG | 6.0 | 98 |
| Glycerol | 1.7 | 99.5 |
| TEA | 3.3 | 100 |
| Sodium formate | 1.0 | 95 |
| Sodium citrate | 2.0 | 100 |
| DTMPA (as $Na_7$-salt) | 0.5 | 42 |
| PCA (as Na-salt) | 0.5 | 40 |
| Phenoxy ethanol | 0.5 | 99 |
| Ion exchanged water | 33.6 | — |

Water hardness was adjusted to 15° dH by addition of CaCl2, MgCl2, and NaHCO3 ($Ca^{2+}:Mg^{2+}:HCO3^-$ = 4:1:7.5) to the test system.

TABLE 12

| Experimental condition | |
|---|---|
| Detergent | Model detergent X (see Table 13) |
| Detergent dosage | 1.75 g/L |
| Test solution volume | 25 mL |
| pH | As is |
| Wash time | 20 or 30 minutes |
| Temperature | 40° C. |
| Water hardness | 12° dH |
| Amylase concentration in test | 0.05 mg/L |
| Lichenase concentration in test | 0.01 mg/L |
| Test material | O35 KC Chocolate porridge oats |

TABLE 13

| Model detergent X | | |
|---|---|---|
| Compound | Content of compound (% w/w) | Active component (% w/w) |
| LAS | 16.5 | 91 |
| AEO* | 2 | 99.5 |
| Sodium carbonate | 20 | 100 |
| Sodium (di)silicate | 12 | 82.5 |
| Zeolite A | 15 | 80 |
| Sodium sulfate | 33.5 | 100 |
| PCA | 1 | 100 |

*Model detergent X is mixed without AEO. AEO is added separately before wash.

Water hardness was adjusted to 12° dH by addition of CaCl2, MgCl2, and NaHCO3 ($Ca^{2+}:Mg^{2+}:HCO3^-$ = 2:1:4.5) to the test system.

TABLE 14

| Experimental condition | |
|---|---|
| Detergent | ADW model detergent A (see Table 15) |
| Detergent dosage | 3.77 g/L |
| Test solution volume | 25 mL |
| pH | As is |
| Wash time | 20 or 30 minutes |
| Temperature | 40° C. |
| Water hardness | 21° dH |
| Amylase concentration in test | 0.05 mg/L |
| Lichenase concentration in test | 0.01 mg/L |
| Test material | O35 KC Chocolate porridge oats |

TABLE 15

ADW model detergent A

| Compound | Content of compound (% w/w) | Active component (% w/w) |
|---|---|---|
| MGDA (Trilon M Granules SG) | 20 | 59 |
| Sodium citrate | 20 | 100 |
| Sodium carbonate | 20 | 100 |
| Sodium percarbonate | 10 | 88 |
| Sodium Silicate | 5 | 80 |
| Sodium sulfate | 12 | 100 |
| Acusol 588G | 5 | 92 |
| TAED | 3 | 92 |
| Surfac 23-6.5 (liq) | 5 | 100 |

Water hardness was adjusted to 21° dH by addition of CaCl2, MgCl2, and NaHCO3 ($Ca^{2+}:Mg^{2+}:HCO3^- = 4:1:10$) to the test system.

ABBREVIATIONS

REM=Measured value
ΔREM=REM—Blank
REM combined=Measured value
ΔREM combined=REM combined—Blank
ΔREM theoretic=ΔREM (Amylase)+ΔREM (Lichenase)
REM Synergy effect=ΔREM combined—ΔREM theoretic

TABLE 16

Wascator bottle wash in Model detergent A at 40° C., 30 min (pH 7.7)

Lichenase in combination with the amylase having SEQ ID NO: 12

| | Enzymes solo | | REM com-bined | ΔREM com-bined | ΔREM theoretic | REM Synergy effect |
|---|---|---|---|---|---|---|
| | REM | ΔREM | | | | |
| Bacillus agaradhaerens lichenase | 65.1 | −0.4 | 80.1 | 14.6 | 5.9 | 8.7 |
| Bacillus Akibai Lichenase | 66.3 | 0.9 | 79.1 | 13.6 | 7.2 | 6.4 |
| Bacillus Mojavensis Lichenase | 65.8 | 0.3 | 79.3 | 13.8 | 6.7 | 7.1 |
| Bacillus SP-62449 Lichenase | 64.9 | −0.6 | 78.7 | 13.2 | 5.8 | 7.5 |
| Bacillus amyloliquefaciens lichenase | 66.1 | 0.7 | 79.5 | 14.0 | 7.0 | 7.0 |
| Bacillus Subtillis Lichenase | 67.3 | 1.8 | 80.1 | 14.6 | 8.2 | 6.4 |
| Amylase having SEQ ID NO: 12 | 71.8 | 6.3 | — | — | — | — |
| Blank | 65.5 | 0.0 | — | — | — | — |

TABLE 17

Wascator bottle wash in Model detergent A at 40° C., 30 min (pH 7.7)

Lichenase in combination with the amylase which is the variant of SEQ ID NO: 23 having alterations G182* + D183*

| | Enzymes solo | | REM com-bined | ΔREM com-bined | ΔREM theo-retic | REM Synergy effect |
|---|---|---|---|---|---|---|
| | REM | ΔREM | | | | |
| Bacillus agaradhaerens lichenase | 63.9 | 0.4 | 76.2 | 12.7 | 6.1 | 6.6 |
| Bacillus Akibai Lichenase | 63.5 | 0.1 | 75.3 | 11.9 | 5.8 | 6.1 |
| Bacillus Mojavensis Lichenase | 65.0 | 1.6 | 74.5 | 11.1 | 7.3 | 3.8 |
| Bacillus SP-62449 Lichenase | 64.6 | 1.1 | 75.0 | 11.6 | 6.9 | 4.7 |
| Bacillus amyloliquefaciens lichenase | 65.7 | 2.3 | 75.6 | 12.2 | 8.0 | 4.2 |
| Amylase, which is the variant of SEQ ID NO: 23 having alterations G182* + D183* | 69.2 | 5.7 | — | — | — | — |
| Blank | 63.4 | 0.0 | — | — | — | — |

TABLE 18

Wascator bottle wash in Model detergent A at 40° C., 30 min (pH 7.7)

| | Enzymes solo | | REM combined | ΔREM combined | ΔREM theoretic | REM Synergy effect |
|---|---|---|---|---|---|---|
| | REM | AREM | | | | |
| *Bacillus agaradhaerens* lichenase | 63.9 | 0.4 | 77.5 | 14.1 | 8.6 | 5.5 |
| *Bacillus Akibai* Lichenase | 63.5 | 0.1 | 78.1 | 14.7 | 8.3 | 6.4 |
| *Bacillus Mojavensis* Lichenase | 65.0 | 1.6 | 77.9 | 14.5 | 9.7 | 4.7 |
| *Bacillus* SP-62449 Lichenase | 64.6 | 1.1 | 77.1 | 13.6 | 9.3 | 4.3 |
| Amylase, which is the variant of SEQ ID NO: 24 having alterations H183* + G184* + I405L + A421H + A422P + A428T | 71.6 | 8.1 | — | — | — | — |
| Blank | 63.4 | 0.0 | — | — | — | — |

Lichenase in combination with the amylase, which is the variant of SEQ ID NO: 24 having alterations H183* + G184* + I405L + A421H + A422P + A428T

TABLE 19

Wascator bottle wash in Model detergent A at 40° C., 30 min (pH 7.7)

Lichenase in combination with the amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 65.1 | −0.4 | 75.9 | 10.4 | 6.4 | 4.0 |
| *Bacillus Akibai* Lichenase | 66.3 | 0.9 | 75.8 | 10.4 | 7.7 | 2.7 |
| *Bacillus Mojavensis* Lichenase | 65.8 | 0.3 | 76.9 | 11.4 | 7.1 | 4.3 |
| *Bacillus* SP-62449 Lichenase | 64.9 | −0.6 | 75.9 | 10.4 | 6.2 | 4.2 |
| *Bacillus amyloliquefaciens* lichenase | 66.1 | 0.7 | 76.7 | 11.2 | 7.5 | 3.7 |
| *Bacillus Subtillis* Lichenase | 67.3 | 1.8 | 76.9 | 11.4 | 8.6 | 2.8 |
| Amylase, which is the variant of SEQ ID NO: 24 having alterations M9L + R118K + G149A + G182T + G186A + D183* + G184* + N195F + M202L + T257I + | 72.3 | 6.8 | — | — | — | — |

TABLE 19-continued

Wascator bottle wash in Model detergent A at 40° C., 30 min (pH 7.7)

| | Enzymes solo | | REM combined | ΔREM combined | ΔREM theoretic | REM Synergy effect |
|---|---|---|---|---|---|---|
| | REM | ΔREM | | | | |
| Y295F + N299Y + R320K + M323T + A339S + E345R + R458K | | | | | | |
| Blank | 65.5 | 0.0 | — | — | — | — |

TABLE 20

Wascator bottle wash in Model detergent A at 40° C., 20 min (pH 7.7)

Lichenase in combination with the amylase which is the variant of SEQ ID NO: 24 having alterations R178* + G179* + E187P + I203Y + R458N + T459S + D460T + G476K

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 64.0 | −0.8 | 77.7 | 13.0 | 10.6 | 2.3 |
| *Bacillus Akibai* Lichenase | 64.7 | −0.1 | 77.6 | 12.8 | 11.3 | 1.5 |
| *Bacillus* SP-62449 Lichenase | 64.0 | −0.8 | 77.4 | 12.6 | 10.6 | 2.0 |
| Amylase which is the variant of SEQ ID NO: 24 having alterations R178* + G179* + E187P + I203Y + R458N + T459S + D460T + G476K | 76.2 | 11.4 | — | — | — | — |
| Blank | 64.8 | 0.0 | — | — | — | — |

TABLE 21

Wascator bottle wash in Model detergent A at 40° C., 30 min (pH 7.7)

Lichenase in combination with the amylase which is the variant of SEQ ID NO: 27 having alteration M202L

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 65.1 | −0.4 | 72.2 | 6.7 | 3.7 | 3.0 |
| *Bacillus Mojavensis* Lichenase | 65.8 | 0.3 | 73.4 | 7.9 | 4.5 | 3.5 |
| *Bacillus* SP-62449 Lichenase | 64.9 | −0.6 | 71.5 | 6.1 | 3.6 | 2.5 |
| *Bacillus amyloliquefaciens* lichenase | 66.1 | 0.7 | 72.1 | 6.6 | 4.8 | 1.8 |
| Amylase which is the variant of SEQ ID NO: 27 having alteration M202L | 69.6 | 4.2 | — | — | — | — |
| Blank | 65.5 | 0.0 | — | — | — | — |

TABLE 22

Wascator bottle wash in Model detergent A at 40° C., 30 min (pH 7.7)

|  | Enzymes solo | | REM combined | ΔREM combined | ΔREM theoretic | REM Synergy effect |
|---|---|---|---|---|---|---|
|  | REM | ΔREM | | | | |
|  | | | Lichenase in combination with the amylase which the variant of SEQ ID NO: 28 having alterations R180* + S181* + S243Q + G475K | | | |
| *Bacillus agaradhaerens* lichenase | 65.1 | −0.4 | 79.2 | 13.7 | 6.0 | 7.7 |
| *Bacillus Akibai* Lichenase | 66.3 | 0.9 | 75.9 | 10.4 | 7.3 | 3.1 |
| *Bacillus Mojavensis* Lichenase | 65.8 | 0.3 | 79.0 | 13.5 | 6.8 | 6.7 |
| *Bacillus SP-62449* Lichenase | 64.9 | −0.6 | 78.9 | 13.5 | 5.8 | 7.6 |
| *Bacillus amyloliquefaciens* lichnase | 66.1 | 0.7 | 77.9 | 12.5 | 7.1 | 5.4 |
| *Bacillus Subtillis* Lichenase | 67.3 | 1.8 | 78.2 | 12.7 | 8.2 | 4.5 |
| Amylase which the variant of SEQ ID NO: 28 having alterations R180* + S181* + S243Q + G475K | 71.9 | 6.4 | — | — | — | — |
| Blank | 65.5 | 0.0 | — | — | — | — |

TABLE 23

Wascator bottle wash in Model detergent A at 40° C., 30 min (pH 7.7)

|  | Enzymes solo | | REM combined | ΔREM combined | ΔREM theoretic | REM Synergy effect |
|---|---|---|---|---|---|---|
|  | REM | ΔREM | | | | |
|  | | | Lichenase in combination with the amylase of SEQ ID NO: 29 having alterations D183* + G184* + W140Y + N195F + I206Y + Y243F + E260G + G304R + G476K | | | |
| *Bacillus agaradhaerens* lichenase | 65.1 | −0.4 | 77.4 | 11.9 | 7.9 | 4.0 |
| *Bacillus Akibai* Lichenase | 66.3 | 0.9 | 77.9 | 12.4 | 9.2 | 3.2 |
| *Bacillus Mojavensis* Lichenase | 65.8 | 0.3 | 79.1 | 13.6 | 8.7 | 5.0 |
| *Bacillus SP-62449* Lichenase | 64.9 | −0.6 | 79.6 | 14.1 | 7.8 | 6.3 |
| *Bacillus amyloliquefaciens* lichenase | 66.1 | 0.7 | 77.7 | 12.3 | 9.0 | 3.3 |
| *Bacillus Subtillis* Lichenase | 67.3 | 1.8 | 77.2 | 11.8 | 10.2 | 1.6 |
| Amylase of SEQ ID NO: 29 having alterations D183* + G184* + W140Y + N195F + I206Y + Y243F + E260G + G304R + G476K | 73.8 | 8.4 | — | — | — | — |
| Blank | 65.5 | 0.0 | — | — | — | — |

TABLE 24

Wascator bottle wash in Model detergent A at 40° C., 30 min (pH 7.7)

|  | Enzymes solo | | REM combined | ΔREM combined | ΔREM theoretic | REM Synergy effect |
|---|---|---|---|---|---|---|
|  | REM | ΔREM | | | | |
|  | | | Lichenase in combination with the amylase, which is the variant of SEQ ID NO: 30 having alterations H1* + N54S + V56T + K72R + G109A + F113Q + R116Q + W167F + Q172G + A174S + G184T + N195F + V206L + K391A + P473R + G476K | | | |
| *Bacillus agaradhaerens* lichenase | 65.1 | −0.4 | 80.6 | 15.1 | 5.9 | 9.2 |
| *Bacillus Akibai* Lichenase | 66.3 | 0.9 | 79.4 | 13.9 | 7.2 | 6.8 |
| *Bacillus Mojavensis* Lichenase | 65.8 | 0.3 | 79.4 | 14.0 | 6.6 | 7.3 |
| *Bacillus SP-62449* Lichenase | 64.9 | −0.6 | 80.2 | 14.7 | 5.7 | 9.0 |
| *Bacillus amyloliquefaciens* lichenase | 66.1 | 0.7 | 79.5 | 14.1 | 7.0 | 7.1 |
| *Bacillus Subtillis* Lichenase | 67.3 | 1.8 | 80.2 | 14.7 | 8.1 | 6.6 |
| Amylase, which is the variant of SEQ ID NO: 30 having alterations | 71.8 | 6.3 | — | — | — | — |

TABLE 24-continued

Wascator bottle wash in Model detergent A at 40° C., 30 min (pH 7.7)

Lichenase in combination with the amylase, which is the variant of SEQ ID NO: 30 having alterations H1* + N54S + V56T + K72R + G109A + F113Q + R116Q + W167F + Q172G + A174S + G184T + N195F + V206L + K391A + P473R + G476K

|  | Enzymes solo | | REM combined | ΔREM combined | ΔREM theoretic | REM Synergy effect |
|---|---|---|---|---|---|---|
|  | REM | ΔREM | | | | |
| H1* + N54S + V56T + K72R + G109A + F113Q + R116Q + W167F + Q172G + A174S + G184T + N195F + V206L + K391A + P473R + G476K | | | | | | |
| Blank | 65.5 | 0.0 | — | — | — | — |

TABLE 25

Wascator bottle wash in Model detergent A at 40° C., 30 min (pH 7.7)

Lichenase in combination with the amylase, which is the variant of SEQ ID NO: 31 having alterations M9L + R118K + G149A + G182T + G186A + D183* + G184* + N195F + T246V + T257I + Y295F + N299Y + R320K + M323T + A339S + E345R + R458K

|  | Enzymes solo | | REM combined | ΔREM combined | ΔREM theoretic | REM Synergy effect |
|---|---|---|---|---|---|---|
|  | REM | ΔREM | | | | |
| *Bacillus agaradhaerens* lichenase | 65.5 | 0.8 | 76.2 | 11.4 | 6.8 | 4.7 |
| *Bacillus Akibai* Lichenase | 66.1 | 1.3 | 76.7 | 12.0 | 7.3 | 4.6 |
| *Bacillus Mojavensis* Lichenase | 65.8 | 1.0 | 77.5 | 12.7 | 7.0 | 5.7 |
| *Bacillus* SP-62449 Lichenase | 64.6 | −0.2 | 76.6 | 11.8 | 5.8 | 6.0 |
| *Bacillus Subtillis* Lichenase | 67.4 | 2.7 | 76.1 | 11.4 | 8.7 | 2.7 |
| Amylase, which is the variant of SEQ ID NO: 31 having alterations M9L + R118K + G149A + G182T + G186A + D183* + G184* + N195F + T246V + T257I + Y295F + N299Y + R320K + M323T + A339S + E345R + R458K | 70.8 | 6.0 | — | — | — | — |
| Blank | 64.8 | 0.0 | — | — | — | — |

TABLE 26

Wascator bottle wash in Model detergent X at 40° C., 30 min (pH 10.1)

Lichenase in combination with the amylase having SEQ ID NO: 12

|  | Enzymes solo | | REM combined | ΔREM combined | ΔREM theoretic | REM Synergy effect |
|---|---|---|---|---|---|---|
|  | REM | ΔREM | | | | |
| *Bacillus agaradhaerens* lichenase | 62.0 | 0.2 | 74.5 | 12.7 | 5.0 | 7.6 |
| *Bacillus Akibai* Lichenase | 62.2 | 0.3 | 74.9 | 13.1 | 5.2 | 7.9 |
| *Bacillus Mojavensis* Lichenase | 61.8 | −0.1 | 74.3 | 12.4 | 4.8 | 7.6 |
| *Bacillus* SP-62449 Lichenase | 61.9 | 0.1 | 73.0 | 11.1 | 5.0 | 6.1 |
| amylase having SEQ ID NO: 12 | 66.7 | 4.9 | — | — | — | — |
| Blank | 61.8 | 0.0 | — | — | — | — |

TABLE 27

Wascator bottle wash in Model detergent X at 40° C., 30 min (pH 10.1)

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 59.4 | −0.1 | 72.8 | 13.3 | 6.4 | 6.8 |
| *Bacillus Akibai* Lichenase | 59.8 | 0.3 | 73.1 | 13.6 | 6.8 | 6.8 |
| *Bacillus Mojavensis* Lichenase | 59.5 | −0.1 | 73.2 | 13.6 | 6.5 | 7.2 |
| *Bacillus* SP-62449 Lichenase | 60.9 | 1.3 | 72.1 | 12.6 | 7.9 | 4.7 |
| *Bacillus amyloliquefaciens* lichenase | 59.9 | 0.4 | 69.6 | 10.0 | 6.9 | 3.1 |
| Amylase which is the variant of SEQ ID NO: 23 having alterations G182* + D183* | 66.1 | 6.5 | — | — | — | — |
| Blank | 59.5 | 0.0 | — | — | — | — |

TABLE 28

Wascator bottle wash in Model detergent X at 40° C., 30 min (pH 10.1)

Lichenase in combination with the amylase, which is the variant of SEQ ID NO: 24 having alterations H183* + G184* + I405L + A421H + A422P + A428T

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 59.4 | −0.1 | 70.4 | 10.9 | 5.0 | 5.8 |
| *Bacillus Akibai* Lichenase | 59.8 | 0.3 | 70.1 | 10.5 | 5.4 | 5.1 |
| *Bacillus Mojavensis* Lichenase | 59.5 | −0.1 | 70.5 | 10.9 | 5.1 | 5.9 |
| *Bacillus* SP-62449 Lichenase | 60.9 | 1.3 | 69.9 | 10.4 | 6.5 | 3.9 |
| *Bacillus amyloliquefaciens* lichenase | 59.9 | 0.4 | 68.4 | 8.9 | 5.5 | 3.4 |
| Amylase, which is the variant of SEQ ID NO: 24 having alterations H183* + G184* + I405L + A421H + A422P + A428T | 64.7 | 5.1 | — | — | — | — |
| Blank | 59.5 | 0.0 | — | — | — | — |

TABLE 29

Wascator bottle wash in Model detergent X at 40° C., 30 min (pH 10.1)

Lichenase in combination with the amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 62.5 | 1.6 | 74.9 | 13.9 | 7.8 | 6.1 |
| *Bacillus Akibai* Lichenase | 61.6 | 0.7 | 73.6 | 12.6 | 6.9 | 5.7 |
| *Bacillus Mojavensis* Lichenase | 61.7 | 0.7 | 71.4 | 10.4 | 6.9 | 3.5 |
| *Bacillus* SP-62449 Lichenase | 59.2 | −1.8 | 73.1 | 12.1 | 4.5 | 7.6 |

TABLE 29-continued

Wascator bottle wash in Model detergent X at 40° C., 30 min (pH 10.1)

Lichenase in combination with the amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K

|  | Enzymes solo | | REM combined | ΔREM combined | ΔREM theoretic | REM Synergy effect |
|---|---|---|---|---|---|---|
|  | REM | ΔREM |  |  |  |  |
| *Bacillus amyloliquefaciens* lichenase | 61.2 | 0.2 | 68.9 | 7.9 | 6.4 | 1.5 |
| *Bacillus Subtillis* Lichenase | 60.8 | −0.2 | 71.5 | 10.5 | 6.1 | 4.4 |
| Amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K | 67.2 | 6.2 | — | — | — | — |
| Blank | 61.0 | 0.0 | — | — | — | — |

TABLE 30

Wascator bottle wash in Model detergent X at 40° C., 30 min (pH 10.1)

Lichenase in combination with the amylase, which is the variant of SEQ ID NO: 24 having alterations R178* + G179* + E187P + I203Y + R458N + T459S + D460T + G476K

|  | Enzymes solo | | REM combined | ΔREM combined | ΔREM theoretic | REM Synergy effect |
|---|---|---|---|---|---|---|
|  | REM | ΔREM |  |  |  |  |
| *Bacillus agaradhaerens* Lichenase | 62.3 | 0.4 | 73.7 | 11.7 | 6.4 | 5.3 |
| *Bacillus Akibai* Lichenase | 61.6 | −0.4 | 72.4 | 10.4 | 5.7 | 4.7 |
| *Bacillus Mojavensis* Lichenase | 61.4 | −0.6 | 73.0 | 11.1 | 5.5 | 5.6 |
| *Bacillus* SP-62449 Lichenase | 61.0 | −1.0 | 72.0 | 10.0 | 5.1 | 4.9 |
| *Bacillus amyloliquefaciens* lichenase | 62.1 | 0.1 | 71.5 | 9.5 | 6.2 | 3.3 |
| *Bacillus Subtillis* Lichenase | 62.2 | 0.2 | 72.8 | 10.8 | 6.3 | 4.6 |
| amylase which is the variant of SEQ ID NO: 24 having alterations R178* + G179* + E187P + I203Y + R458N + T459S + D460T + G476K | 68.0 | 6.1 | — | — | — | — |
| Blank | 62.0 | 0.0 | — | — | — | — |

TABLE 31

Wascator bottle wash in Model detergent X at 40° C., 30 min (pH 10.1)

Lichenase in combination with the amylase, which is the variant of SEQ ID NO: 27 having alteration M202L

|  | Enzymes solo | | REM combined | ΔREM combined | ΔREM theoretic | REM Synergy effect |
|---|---|---|---|---|---|---|
|  | REM | ΔREM |  |  |  |  |
| *Bacillus agaradhaerens* Lichenase | 62.3 | 0.4 | 72.0 | 10.1 | 5.4 | 4.7 |
| *Bacillus Akibai* Lichenase | 61.6 | −0.4 | 71.3 | 9.3 | 4.6 | 4.7 |
| *Bacillus Mojavensis* Lichenase | 61.4 | −0.6 | 71.6 | 9.6 | 4.4 | 5.2 |
| *Bacillus* SP-62449 Lichenase | 61.0 | −1.0 | 70.6 | 8.6 | 4.0 | 4.6 |
| *Bacillus amyloliquefaciens* lichenase | 62.1 | 0.1 | 68.5 | 6.6 | 5.1 | 1.4 |
| *Bacillus Subtillis* Lichenase | 62.2 | 0.2 | 71.2 | 9.2 | 5.2 | 4.0 |
| Amylase which is the variant of SEQ ID NO: 27 having alteration M202L | 67.0 | 5.0 | — | — | — | — |
| Blank | 62.0 | 0.0 | — | — | — | — |

TABLE 32

Wascator bottle wash in Model detergent X at 40° C., 20 min (pH 10.1)

| | Enzymes solo | | REM | ΔREM | ΔREM | REM Synergy |
|---|---|---|---|---|---|---|
| | REM | ΔREM | combined | combined | theoretic | effect |
| *Bacillus Akibai* Lichenase | 61.8 | −0.4 | 63.3 | 1.1 | −0.3 | 1.4 |
| *Bacillus Mojavensis* Lichenase | 60.4 | −1.8 | 65.9 | 3.7 | −1.7 | 5.3 |
| *Bacillus* SP-62449 Lichenase | 62.1 | −0.1 | 64.2 | 2.0 | 0.0 | 2.0 |
| amylase which the variant of SEQ ID NO: 28 having alterations R180* + S181* + S243Q + G475K | 62.3 | 0.1 | — | — | — | — |
| Blank | 62.2 | 0.0 | — | — | — | — |

TABLE 33

Wascator bottle wash in Model detergent X at 40° C., 30 min (pH 10.1)

Lichenase in combination with the amylase of SEQ ID NO: 29 having alterations D183* + G184* + W140Y + N195F + I206Y + Y243F + E260G + G304R + G476K

| | Enzymes solo | | REM | ΔREM | ΔREM | REM Synergy |
|---|---|---|---|---|---|---|
| | REM | ΔREM | combined | combined | theoretic | effect |
| *Bacillus agaradhaerens* lichenase | 62.0 | 0.2 | 66.4 | 4.5 | 2.1 | 2.4 |
| *Bacillus Akibai* Lichenase | 62.2 | 0.3 | 66.4 | 4.6 | 2.3 | 2.3 |
| *Bacillus Mojavensis* Lichenase | 61.8 | −0.1 | 68.5 | 6.7 | 1.9 | 4.8 |
| *Bacillus* SP-62449 Lichenase | 61.9 | 0.1 | 66.9 | 5.1 | 2.1 | 3.0 |
| Amylase of SEQ ID NO: 29 having alterations D183* + G184* + W140Y + N195F + I206Y + Y243F + E260G + G304R + G476K | 63.8 | 2.0 | — | — | — | — |
| Blank | 61.8 | 0.0 | — | — | — | — |

TABLE 34

Wascator bottle wash in Model detergent X at 40° C., 20 min (pH 10.1)

Lichenase in combination with the amylase, which is the variant of SEQ ID NO: 30 having alterations H1* + N54S + V56T + K72R + G109A + F113Q + R116Q + W167F + Q172G + A174S + G184T + N195F + V206L + K391A + P473R + G476K

| | Enzymes solo | | REM | ΔREM | ΔREM | REM Synergy |
|---|---|---|---|---|---|---|
| | REM | ΔREM | combined | combined | theoretic | effect |
| *Bacillus agaradhaerens* lichenase | 60.1 | −0.3 | 65.8 | 5.5 | 3.1 | 2.4 |
| *Bacillus Akibai* Lichenase | 58.9 | −1.4 | 63.1 | 2.8 | −0.1 | 2.9 |
| *Bacillus Mojavensis* Lichenase | 59.2 | −1.1 | 62.3 | 1.9 | 0.2 | 1.7 |
| *Bacillus* SP-62449 Lichenase | 59.8 | −0.6 | 62.6 | 2.3 | 0.8 | 1.5 |
| *Bacillus amyloliquefaciens* lichenase | 59.7 | −0.7 | 64.3 | 4.0 | 3.1 | 0.9 |
| *Bacillus Subtillis* Lichenase | 59.9 | −0.5 | 61.9 | 1.6 | 0.9 | 0.7 |
| Amylase, which is the variant of SEQ ID NO: 30 having alterations H1* + N54S + V56T + K72R + G109A + F113Q + R116Q + W167F + Q172G + A174S + G184T + N195F + V206L + K391A + P473R + G476K | 61.7 | 1.3 | — | — | — | — |
| Blank | 60.4 | 0.0 | — | — | — | — |

TABLE 35

Wascator bottle wash in Model detergent X at 40° C., 30 min (pH 10.1)

|  | Enzymes solo | | REM combined | ΔREM combined | ΔREM theoretic | REM Synergy effect |
|---|---|---|---|---|---|---|
|  | REM | ΔREM | | | | |
| *Bacillus agaradhaerens* lichenase | 62.3 | 0.4 | 76.1 | 14.2 | 6.2 | 7.9 |
| *Bacillus Akibai* Lichenase | 61.6 | −0.4 | 75.1 | 13.2 | 5.5 | 7.7 |
| *Bacillus Mojavensis* Lichenase | 61.4 | −0.6 | 74.2 | 12.2 | 5.3 | 7.0 |
| *Bacillus* SP-62449 Lichenase | 61.0 | −1.0 | 74.0 | 12.1 | 4.9 | 7.2 |
| *Bacillus amyloliquefaciens* lichenase | 62.1 | 0.1 | 73.3 | 11.3 | 6.0 | 5.3 |
| *Bacillus Subtillis* Lichenase | 62.2 | 0.2 | 73.9 | 11.9 | 6.1 | 5.8 |
| Amylase, which is the variant of SEQ ID NO: 31 having alterations M9L + R118K + G149A + G182T + G186A + D183* + G184* + N195F + T246V + T257I + Y295F + N299Y + R320K + M323T + A339S + E345R + R458K | 67.8 | 5.9 | — | — | — | — |
| Blank | 62.0 | 0.0 | — | — | — | — |

TABLE 36

Wascator bottle wash in ADW Model detergent A at 40° C., 30 min (pH 10.2)

|  | Enzymes solo | | REM combined | ΔREM combined | ΔREM theoretic | REM Synergy effect |
|---|---|---|---|---|---|---|
|  | REM | ΔREM | | | | |
| *Bacillus agaradhaerens* lichenase | 60.5 | −2.1 | 75.1 | 12.5 | 5.4 | 7.1 |
| *Bacillus Akibai* Lichenase | 60.7 | −1.9 | 73.9 | 11.3 | 5.6 | 5.7 |
| *Bacillus Mojavensis* Lichenase | 63.0 | 0.3 | 73.3 | 10.7 | 7.8 | 2.8 |
| *Bacillus* SP-62449 Lichenase | 60.8 | −1.8 | 74.5 | 11.9 | 5.7 | 6.2 |
| *Bacillus amyloliquefaciens* lichenase | 61.6 | −1.0 | 70.4 | 7.8 | 6.5 | 1.2 |
| amylase having SEQ ID NO: 12 | 70.1 | 7.5 | — | — | — | — |
| Blank | 62.6 | 0.0 | — | — | — | — |

TABLE 37

Wascator bottle wash in ADW Model detergent A at 40° C., 30 min (pH 10.2)

|  | Enzymes solo | | REM combined | ΔREM combined | ΔREM theoretic | REM Synergy effect |
|---|---|---|---|---|---|---|
|  | REM | ΔREM | | | | |
| *Bacillus agaradhaerens* lichenase | 60.9 | 1.3 | 71.8 | 12.1 | 8.0 | 4.2 |
| *Bacillus Akibai* Lichenase | 60.9 | 1.2 | 71.5 | 11.8 | 7.9 | 3.9 |
| *Bacillus Mojavensis* Lichenase | 61.3 | 1.6 | 71.3 | 11.6 | 8.3 | 3.3 |
| *Bacillus* SP-62449 Lichenase | 60.9 | 1.2 | 71.7 | 12.0 | 7.9 | 4.1 |
| *Bacillus amyloliquefaciens* lichenase | 60.9 | 1.3 | 68.5 | 8.8 | 8.0 | 0.9 |
| *Bacillus Subtillis* Lichenase | 60.3 | 0.6 | 68.4 | 8.8 | 7.3 | 1.5 |
| amylase which is the variant of SEQ ID NO: 23 having alterations G182* + D183* | 66.4 | 6.7 | — | — | — | — |
| Blank | 59.7 | 0.0 | — | — | — | — |

TABLE 38

Wascator bottle wash in ADW Model detergent A at 40° C., 30 min (pH 10.2)

|  | Enzymes solo | | Lichenase in combination with the amylase, which is the variant of SEQ ID NO: 24 having alterations H183* + G184* + I405L + A421H + A422P + A428T | | | |
|---|---|---|---|---|---|---|
|  | REM | ΔREM | REM combined | ΔREM combined | ΔREM theoretic | REM Synergy effect |
| *Bacillus agaradhaerens* lichenase | 60.9 | 1.3 | 73.3 | 13.7 | 8.0 | 5.6 |
| *Bacillus Akibai* Lichenase | 60.9 | 1.2 | 71.7 | 12.1 | 8.0 | 4.0 |
| *Bacillus Mojavensis* Lichenase | 61.3 | 1.6 | 72.2 | 12.5 | 8.4 | 4.2 |
| *Bacillus* SP-62449 Lichenase | 60.9 | 1.2 | 72.5 | 12.8 | 8.0 | 4.8 |
| *Bacillus amyloliquefaciens* lichenase | 60.9 | 1.3 | 68.9 | 9.2 | 8.1 | 1.2 |
| *Bacillus Subtillis* Lichenase | 60.3 | 0.6 | 68.6 | 8.9 | 7.4 | 1.5 |
| Amylase, which is the variant of SEQ ID NO: 24 having alterations H183* + G184* + I405L + A421H + A422P + A428T | 66.5 | 6.8 | — | — | — | — |
| Blank | 59.7 | 0.0 | — | — | — | — |

TABLE 39

Wascator bottle wash in ADW Model detergent A at 40° C., 30 min (pH 10.2)

|  | Enzymes solo | | Lichenase in combination with the amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K | | | |
|---|---|---|---|---|---|---|
|  | REM | ΔREM | REM combined | ΔREM combined | ΔREM theoretic | REM Synergy effect |
| *Bacillus agaradhaerens* lichenase | 60.5 | -2.1 | 73.1 | 10.9 | 2.3 | 8.2 |
| *Bacillus Akibai* Lichenase | 60.7 | -1.9 | 73.2 | 10.6 | 2.5 | 8.1 |
| *Bacillus Mojavensis* Lichenase | 63.0 | 0.3 | 74.0 | 11.4 | 4.7 | 6.6 |
| *Bacillus* SP-62449 Lichenase | 60.8 | -1.8 | 75.1 | 12.4 | 2.6 | 9.9 |
| *Bacillus amyloliquefaciens* lichenase | 61.6 | -1.0 | 70.8 | 8.2 | 3.4 | 4.8 |
| Amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K | 67.0 | 4.4 | — | — | — | — |
| Blank | 62.6 | 0.0 | — | — | — | — |

TABLE 40

Wascator bottle wash in ADW Model detergent A at 40° C., 30 min (pH 10.2)

| | Enzymes solo | | Lichenase in combination with the amylase which is the variant of SEQ ID NO: 24 having alterations R178* + G179* + E187P + I203Y + R458N + T459S + D460T + G476K | | | |
|---|---|---|---|---|---|---|
| | REM | ΔREM | REM combined | ΔREM combined | ΔREM theoretic | REM Synergy effect |
| *Bacillus Mojavensis* Lichenase | 62.4 | 1.0 | 69.8 | 8.4 | 7.1 | 1.3 |
| *Bacillus* SP-62449 Lichenase | 60.8 | −0.6 | 69.8 | 8.4 | 5.5 | 2.9 |
| amylase which is the variant of SEQ ID NO: 24 having alterations R178* + G179* + E187P + I203Y + R458N + T459S + D460T + G476K | 67.5 | 6.1 | — | — | — | — |
| Blank | 61.4 | 0.0 | — | — | — | — |

TABLE 41

Wascator bottle wash in ADW Model detergent A at 40° C., 30 min (pH 10.2)

| | Enzymes solo | | Lichenase in combination with the amylase which is the variant of SEQ ID NO: 27 having alteration M202L | | | |
|---|---|---|---|---|---|---|
| | REM | ΔREM | REM combined | ΔREM combined | ΔREM theoretic | REM Synergy effect |
| *Bacillus agaradhaerens* lichenase | 62.2 | 0.8 | 69.4 | 8.0 | 5.3 | 2.8 |
| *Bacillus Akibai* Lichenase | 62.0 | 0.6 | 69.5 | 8.1 | 5.1 | 3.0 |
| *Bacillus Mojavensis* Lichenase | 62.4 | 1.0 | 68.9 | 7.5 | 5.5 | 2.0 |
| *Bacillus* SP-62449 Lichenase | 60.8 | −0.6 | 69.3 | 7.9 | 3.9 | 4.0 |
| Amylase which is the variant of SEQ ID NO: 27 having alteration M202L | 65.9 | 4.5 | — | — | — | — |
| Blank | 61.4 | 0.0 | — | — | — | — |

TABLE 42

Wascator bottle wash in ADW Model detergent A at 40° C., 30 min (pH 10.2)

| | Enzymes solo | | Lichenase in combination with the amylase which the variant of SEQ ID NO: 28 having alterations R180* + S181* + S243Q + G475K | | | |
|---|---|---|---|---|---|---|
| | REM | ΔREM | REM combined | ΔREM combined | ΔREM theoretic | REM Synergy effect |
| *Bacillus Akibai* Lichenase | 62.0 | 0.7 | 67.5 | 6.2 | 3.9 | 2.3 |
| *Bacillus* SP-62449 Lichenase | 61.2 | −0.1 | 68.4 | 7.1 | 3.1 | 4.1 |
| *Bacillus amyloliquefaciens* lichenase | 62.3 | 1.0 | 67.4 | 6.1 | 4.2 | 2.0 |
| *Bacillus Subtillis* Lichenase | 61.9 | 0.6 | 66.5 | 5.2 | 3.8 | 1.3 |
| Amylase which the variant of SEQ ID NO: 28 having alterations R180* + S181* + S243Q + G475K | 64.5 | 3.2 | — | — | — | — |
| Blank | 61.3 | 0.0 | — | — | — | — |

TABLE 43

Wascator bottle wash in ADW Model detergent A at 40° C., 30 min (pH 10.2)

| | Enzymes solo | | REM combined | ΔREM combined | ΔREM theoretic | REM Synergy effect |
|---|---|---|---|---|---|---|
| | REM | ΔREM | | | | |
| *Bacillus Akibai* Lichenase | 60.0 | −1.8 | 65.7 | 3.9 | 1.3 | 2.6 |
| *Bacillus Mojavensis* Lichenase | 62.1 | 0.4 | 66.9 | 5.2 | 3.5 | 1.7 |
| *Bacillus amyloliquefaciens* lichenase | 62.0 | 0.3 | 65.9 | 4.2 | 3.4 | 0.8 |
| *Bacillus Subtillis* Lichenase | 61.6 | −0.2 | 65.7 | 3.9 | 2.9 | 1.0 |
| Amylase of SEQ ID NO: 29 having alterations D183* + G184* + W140Y + N195F + I206Y + Y243F + E260G + G304R + G476K | 64.8 | 3.1 | — | — | — | — |
| Blank | 61.7 | 0.0 | — | — | — | — |

Lichenase in combination with the amylase of SEQ ID NO: 29 having alterations D183* + G184* + W140Y + N195F + I206Y + Y243F + E260G + G304R + G476K

TABLE 44

Wascator bottle wash in ADW Model detergent A at 40° C., 20 min (pH 10.2)

| | Enzymes solo | | REM combined | ΔREM combined | ΔREM theoretic | REM Synergy effect |
|---|---|---|---|---|---|---|
| | REM | ΔREM | | | | |
| *Bacillus Akibai* Lichenase | 59.4 | −0.8 | 61.6 | 1.4 | −0.5 | 1.9 |
| *Bacillus amyloliquefaciens* lichenase | 60.5 | 0.4 | 61.8 | 1.6 | 0.7 | 1.0 |
| *Bacillus Subtillis* Lichenase | 60.1 | −0.1 | 61.5 | 1.3 | 0.3 | 1.0 |
| Amylase, which is the variant of SEQ ID NO: 30 haing alterations H1* + N54S + V56T + K72R + G109A + F113Q + R116Q + W167F + Q172G + A174S + G184T + N195F + V206L + K391A + P473R + G476K | 60.5 | 0.3 | — | — | — | — |
| Blank | 60.2 | 0.0 | — | — | — | — |

Lichenase in combination with the amylase, which is the variant of SEQ ID NO: 30 having alterations H1* + N54S + V56T + K72R + G109A + F113Q + R116Q + W167F + Q172G + A174S + G184T + N195F + V206L + K391A + P473R + G476K

TABLE 45

Wascator bottle wash in ADW Model detergent A at 40° C., 30 min (pH 10.2)

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 61.4 | −0.4 | 72.9 | 11.1 | 7.0 | 4.1 |
| *Bacillus Akibai* Lichenase | 60.0 | −1.8 | 74.1 | 12.4 | 5.7 | 6.7 |
| *Bacillus Mojavensis* Lichenase | 62.1 | 0.4 | 73.2 | 11.5 | 7.8 | 3.7 |
| *Bacillus SP-62449* Lichenase | 61.4 | −0.3 | 75.1 | 13.4 | 7.1 | 6.3 |
| *Bacillus amyloliquefaciens* lichenase | 62.0 | 0.3 | 72.6 | 10.8 | 7.7 | 3.1 |

Lichenase in combination with the amylase, which is the variant of SEQ ID NO: 31 having alterations M9L + R118K + G149A + G182T + G186A + D183* + G184* + N195F + T246V + T257I + Y295F + N299Y + R320K + M323T + A339S + E345R + R458K TABLE 45-continued Wascator bottle wash in ADW Model detergent A at 40° C., 30 min (pH 10.2)

|  | Enzymes solo | | REM combined | ΔREM combined | ΔREM theoretic | REM Synergy effect |
|---|---|---|---|---|---|---|
|  | REM | ΔREM |  |  |  |  |
| *Bacillus Subtillis* Lichenase | 61.6 | −0.2 | 71.1 | 9.3 | 7.3 | 2.1 |
| amylase, which is the variant of SEQ ID NO: 31 having alterations M9L + R118K + G149A + G182T + G186A + D183* + G184* + N195F + T246V + T257I + Y295F + N299Y + R320K + M323T + A339S + E345R + R458K | 69.2 | 7.4 | — | — | — | — |
| Blank | 61.7 | 0.0 | — | — | — | — |

TABLE 46

Wascator bottle wash in ADW Model detergent A at 40° C., 20 min (pH 10.2)

Lichenase in combination with the amylase which the variant of SEQ ID NO: 28 having alterations R180* + S181* + S243Q + G475K

|  | Enzymes solo | | REM combined | ΔREM combined | ΔREM theoretic | REM Synergy effect |
|---|---|---|---|---|---|---|
|  | REM | ΔREM |  |  |  |  |
| *Bacillus agaradhaerens* lichenase | 60.2 | −0.9 | 63.9 | 2.9 | 1.0 | 1.9 |
| *Bacillus Akibai* Lichenase | 60.4 | −0.6 | 65.5 | 4.5 | 1.2 | 3.3 |
| *Bacillus Mojavensis* Lichenase | 60.9 | −0.2 | 65.0 | 4.0 | 1.7 | 2.3 |
| *Bacillus amyloliquefaciens* lichenase | 60.9 | −0.1 | 63.9 | 2.9 | 1.7 | 1.1 |
| *Bacillus Subtillis* Lichenase | 60.7 | −0.4 | 63.5 | 2.5 | 1.5 | 1.0 |
| amylase which the variant of SEQ ID NO: 28 having alterations R180* + S181* + S243Q + G475K | 62.9 | 1.9 | — | — | — | — |
| Blank | 61.0 | 0.0 | — | — | — | — |

TABLE 47

Wascator bottle wash in ADW Model detergent A at 40° C., 20 min (pH 10.2)

Lichenase in combination with the amylase of SEQ ID NO: 29 having alterations D183* + G184* + W140Y + N195F + I206Y + Y243F + E260G + G304R + G476K

|  | Enzymes solo | | REM combined | ΔREM combined | ΔREM theoretic | REM Synergy effect |
|---|---|---|---|---|---|---|
|  | REM | ΔREM |  |  |  |  |
| *Bacillus agaradhaerens* lichenase | 60.2 | −0.9 | 65.0 | 4.0 | 1.8 | 2.2 |
| *Bacillus amyloliquefaciens* lichenase | 60.9 | −0.1 | 62.8 | 1.8 | 2.5 | −0.7 |
| amylase of SEQ ID NO: 29 having alterations D183* + G184* + W140Y + N195F + I206Y + Y243F + E260G + G304R + G476K | 63.7 | 2.6 | — | — | — | — |
| Blank | 61.0 | 0.0 | — | — | — | — |

Example 10: Synergistic Effect of Lichenases Combined with Proteases

I. Wascator Bottle Wash Method Description:

A Wascator bottle wash method was used to detect the performance of the enzymes. In a Wascator washing machine (FOM 71 Lab) was added bottles (60 mL, DSE PP 70×35 Aseptisk, material #: 216-2620, from VWR) with 25 mL detergent solution including enzyme(s) and four stains (C-H097-Cocoa/oatflakes, from Center for Testmaterials BV, P.O. Box 120, 3133 KT Vlaardingen, the Netherlands, 2 cm in diameter). Two kg ballast (tea towels, cotton) was included in the washing machine. Washed in 25 L water for 15 min at 40° C. in model detergent for laundry (model X) and in ADW model detergent A for automated dish wash. After wash the stains were rinsed with tap water twice (3 L) and dried overnight at room temperature in drying cabinet (Electrolux, Intuition, EDD2400). The remission was measured on a spectrophotometer (Macbeth Color-Eye 7000 Remissions) at 460 nm.

II. Results:

In this example the results of combining the individual mature lichenases of *Bacillus agaradhaerens* Lichenase (SEQ ID NO: 39, His-tagged, recombinant), *Bacillus akibai* Lichenase (SEQ ID NO: 38, His-tagged, recombinant), *Bacillus mojavensis* Lichenase (SEQ ID NO: 40, His-tagged, recombinant), *Bacillus* sp-62449 Lichenase (SEQ ID NO: 37, His-tagged, recombinant), *Bacillus amyloliquefaciens* Lichenase (SEQ ID NO: 32) and *Bacillus subtillis* Lichenase (SEQ ID NO: 33) with a protease (Savinase, SEQ ID NO: 34) was studied in order to investigate a potential synergy effect between the two enzyme classes in various detergents using the Wascator bottle wash method is shown. Comparisons were made with lichenase from *Bacillus amyloliquefaciens* and lichenase from *Bacillus subtilis* in Model detergent X and ADW model detergent A using lichenase concentration of 0.01 mg enzyme protein per liter and protease concentration of 0.23 mg enzyme protein per liter at 40° C. The detailed conditions are described in Table 48 and 49 and the results are shown in Table 50 and 51.

TABLE 48

| Experimental condition | |
|---|---|
| Detergent | Model detergent X (see Table 13) |
| Detergent dosage | 1.75 g/L |
| Test solution volume | 25 mL |
| pH | As is |
| Wash time | 15 minutes |
| Temperature | 40° C. |
| Water hardness | 12° dH |
| Protease concentration in test | 0.23 mg/L |
| Lichenase concentration in test | 0.01 mg/L |
| Test material | C-H097 Cocoa/oatflakes |

TABLE 49

| Experimental condition | |
|---|---|
| Detergent | ADW model detergent A (see Table 15) |
| Detergent dosage | 3.77 g/L |
| Test solution volume | 25 mL |
| pH | As is |
| Wash time | 15 minutes |
| Temperature | 40° C. |
| Water hardness | 21° dH |
| Protease concentration in test | 0.23 mg/L |
| Lichenase concentration in test | 0.01 mg/L |
| Test material | C-H097 Cocoa/oatflakes |

TABLE 50

Wascator bottle wash in Model detergent X at 40° C., 15 min (pH 10.1)

| | Lichenase in combination with the protease Savinase (SEQ ID NO: 34) | | | | | |
|---|---|---|---|---|---|---|
| | Enzymes solo | | REM | ΔREM | ΔREM | REM Synergy |
| | REM | ΔREM | combined | combined | theoretic | effect |
| *Bacillus agaradhaerens* lichenase | 40.0 | 6.1 | 54.5 | 20.6 | 10.6 | 10.0 |
| *Bacillus Akibai* Lichenase | 37.6 | 3.8 | 45.4 | 11.5 | 8.2 | 3.3 |
| *Bacillus Mojavensis* Lichenase | 37.6 | 3.7 | 50.9 | 17.0 | 8.2 | 8.7 |
| *Bacillus* SP-62449 Lichenase | 37.7 | 3.8 | 48.4 | 14.5 | 8.3 | 6.2 |
| *Bacillus amyloliquefaciens* lichenase | 34.6 | 0.7 | 42.8 | 8.9 | 5.2 | 3.6 |
| *Bacillus Subtillis* Lichenase | 35.8 | 1.9 | 42.8 | 8.9 | 6.4 | 2.5 |
| Savinase (SEQ ID NO: 34) | 38.4 | 4.5 | — | — | — | — |
| Blank | 33.9 | 0.0 | — | — | — | — |

TABLE 51

Wascator bottle wash in ADW Model detergent A at 40° C., 15 min (pH 10.2)

|  | Lichenase in combination with the protease Savinase (SEQ ID NO: 34) | | | | | |
|---|---|---|---|---|---|---|
|  | Enzymes solo | | REM | ΔREM | ΔREM | REM Synergy |
|  | REM | ΔREM | combined | combined | theoretic | effect |
| *Bacillus agaradhaerens* lichenase | 40.0 | 4.6 | 53.0 | 17.6 | 10.3 | 7.4 |
| *Bacillus Akibai* Lichenase | 36.8 | 1.4 | 52.2 | 16.8 | 7.1 | 9.7 |
| *Bacillus Mojavensis* Lichenase | 39.0 | 3.6 | 51.1 | 15.7 | 9.3 | 6.4 |
| *Bacillus* SP-62449 Lichenase | 42.7 | 7.3 | 59.6 | 24.2 | 12.9 | 11.3 |
| *Bacillus amyloliquefaciens* lichenase | 36.6 | 1.2 | 47.2 | 11.8 | 6.8 | 5.0 |
| *Bacillus Subtillis* Lichenase | 37.1 | 1.7 | 48.3 | 12.9 | 7.4 | 5.5 |
| Savinase (SEQ ID NO: 34) | 41.1 | 5.7 | — | — | — | — |
| Blank | 35.4 | 0.0 | — | — | — | — |

Example 11: Automated Dish Wash Cleaning of Cooked Oats with Lichenases

I. Automated Dish Washing Machine

Automated dish washing machines (Miele, G 1223, GSL-2) were used to show lichenase performance on cooked oats.

II. Results:

Full scale dish wash performance on cooked oats was tested in ADW model detergent A under the experimental conditions given in Table 52.

TABLE 52

| Experimental conditions: | |
|---|---|
| ADW Model detergent A (See Table 15) | |
| Detergent dosage | 3.77 g/L |
| Lichenase concentration | 0 or 0.3 mg enzyme protein/L |
| Amylase concentration | 0.5 mg enzyme protein/L |
| Water hardness | As is |
| Protease concentration | SEQ ID NO: 35: 3.7 mg enzyme protein/L |
|  | SEQ ID NO: 36: 5.9 mg enzyme protein/L |
| Test solution volume | 5.4 L |
| Miele machine | G 1223, GSL-2, program: 45° C./3'/8'/55 |
| Soiling (Oat:Milk:Sugar) | 150 g:300 mL:50 g |
| Soiling per plate | 35 g |
| Ballast | 50 g IKW ballast slurry |

The soiling was prepared by mixing grinded oats (150 g AXA Finvalsede Havregryn in an immersion blender "chopper), milk (300 mL) and suger (50 g) in a beaker. The mixture was heated to boiling point and cooked for 2 minutes. The soiling was added on porcelain plates (35 g) and dried overnight at 40° C. in an oven (Heraeus Instruments, Typ UT6200). The plates were cooled to room temperature, weighted, and washed in Miele dish washing machines (G 1223, GSL-2) for 8 min (main wash) at 45° C. with 50 g IKW ballast slurry in ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K; 0.5 mg enzyme protein/L) and proteases (SEQ ID NO: 35; 3.7 mg enzyme protein/L, SEQ ID NO: 36; 5.9 mg enzyme protein/L) or ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K; 0.5 mg enzyme protein/L), proteases (SEQ ID NO: 35; 3.7 mg enzyme protein/L, SEQ ID NO: 36; 5.9 mg enzyme protein/L) and lichenase (*Bacillus agaradhaerens* (SEQ ID NO: 39, His-tagged, recombinant; 0.3 mg enzyme protein/L).

An effect of the lichenase on cooked oats is clearly visual seen as well as weighted. The measured numbers are shown in Table 53 as well as the calculated number for soiling left on the plates after wash.

Calculations:

Weight of soiling left on plates before wash=Weight of plate and soiling before wash−Weight of plate with no soiling before wash.

Weight of soiling left on plates after wash=Weight of plate and soiling after wash−Weight of plate with no soiling before wash.

TABLE 53

Wash performance on cooked oats:

|  | Weight of plate and soiling before wash (g)* | Weight of plate and soiling after wash (g)* | Weight of plate with no soiling before wash (g)* | Weight of soiling left on plates before wash (g)* | Weight of soiling left on plates after wash (g)* |
|---|---|---|---|---|---|
| No lichenase | 530.6 | 515.9 | 514.5 | 16.1 | 1.4 |
| With lichenase | 549.0 | 533.0 | 532.8 | 16.2 | 0.2 |

*Average of 4 replicates.

Example 12: Automated Dish Wash Cleaning of Cooked and Burned-in Oats with Lichenases I. Automated Dish Washing Machine Automated dish washing machines (Miele, G 1223, GSL-2) were used to show lichenase performance on cooked and burned-in oats.

II. Results:

Full scale dish wash performance on cooked and burned-in oats was tested in ADW model detergent A under the experimental conditions given in Table 54.

TABLE 54

Experimental conditions:

| | ADW Model detergent A (See Table 15) |
|---|---|
| Detergent dosage | 3.77 g/L |
| Lichenase concentration | 0 or 0.3 mg enzyme protein/L |
| Amylase concentration | 0.5 mg enzyme protein/L |
| Water hardness | As is |
| Protease concentration | SEQ ID NO: 35: 3.7 mg enzyme protein/L |
| | SEQ ID NO: 36: 5.9 mg enzyme protein/L |
| Test solution volume | 5.4 L |
| Miele machine | G 1223, GSL-2, program: 45° C./3'/8'/55 |
| Soiling (Oat:Milk:Sugar) | 150 g:300 mL:50 g |
| Soiling per plate | 15 g |
| Ballast | 50 g IKW ballast slurry |

The soiling was prepared by mixing grinded oats (150 g AXA Finvalsede Havregryn in an immersion blender "chopper), milk (300 mL) and sugar (50 g) in a beaker. The mixture was heated to boiling point and cooked for 2 minutes. The soiling was added on steel plates (15 g) and dried in an oven (Heraeus Instruments, Typ UT6200) for 40 minutes at 140° C. The plates were cooled down, weighted, and washed in Miele dish washing machines (G 1223, GSL-2) for 8 min (main wash) at 45° C. with 50 g IKW ballast slurry in ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K, 0.5 mg enzyme protein/L) and proteases (SEQ ID NO: 35; 3.7 mg enzyme protein/L, SEQ ID NO: 36; 5.9 mg enzyme protein/L) or ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K; 0.5 mg enzyme protein/L), proteases (SEQ ID NO: 35; 3.7 mg enzyme protein/L, SEQ ID NO: 36; 5.9 mg enzyme protein/L) and lichenase (*Bacillus agaradhaerens*, SEQ ID NO: 39, His-tagged, recombinant; 0.3 mg enzyme protein/L). After wash the plates were dried at room temperature and weighted. Calculations:

Weight of soiling left on plates before wash=Weight of plate and soiling before wash–Weight of plate with no soiling before wash.

Weight of soiling left on plates after wash=Weight of plate and soiling after wash–Weight of plate with no soiling before wash.

A clear effect of the lichenase is seen on cooked and burned-in oats and the measured numbers are shown in Table 55 as well as the calculated number for soiling left on the plates after wash.

TABLE 55

Wash performance on cooked and burned-in oats:

| | Weight of plate and soiling before wash (g)* | Weight of plate and soiling after wash (g)* | Weight of plate with no soiling wash (g)* | Weight of soiling left on plates before wash (g)* | Weight of soiling left on plates after wash (g)* |
|---|---|---|---|---|---|
| No lichenase | 210.1 | 205.8 | 203.6 | 6.5 | 2.2 |
| With lichenase | 205.9 | 200.5 | 199.4 | 6.5 | 1.2 |

*Average of 6 replicates.

Example 13: Automated Dish Wash Cleaning of Uncooked Oats with Lichenases

I. Automated Dish Washing Machine

Automated dish washing machines (Miele, G 1223, GSL-2) were used to show lichenase performance on uncooked oats.

II. Results:

Full scale dish wash performance on uncooked oats was tested in ADW model detergent A under the experimental conditions given in Table 56.

TABLE 56

Experimental conditions:

| | ADW Model detergent A (see Table 15) |
|---|---|
| Detergent dosage | 3.77 g/L |
| Lichenase concentration | 0 or 0.3 mg enzyme protein/L |
| Amylase concentration | 0.5 mg enzyme protein/L |
| Water hardness | As is |
| Protease concentration | SEQ ID NO: 35: 3.7 mg enzyme protein/L |
| | SEQ ID NO: 36: 5.9 mg enzyme protein/L |
| Test solution volume | 5.4 L |
| Miele machine | G 1223, GSL-2, program: 45° C./3'/8'/55 |
| Soiling (Oat:Milk:Sugar) | 150 g:300 mL:50 g |
| Soiling per plate | 35 g |
| Ballast | 50 g IKW ballast slurry |

The soiling was prepared by mixing grinded oats (150 g AXA Finvalsede Havregryn in an immersion blender "chopper), milk (300 mL) and sugar (50 g) in a beaker. The soiling was added on porcelain plates (35 g) and dried overnight at 40° C. in an oven (Heraeus Instruments, Typ UT6200). The plates were cooled to room temperature, weighted, and washed in Miele dish washing machines (G 1223, GSL-2) for 8 min (main wash) at 45° C. with 50 g IKW ballast slurry in ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K, 0.5 mg enzyme protein/L) and proteases (SEQ ID NO: 35; 3.7 mg enzyme protein/L, SEQ ID NO: 36; 5.9 mg enzyme protein/L) or ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K; 0.5 mg enzyme protein/L), proteases (SEQ ID NO: 35; 3.7 mg enzyme protein/L, SEQ ID NO: 36; 5.9 mg enzyme protein/L) and lichenase (*Bacillus agaradhaerens*; SEQ ID NO: 39, His-tagged, recombinant; 0.3 mg enzyme protein/L). After wash the plates were dried at room temperature and weighted.

An effect of the lichenase on uncooked oats is clearly visual seen as well as weighted. The measured numbers are shown in Table 57 as well as the calculated number for soiling left on the plates after wash.

Calculations:

Weight of soiling left on plates before wash=Weight of plate and soiling before wash–Weight of plate with no soiling before wash.

Weight of soiling left on plates after wash=Weight of plate and soiling after wash–Weight of plate with no soiling before wash.

TABLE 57

Wash performance on uncooked oats:

| | Weight of plate and soiling before wash (g)* | Weight of plate and soiling after wash (g)* | Weight of plate with no soiling before wash (g)* | Weight of soiling left on plates before wash (g)* | Weight of soiling left on plates after wash (g)* |
|---|---|---|---|---|---|
| No lichenase | 530.5 | 515.2 | 514.5 | 16.0 | 0.7 |
| With lichenase | 548.8 | 532.8 | 532.8 | 16.0 | 0.0 |

*Average of 4 replicates.

Example 14: Wash Performance and Anti-Redeposition Effect of Lichenases

I. Mini Tera-O-Tometer (MiniTOM) Wash Assay

The Mini Tergo-To-Meter (MiniTOM) is a medium scale model wash system that can be applied to test 16 different wash conditions simultaneously. A MiniTOM is basically a large temperature controlled water bath with up to 16 open metal beakers (300 mL) submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the MiniTOM beakers have no lid, it is possible to withdraw samples during a MiniTOM experiment and assay for information on-line during wash.

The MiniTOM model wash system is mainly used in medium scale testing of detergents and enzymes at US or LA/AP wash conditions. In a MiniTOM experiment, factors such as the ballast to soil ratio and the fabric to wash liquor ratio can be varied. Therefore, the MiniTOM provides the link between small scale experiments, such as AMSA and mini-wash, and the more time consuming full scale experiments in top loader washing machines.

II. Results:

MiniTergotometer (MiniTOM) anti-redeposition by the lichenase, *Bacillus agaradhaerens* (SEQ ID NO: 7), was tested in model detergent A under the experimental conditions given in Table 58.

TABLE 58

| Experimental conditions: | |
|---|---|
| Model A (See Table 11) | |
| Detergent dosage | 3.33 g/L |
| Lichenase concentration | 0 or 0.3 mg enzyme protein/L |
| Amylase concentration | 0.2 mg enzyme protein/L |
| Water hardness | 15° dH ($Ca^{2+}:Mg^{2+}:HCO_3^- = 4:1:7.5$) |
| Test solution volume | 100 ml |

TABLE 58-continued

| Experimental conditions: | |
|---|---|
| Model A (See Table 11) | |
| Wash time | 20 minutes |
| Rotation | 120 rpm |
| pH | as is |
| Temperature | 20° C. |
| Test material | Textile sample C-H097 (Cocoa/oatflakes) was obtained from Center for Testmaterials BV, P.O. Box 120, 3133 KT Vlaardingen, the Netherlands. Swatches with no initial soiling: Prewashed Knitted cotton was obtained from Warwick Equest Ltd, Unit 55, Consett Business Park, Consett, County Durham, DH8 6BN, United Kingdom. |

The anti-redeposition (and wash performance) of the lichenase, *Bacillus agaradhaerens* (SEQ ID NO: 7), was tested as described below.

The wash solutions were prepared by adjusting the water hardness to 15° dH ($Ca^{2+}:Mg^{2+}:HCO_3^-=4:1:7.5$) by addition of $CaCl_2$, $MgCl_2$ and $NAHCO_3$, adding the desired amount of detergent (3.33 g/L of Model detergent A) and adjusting the temperature to 40° C. in the buckets. The detergent was dissolved during magnet stirring for 10 minutes (wash solution was used within 30 to 60 min after preparation). The temperature and rotation in the water bath in the MiniTOM were set to 40° C. and 120 rpm, respectively. When the temperature was adjusted according to settings (tolerance is +/−0.5° C.), 100 mL of the wash solution was added to the MiniTOM beakers (300 mL).

Swatches (1 knitted cotton swatches (circular, 2 cm in diameter) and 12 C-H097 (circular, 2 cm in diameter), lichenase (*Bacillus agaradhaerens* (SEQ ID NO: 39, His-tagged, recombinant), 0 or 0.3 mg enzyme protein/L) and amylase (SEQ ID NO: 12, 0.2 mg enzyme protein/L) were added to the beakers and washed for 20 minutes. Swatches were rinsed in cold tap water for 5 minutes. The swatches were sorted and dried between filter paper in a drying cupboard without heat overnight.

The anti-redeposition (and wash performance) was measured as the brightness of the color of the textile washed expressed in remission values (REM). Remission measurements were made using a Macbeth 7000 Color Eye spectrophotometer. Each of the dry swatches was measured. As there is a risk of interference from the back-ground, the swatches were placed on top of 2 layers of fabric during the measurement of the remission. The remission was measured at 460 nm. The UV filter was not included. An average result for remission for the swatches was calculated.

The anti-redeposition effect due to the presence of the lichenase is shown in Table 59. In the beakers without the lichenase present, the released soil from the soiled swatch (C-H097) is redeposit to the swatch with no initial soiling on. When the lichenase is present in the wash liquor, an anti-redeposition effect is clearly seen.

TABLE 59

Anti-redeposition effect and wash performance of licheneses:

| | REM before wash | REM after wash without Lichenase | REM after wash with Lichenase |
|---|---|---|---|
| Swatch with no initial soiling (Anti-redeposition) | 92.1 | 65.3 | 88.2 |
| Swatch with soiling (C-H097) (Wash performance) | 18.8 | 38.1 | 42.2 |

Example 15

Cleaning performance on oat flakes:
500 g oat flakes, 167 g sugar and 1 l semi-skimmed milk (1.5% fat) are intensely mixed. The mixture is let unstirred for at least 2 hours at room temperature. Afterwards, 15 g (+/−0.2 g) of this preparation is spread evenly on a plate (china) in form of a circle using a metal ring (radius 11 cm) and left to dry over night at 40° C.
Cleaning performance is tested in an automatic dishwashing machine Miele GSL, 21° dH, 45° C., 8 min holding time, and 55° C. rinse temperature, with soiled dish ware/cutlery placed inside (according to IKW method, Sbfwjournal, 142, (06), 2016, S. 33-48) with additional 4 plates as prepared above placed therein. Pasta and starch-mix cleaning performance was measured according to IKW. The results, also for oatflakes, are documented as arithmetic averages, evaluation according to IKW. Higher values indicated a better cleaning performance, differences above 1.0 are considered to be significant.
Cleaning Performance:
A two component liquid automatic dishwashing product (15 ml of each composition A and B, Table 60, 61) was dosed at the same time into the dosing chamber of the dishwashing machine.

TABLE 60

| Enzymphase (EP) | A |
|---|---|
| Amylase (wt. % enzyme protein) | 0.02 |
| Protease (wt. % enzyme protein) | 0.20 |
| Glycerol | 8.0 |
| Copolymer comprising sulfonic acid group containing monomer | 7.5 |
| MGDA Na4 | 10.00 |
| Nonionic surfactant(s) | 2.8 |
| Polypeptide according to invention (*mature polypeptide according to SEQ ID NO: 7) | s. below |
| Misc (perfume, colorant, stabilizers for enzymes and UV, glass corrosion inhibitors, thickener, water) | Ad 100 |
| pH-Wert (not diluted, 25° C.) | 7.5 |

TABLE 61

| Alkaline Phase (AP) | B |
|---|---|
| HEDP | 2.5 |
| MGDA (Tetranatriumsalz) | 3.5 |
| KOH | 3.2 |
| Sodium Carbonate | 8.5 |
| Kationic copolymer | 0.5 |
| Sodium citrate x 2H$_2$O | 14.0 |
| Misc (perfume, colorant, stabilizers for enzymes and UV, glass corrosion inhibitors, thickener, water) | Ad 100 |
| pH-Wert (not diluted, 25° C.) adjusted (KOH/Citric Acid) | 10.5 |

TABLE 62

| Cleaning performance | Oat flakes | Starch Mix |
|---|---|---|
| No Licheninase, prepared directly before testing | 6.5 | 7.3 |
| 1.5 mg Licheninase* in A, prepared directly before testing | 8.0 | 8.3 |

(*mature polypeptide according to SEQ ID NO: 7)

TABLE 63

| Cleaning performance | Spaghetti |
|---|---|
| No Licheninase, prepared directly before testing | 5.8 |
| 1 mg Licheninase* in A, prepared directly before testing | 7.5 |

(*mature polypeptide according to SEQ ID NO: 7)

TABLE 64

| Liquid automatic dishwashing product | Cleaning performance on Oat flakes |
|---|---|
| No Licheninase, storage conditions: 4 weeks at T = 22° C. | 5.9 |
| 1 mg Licheninase* in A, prepared directly before testing | 7.5 |
| 1 mg Licheninase* in A, storage conditions: 4 weeks at T = 22° C. | 7.3 |
| 1 mg Licheninase* in A, storage conditions: 4 weeks at T = 30° C. | 7.6 |
| 1 mg Licheninase* in A, storage conditions: 4 weeks at T = 40° C. | 7.1 |

(*mature polypeptide according to SEQ ID NO: 7)

Surprisingly, it has been found that the cleaning performance of a dishwash composition, preferably an automatic dishwash composition is enhanced on pasta (spaghetti) and/or starch-containing soils (Table 62, 63).
Therefore, licheninases of the invention facilitate removal of starch-containing soil in the presence of one or more amylases and enhance amylase related cleaning performance.
The cleaning performance of the dishwash composition on Oatflakes is not significantly altered after 4 weeks storage at different temperatures (Table 64). Comparable results were found for automatic dishwash compositions containing 1.5 or 2.0 mg active enzyme protein/job Licheninase, storage conditions: 8 weeks at T=40° C. or 2 weeks at T=50° C.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A detergent composition, comprising a surfactant and a polypeptide having beta-glucanase activity, wherein the polypeptide has at least 90% sequence identity to the sequence of amino acids 1-222 of SEQ ID NO: 7 or a fragment thereof, wherein the composition is in the form of a bar, a tablet, a powder, a granule, a paste or a liquid and is not a dish wash composition.

2. The detergent composition of claim 1, wherein the polypeptide has at least 95% sequence identity to the sequence of amino acids 1-222 of SEQ ID NO: 7.

3. The detergent composition of claim 1, wherein the polypeptide has at least 97% sequence identity to the sequence of amino acids 1-222 of SEQ ID NO: 7.

4. The detergent composition of claim 1, wherein the polypeptide comprises the sequence of amino acids 1-222 of SEQ ID NO: 7.

5. The detergent composition of claim 1, wherein the polypeptide consists of the sequence of amino acids 1-222 of SEQ ID NO: 7.

6. The detergent composition of claim 1, wherein the polypeptide is a fragment of the sequence of amino acids 1-222 of SEQ ID NO: 7, wherein the fragment has at least 90% sequence identity to the sequence of amino acids 1-222 of SEQ ID NO: 7 and has beta-glucanase activity.

7. The detergent composition of claim 1, which further comprises an alpha-amylase.

8. The detergent composition of claim 1, which further comprises a protease.

9. The detergent composition of claim 1, wherein the beta-glucanase activity is licheninase activity, capable of hydrolyzing beta-1,3, beta-1,4-glucans.

10. The detergent composition of claim 1, which has a pH of 7.5 or above.

11. A recombinant host cell, comprising multiple copies of a polynucleotide encoding a polypeptide having beta-glucanase activity, wherein the polypeptide has at least 90% sequence identity to the sequence of amino acids 1-222 of SEQ ID NO: 7.

12. The recombinant host cell of claim 11, wherein the polypeptide has at least 95% sequence identity to the sequence of amino acids 1-222 of SEQ ID NO: 7.

13. The recombinant host cell of claim 11, wherein the polypeptide has at least 96% sequence identity to the sequence of amino acids 1-222 of SEQ ID NO: 7.

14. A method of producing a polypeptide having beta-glucanase activity, comprising cultivating the host cell of claim 11 under conditions conducive for producing the polypeptide and recovering the polypeptide.

15. A method of producing a polypeptide having beta-glucanase activity, comprising cultivating the host cell of claim 12 under conditions conducive for producing the polypeptide and recovering the polypeptide.

16. A method of producing a polypeptide having beta-glucanase activity, comprising cultivating the host cell of claim 13 under conditions conducive for producing the polypeptide and recovering the polypeptide.

17. The method of claim 14, wherein the host cell is a bacterial cell selected from the group consisting of *Bacillus, Clostridium, Enterococcus, Geobacillus, Lactobacillus, Lactococcus, Oceanobacillus, Staphylococcus, Streptococcus, Streptomyces, Campylobacter, E. coli, Flavobacterium, Fusobacterium, Helicobacter, Ilyobacter, Neisseria, Pseudomonas, Salmonella,* and *Ureaplasma* cells.

18. The method of claim 14, wherein the host cell is a fungal cell selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* and *Trichoderma* cells.

19. A process of degrading a beta-glucan, comprising applying a polypeptide having beta-glucanase activity to the beta-glucan, wherein the polypeptide has at least 90% sequence identity to the sequence of amino acids 1-222 of SEQ ID NO: 7 and the process is not for cleaning dishes.

20. The method of claim 19, wherein the method is used for reducing or preventing soil redeposition.

* * * * *